United States Patent
Koyanagi et al.

(10) Patent No.: US 6,187,944 B1
(45) Date of Patent: Feb. 13, 2001

(54) ACRYLONITRILE COMPOUNDS, PROCESS FOR THEIR PRODUCTION AND PESTICIDES CONTAINING THEM

(75) Inventors: Toru Koyanagi; Yuji Nakamura; Masayuki Morita, all of Shiga; Koji Sugimoto, Tokyo; Tsuyoshi Ikeda; Munekazu Ogawa, both of Shiga, all of (JP)

(73) Assignee: Ishihara Sangyo Kaisha Ltd., Osaka (JP)

( * ) Notice: Under 35 U.S.C. 154(b), the term of this patent shall be extended for 0 days.

(21) Appl. No.: 09/355,945

(22) PCT Filed: Feb. 13, 1998

(86) PCT No.: PCT/JP98/00584

§ 371 Date: Aug. 16, 1999

§ 102(e) Date: Aug. 16, 1999

(87) PCT Pub. No.: WO98/35935

PCT Pub. Date: Aug. 20, 1998

(30) Foreign Application Priority Data

Feb. 14, 1997 (JP) .................................................. 9-047036
Jun. 18, 1997 (JP) .................................................. 9-179031
Sep. 25, 1997 (JP) .................................................. 9-279509

(51) Int. Cl.$^7$ .......................... C07C 255/38; C07C 255/00
(52) U.S. Cl. ................ 558/397; 514/237.5; 514/237.8; 514/241; 514/255.01; 514/267; 514/327; 514/330; 514/347; 514/354; 514/369; 514/372; 514/374; 514/398; 514/407; 514/424; 514/445; 514/473; 514/550; 544/163; 544/224; 544/316; 544/384; 544/219; 546/330; 546/226; 548/538; 548/542; 548/221; 548/230; 548/214; 548/243; 548/375.1; 558/398; 558/402; 558/48; 549/65; 549/495
(58) Field of Search .................... 558/402, 397, 558/398, 48; 514/550, 237.5, 237.8, 241, 255, 267, 327, 336, 347, 354, 369, 372, 374, 398, 407, 424, 495, 473; 544/163, 219, 224, 316, 384; 546/226, 330; 548/214, 221, 230, 243, 375.1, 528, 548; 549/65, 495

(56) References Cited

U.S. PATENT DOCUMENTS 2,766,271 * 10/1956 Rorig ..................... 558/402
3,337,565    8/1967 Bencze et al. ............. 558/402 X
3,337,566    8/1967 Walker et al. ............. 558/402 X
4,107,189 * 8/1978 Van Der Veen et al. ........ 558/402 X
4,469,688 * 9/1984 D'Silva .................................. 424/210
5,589,506 * 12/1996 Hashimoto et al. .................. 514/520

FOREIGN PATENT DOCUMENTS 0 104 690    4/1984  (EP) .

OTHER PUBLICATIONS

Patent Abstracts of Japan, vol. 9, No. 119 (C–282), May 23, 1985, JP 60 011452, Jan. 21, 1985.
Patent Abstracts of Japan, vol. 9, No. 119 (C–282), May 23, 1985, JP 60 011401, Jan. 21, 1985.
Lowe, Chemical Abstracts 124:117101, 1993.*
Norman, Chemical Abstracts 131L:157709, 1999.*

* cited by examiner

Primary Examiner—Floyd D. Higel
(74) Attorney, Agent, or Firm—Oblon, Spivak, McClelland, Maier & Neustadt, P.C.

(57) ABSTRACT

Acrylonitrile compounds having pesticidal activity of formula (I) and salts thereof.

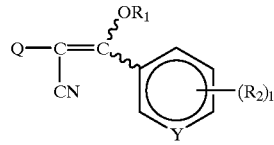

wherein Q is

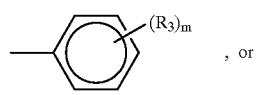

, or

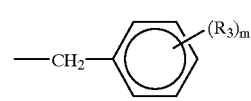

Y is =C($R_4$)— or =N—, $R_1$ is alkyl, haloalkyl, etc., each of $R_2$ and $R_3$ is halogen, alkyl which may be substituted, alkenyl which may be substituted, etc., $R_4$ is hydrogen, halogen, alkyl or haloalkyl, l is from 1 to 4, m is from 0 to 5, n is from 0 to 3, q is from 0 to 4, when 1 is 2 or more, a plurality of $R_2$ may be the same or different, when each of m, n and q is 2 or more, a plurality of $R_3$ may be the same or different.

19 Claims, No Drawings

ACRYLONITRILE COMPOUNDS, PROCESS FOR THEIR PRODUCTION AND PESTICIDES CONTAINING THEM

This application is a 371 of PCT/JP98/00584 filed Feb. 13, 1998.

DESCRIPTION

The present invention relates to novel acrylonitrile compounds useful as active ingredients for pesticides.

(1) EP 104690A, EP 62238A and U.S. Pat. No. 4,469,688, respectively, disclose compounds similar to the compounds of the present invention, but such compounds and the compounds of the present invention are different in their chemical structures.

(2) EP 776879A discloses a process for producing an enol ether which literally covers a part of the compounds of the present invention, but in this publication, there is no specific disclosure at all with respect to the group of compounds of the present invention.

(3) JP-A-60-11401 and JP-A-60-11452, respectively, disclose α-cyanoketone derivatives which literally cover a part of the compounds of the present invention, but in these publications, there is no specific disclosure at all with respect to the group of compounds of the present invention.

(4) U.S. Pat. No. 3,337,565 discloses acrylonitrile derivatives which literally cover a part of the compounds of the present invention, but in this publication, there is no specific disclosure at all with respect to the group of compounds of the present invention.

(5) U.S. Pat. No. 3,337,566 discloses acrylonitrile derivatives similar to the compounds of the present invention, but such derivatives and the compounds of the present invention are different in their chemical structures.

(6) WO97/40009 discloses ethylene derivatives similar to the compounds of the present invention, but the derivatives and the compounds of the present invention are different in their chemical structures.

(7) Bulletin de la Societe Chimique de France, 1980, No. 3–4, p. 163–166, discloses 3-(4-chlorophenyl)-2-phenyl-3-ethoxyacrylonitrile, but this compound and the compounds of the present invention are different in their chemical structures.

(8) Journal of Chemical Research (Synopses), 1987, p. 78–79, discloses 2-(3,5-dimethoxyphenyl)-3-(2-methoxy-4-methylphenyl)-3-acetoxyacrylonitrile and 2-(3,5-dimethoxyphenyl)-3-(2,6-dimethoxy-4-methylphenyl)-3-acetoxyacrylonitrile, but these compounds and the compounds of the present invention are different in their chemical structures.

The present inventors have conducted various studies to find out an excellent pesticide, paying an attention to acrylonitrile compounds and, as a result, have accomplished the present invention.

Namely, the present invention provides an acrylonitrile compound of the following formula (I) or its salt:

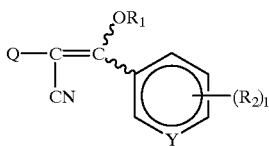

wherein Q is

Qa

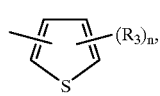
Qb

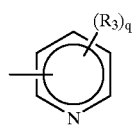
Qc or

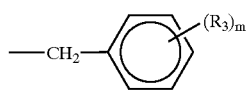
Qd

Y is =C($R_4$)— or =N—, $R_1$ is alkyl, haloalkyl, alkoxyalkyl, alkylthioalkyl, alkenyl, haloalkenyl, alkynyl, haloalkynyl, —C(=O)$R_5$, —C(=S)$R_5$, —S(O)$_w R_5$ or —CH$_2$R$_9$, each of $R_2$ and $R_3$ is halogen, alkyl which may be substituted, alkenyl which may be substituted, alkynyl which may be substituted, alkoxy which may be substituted, alkenyloxy which may be substituted, alkynyloxy which may be substituted, alkylthio which may be substituted, alkylsulfinyl which may be substituted, alkylsulfonyl which may be substituted, alkenylthio which may be substituted, alkenylsulfinyl which may be substituted, alkenylsulfonyl which may be substituted, alkynylthio which may be substituted, alkynylsulfinyl which may be substituted, alkynylsulfonyl which may be substituted, nitro, cyano, phenyl which may be substituted, phenoxy which may be substituted, phenylthio which may be substituted, phenylsulfinyl which may be substituted, phenylsulfonyl which may be substituted, benzyl which may be substituted, benzyloxy which may be substituted, benzylthio which may be substituted, or benzoyl which may be substituted, $R_4$ is hydrogen, halogen, alkyl or haloalkyl, $R_5$ is alkyl which may be substituted, alkenyl which may be substituted, alkynyl which may be substituted, alkoxy which may be substituted, alkenyloxy which may be substituted, alkynyloxy which may be substituted, alkylthio which may be substituted, alkenylthio which may be substituted, alkynylthio which may be substituted, cycloalkyl, cycloalkyloxy, cycloalkylthio, —N($R_7$)$R_8$, phenyl which may be substituted, phenoxy which may be substituted, phenylthio which may be substituted, benzyl which may be substituted, benzyloxy which may be substituted, benzylthio which may be substituted, —J, —O—J or —S—J, each of $R_7$ and $R_8$ is hydrogen, alkyl or alkoxy, $R_9$ is cyano, phenyl which may be substituted, phenoxy which may be substituted, phenylthio which may be substituted, phenylsulfinyl which may be substituted, phenylsulfonyl which may be substituted, benzyl which may be substituted, benzyloxy which may be substituted, benzylthio which may be substituted, benzoyl which may be substituted, —J, —C(=O)$R_{10}$, —C(=S)$R_{10}$, —S(O)$_w$$R_{10}$ or trimethylsilyl, $R_{10}$ is alkyl or alkoxy, J is a 5- or 6-membered heterocyclic group containing from 1 to 4 hetero atoms of at least one type selected from the group consisting of O, S and N (the heterocyclic group may be substituted), 1 is from 1 to 4, m is from 0 to 5, n is from 0 to 3, q is from 0 to 4, w is from 0 to 2, when 1 is 2 or more, a plurality of $R_2$ may be the same or different, when each of m, n and q is 2 or more, a plurality of $R_3$ may be the same or different, provided that the following compounds are excluded (1) a compound wherein Q is Qb, Y is =C($R_4$)—, and $R_1$ is alkyl, haloalkyl, alkoxyalkyl, alkylthioalkyl, alkenyl, haloalkenyl, alkynyl, haloalkynyl, —S(O)$_w$$R_5$ or —CH$_2$$R_9$, (2) a compound wherein Q is Qb, Y is =C($R_4$)—, $R_1$ is —C(=O)$R_5$, and $R_5$ is alkyl which may be substituted, alkenyl which may be substituted, alkynyl which may be substituted, alkoxy which may be substituted, alkenyloxy which may be substituted, alkynyloxy which may be substituted, cycloalkyl, cycloalkyloxy, —N($R_7$)$R_8$, phenyl which may be substituted, phenoxy which may be substituted, phenylthio which may be substituted, benzyl which may be substituted, benzyloxy which may be substituted, benzylthio which may be substituted, —J, —O—J or —S—J, (3) a compound wherein Q is Qb, Y is =C($R_4$)—, $R_1$ is —C(=S)$R_5$, and $R_5$ is —N($R_7$)$R_8$, (4) a compound wherein Q is Qb or Qc, Y is =N—, $R_1$ is alkyl or —C(=O)$R_5$, and $R_5$ is alkyl, (5) 3-(4-chlorophenyl)-2-phenyl-3-ethoxyacrylonitrile, (6) 2-(3,5-dimethoxyphenyl)-3-(2-methoxy-4-methylphenyl)-3-acetoxyacrylonitrile, and (7) 2-(3,5-dimethoxyphenyl)-3-(2,6-dimethoxy-4-methylphenyl)-3-acetoxyacrylonitrile; and a process for its production, a pesticide containing it, and a novel intermediate compound useful for its production.

In the formula (I), the substituent for the alkyl which may be substituted, the alkenyl which may be substituted, the alkynyl which may be substituted, the alkoxy which may be substituted, the alkenyloxy which may be substituted, the alkynyloxy which may be substituted, the alkylthio which may be substituted, the alkylsulfinyl which may be substituted, the alkylsulfonyl which may be substituted, the alkenylthio which may be substituted, the alkenylsulfinyl which may be substituted, the alkenylsulfonyl which may be substituted, the alkynylthio which may be substituted, the alkynylsulfinyl which may be substituted and the alkynylsulfonyl which may be substituted, for each of $R_2$ and $R_3$, or the substituent for the alkyl which may be substituted, the alkenyl which may be substituted, the alkynyl which may be substituted, the alkoxy which may be substituted, the alkenyloxy which may be substituted, the alkynyloxy which may be substituted, the alkylthio which may be substituted, the alkenylthio which may be substituted and the alkynylthio which may be substituted, for $R_5$, may, for example, be halogen, alkoxy, haloalkoxy, alkoxycarbonyl, alkylthio, alkylsulfinyl, alkylsulfonyl, haloalkylthio, haloalkylsulfinyl, haloalkylsulfonyl, amino, monoalkylamino, dialkylamino, nitro or cyano. The number of substituents may be one or more, and when it is more then one, a plurality of substituents may be the same or different.

Further, the substituent for the phenyl which may be substituted, the phenoxy which may be substituted, the phenylthio which may be substituted, the phenylsulfinyl which may be substituted, the phenylsulfonyl which may be substituted, the benzyl which may be substituted, the benzyloxy which may be substituted, the benzylthio which may be substituted or the benzoyl which may be substituted, for each of $R_2$ and $R_3$, the substituent for the phenyl which may be substituted, the phenoxy which may be substituted, the phenylthio which may be substituted, the benzyl which may be substituted, the benzyloxy which may be substituted or the benzylthio which may be substituted, for $R_5$, the substituent for the phenyl which may be substituted, the phenoxy which may be substituted, the phenylthio which may be substituted, the phenylsulfinyl which may be substituted, the phenylsulfonyl which may be substituted, the benzyl which may be substituted, the benzyloxy which may be substituted, the benzylthio which may be substituted or the benzoyl which may be substituted, for $R_9$, or the substituent for the heterocyclic ring for J, may, for example, be halogen, alkyl, haloalkyl, alkoxy, haloalkoxy, nitro, cyano, —S(O)$_w$$R_6$, amino, monoalkylamino or dialkylamino. The number of substituents may be one or more, and when it is more than one, a plurality of substituents may be the same or different. Here, $R_6$ is alkyl or haloalkyl, and w is from 0 to 2.

The heterocyclic group for J may, for example, be furyl, thienyl, pyrrolyl, pyrazolyl, imdazolyl, triazolyl, tetrazolyl, oxazolyl, isoxazolyl, thiazolyl, isothiazolyl, pyridyl, pyrimidinyl, 1-pyrrolidinyl, 1-piperidinyl or 4-morpholino.

Preferred compounds among the acrylonitrile compounds of the formula (I) or their salts, are as follows.

(a) The acrylonitrile compound or its salt, wherein Q is Qa, Qb or Qc, and each of $R_2$ and $R_3$ is halogen, alkyl, haloalkyl, alkoxy, haloalkoxy, alkylthio, alkylsulfinyl, alkylsulfonyl, nitro, cyano, phenyl which may be substituted by $M_1$, or phenoxy which may be substituted by $M_1$, $R_5$ is alkyl, haloalkyl, alkoxyalkyl, alkylthioalkyl, aminoalkyl, monoalkylaminoalkyl, dialkylaminoalkyl, alkenyl, haloalkenyl, alkynyl, haloalkynyl, alkoxy, haloalkoxy, alkylthio, haloalkylthio, alkoxycarbonylalkylthio, alkenylthio, haloalkenylthio, alkynylthio, haloalkynylthio, cycloalkyl, cycloalkylthio, —N($R_7$)$R_8$, phenyl which may be substituted by $M_1$, phenoxy which may be substituted by $M_1$, phenylthio which may be substituted by $M_1$, benzyl which may be substituted by $M_1$, benzylthio which may be substituted by $M_1$, pyridyl which may be substituted by $M_1$, 1-pyrrolidinyl, 1-piperidinyl, 4-morpholino, pyridyloxy which may be substituted by $M_1$, or pyridylthio which may be substituted by $M_1$, $R_9$ is cyano, phenyl which may be substituted by $M_1$, benzyloxy which may be substituted by $M_1$, benzoyl which may be substituted by $M_1$, pyridyl which may be substituted by $M_1$, —C(=O)$R_{10}$, —S(O)$_w$$R_{10}$ or trimethylsilyl, $M_1$ is halogen, alkyl, haloalkyl, alkoxy, haloalkoxy, nitro, cyano, —S(O)$_w$$R_6$, amino, monoalkylamino or dialkylamino, and $R_6$ is alkyl or haloalkyl. The number of substituents $M_1$ may be one or more, and if it is more than one, a plurality of $M_1$ may be the same or different.

(b) The acrylonitrile compound or its salt, wherein Q is Qa, Qb or Qc, each of $R_2$ and $R_3$ is halogen, alkyl, haloalkyl, alkoxy, haloalkoxy, alkylthio, alkylsulfinyl, alkylsulfonyl, nitro, cyano, phenyl which may be substituted by $M_2$, or phenoxy which may be substituted by $M_2$, $R_5$ is alkyl, haloalkyl, alkoxyalkyl, alkenyl, haloalkenyl, alkynyl, haloalkynyl, alkoxy, haloalkoxy, alkylthio, haloalkylthio, alkoxycarbonylalkylthio, alkenylthio, haloalkenylthio, alkynylthio, haloalkynylthio, cycloalkyl, cycloalkylthio, —N($R_7$)$R_8$, phenyl which may be substituted by $M_2$, phenoxy which may be substituted by $M_2$, phenylthio which may be substituted by $M_2$, benzyl which may be substituted by $M_2$, benzylthio which may be substituted by $M_2$, pyridyl which may be substituted by $M_2$, 1-pyrrolidinyl, 1-piperidinyl or 4-morpholino, each of $R_7$ and $R_8$ is hydrogen or alkyl, $R_9$ is cyano, phenyl which may be substituted by $M_2$, benzyloxy which may be substituted by $M_2$, benzoyl which may be substituted by $M_2$, pyridyl which may be substituted by $M_2$, —C(=O)$R_{10}$, —S(O)$_w R_{10}$ or trimethylsilyl, $M_2$ is halogen, alkyl, haloalkyl, alkoxy, haloalkoxy, nitro, cyano or —S(O)$_w R_6$, and $R_6$ is alkyl. The number of substituents $M_2$ may be one or more, and when it is more than one, a plurality of $M_2$ may be the same or different.

(c) The acrylonitrile compound or its salt according to the above (b), wherein Q is Qa or Qb.

(d) The acrylonitrile compound or its salt according to the above (c), wherein Q is Qa.

(e) The acrylonitrile compound of the above formula (I) or its salt, wherein Q is Qa or Qb, Y is =C($R_4$)—, and $R_4$ is hydrogen.

(f) The acrylonitrile compound or its salt according to the above (e), wherein Q is Qa.

(g) The acrylonitrile compound or its salt according to the above (e) or (f), wherein $R_2$ is halogen, alkyl or haloalkyl, and 1 is from 1 to 3.

(h) The acrylonitrile compound or its salt according to the above (e) or (f), wherein $R_1$ is alkoxyalkyl, —C(=O)$R_5$, —C(=S)$R_5$, —S(O)$_w R_5$ or —CH$_2 R_9$, $R_2$ is halogen, alkyl or haloalkyl, $R_3$ is halogen or alkyl, $R_5$ is alkyl, haloalkyl, alkoxyalkyl, alkoxy, haloalkoxy, alkylthio, haloalkylthio, alkoxycarbonylalkylthio, alkenylthio, —N($R_7$)$R_8$, phenyl which may be substituted by $M_3$, phenoxy which may be substituted by $M_3$, phenylthio which may be substituted by $M_3$, benzyl which may be substituted by $M_3$, pyridyl which may be substituted by $M_3$, 1-pyrrolidinyl or 4-morpholino, each of $R_7$ and $R_8$ is hydrogen or alkyl, $R_9$ is phenyl, $M_3$ is halogen, alkyl or alkoxy, 1 is from 1 to 3, m is from 0 to 3, n is from 0 to 1, and w is from 1 to 2. The number of substituents $M_3$ may be one or more, and when it is more than one, a plurality of $M_3$ may be the same or different.

(i) The acrylonitrile compound of the formula (I) or its salt, wherein the formula (I) is the formula (I-1);

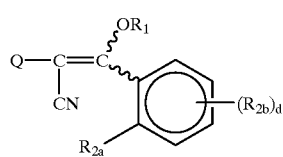

(I-1)

wherein Q is Qa or Qb, $R_{2a}$ is haloalkyl, $R_{2b}$ is halogen, alkyl or haloalkyl, d is from 0 to 2, m is from 0 to 3, and n is from 0 to 1. When d is 2, two $R_{2b}$ may be the same or different.

(j) The acrylonitrile compound or its salt according to the above (i), wherein Q is Qa.

(k) The acrylonitrile compound or its salt according to the above (i), wherein d is 0.

(l) The acrylonitrile compound or its salt according to the above (j), wherein d is 0.

(m) The acrylonitrile compound or its salt according to the above (i), (j), (k) or (l), wherein $R_1$ is alkoxyalkyl, —C(=O)$R_5$, —C(=S)$R_5$, —S(O)$_w R_5$ or —CH$_2 R_9$, $R_2$ is halogen, alkyl or haloalkyl, $R_3$ is halogen or alkyl, $R_5$ is alkyl, haloalkyl, alkoxyalkyl, alkoxy, haloalkoxy, alkylthio, haloalkylthio, alkoxycarbonylalkylthio, alkenylthio, —N($R_7$)$R_8$, phenyl which may be substituted by $M_3$, phenoxy which may be substituted by $M_3$, phenylthio which may be substituted by $M_3$, benzyl which may be substituted by $M_3$, pyridyl which may be substituted by $M_3$, 1-pyrrolidinyl or 4-morpholino, each of $R_7$ and $R_8$ is hydrogen or alkyl, $R_9$ is phenyl, $M_3$ is halogen, alkyl or alkoxy, 1 is from 1 to 3, m is from 0 to 3, n is from 0 to 1, and w is from 1 to 2.

In the compounds of the formula (I) or (a) to (m), the alkyl or alkyl moiety contained in $R_1$, $R_2$, $R_{2a}$, $R_{2b}$, $R_3$, $R_4$, $R_5$, $R_6$, $R_7$, $R_8$, $R_{10}$, $M_1$, $M_2$ or $M_3$, May, for example, be straight chain or branched one having from 1 to 6 carbon atoms such as methyl, ethyl, propyl, isopropyl, butyl, tert-butyl, pentyl or hexyl. The alkenyl, alkynyl, alkenyl moiety or alkynyl moiety contained in $R_1$, $R_2$, $R_3$ or $R_5$, may, for example, be straight chain or branched one having from 2 to 6 carbon atoms, such as vinyl, allyl, butadienyl, isopropenyl, ethynyl, propinyl or 2-penten-4-enyl. The cycloalkyl or cycloalkyl moiety contained in $R_5$, may, for example, be one having from 3 to 6 carbon atoms, such as cyclopropyl, cyclopentyl or cyclohexyl.

In the compounds of the formula (I) or (a) to (m), the halogen contained in $R_1$, $R_2$, $R_{2a}$, $R_{2b}$, $R_3$, $R_4$, $R_6$, $M_1$, $M_2$ or $M_3$, or the halogen as a substituent, may be fluorine, chlorine, bromine or iodine. The number of halogens as substituents may be one or more, and when it is more than one, a plurality of halogens may be the same or different.

The acrylonitrile compound of the formula (I) is capable of forming a salt. Such a salt may be any salt so long as it is acceptable for agriculture. For example, it may be an inorganic salt such as a hydrochloride, a sulfate or a nitrate, or an organic salt such as an acetate or a methanesulfonate.

The acrylonitrile compound of the formula (I) may have geometrical isomers (E-isomer and Z-isomer). The present invention includes such isomers and their mixtures.

The acrylonitrile compound of the formula (I) or its salt (hereinafter referred to simply as the compound of the present invention) can be produced, for example, by reactions (A) to (C) and by a usual process for producing a salt.

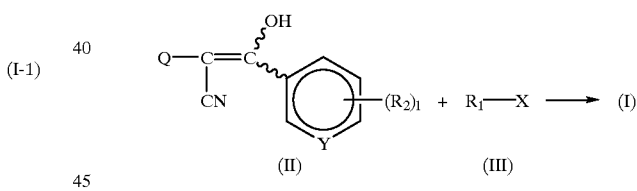

(A)

Now, the reaction (A) will be described.

In the reaction (A), Q, Y, $R_1$, $R_2$, 1 and the formula (I) are as defined above, and X is halogen.

The reaction (A) is carried out usually in the presence of a base. As such a base, one or more may suitably be selected for use from e.g. alkali metals such as sodium and potassium; alkali metal alcoholates such as potassium tertiary butoxide; carbonates such as potassium carbonate and sodium carbonate; bicarbonates such as potassium bicarbonate and sodium bicarbonate; metal hydroxides such as potassium hydroxide and sodium hydroxide; metal hydrides such as potassium hydride and sodium hydride; and tertiary amines such a trimethylamine, triethylamine, pyridine and 4-dimethylaminopyridine.

The reaction (A) may be carried out, if necessary, in the presence of a solvent. Such a solvent may be any solvent so long as it is inert to the reaction. For example, one or more may be suitably selected for use from e.g. aromatic hydrocarbons such as benzene, toluene, xylene and chlorobenzene; cyclic or non-cyclic aliphatic hydrocarbons such as carbon tetrachloride, methyl chloride, chloroform, dichloromethane, dichloroethane, trichloroethane, hexane and cyclohexane; ethers such as dioxane, tetrahydrofuran and diethyl ether; esters such as methyl acetate and ethyl acetate; dipolar aprotic solvents such as dimethylsulfoxide, sulfolane, dimethylacetamide, dimethylformamide, N-methylpyrrolidone and pyridine; nitriles such as acetonitrile, propionitrile and acrylonitrile; ketones such as acetone and methyl ethyl ketone; tertiary amines such as trimethylamine and triethylamine; and water.

For the reaction (A), a catalyst such as 4-dimethylaminopyridine may be used, as the case requires.

The reaction temperature for the reaction (A) is usually from −80 to +150° C., preferably from −50 to +120° C., and the reaction time is usually from 0.1 to 48 hours, preferably from 0.5 to 24 hours.

In a case where in the formula (I), $R_1$ is methyl:

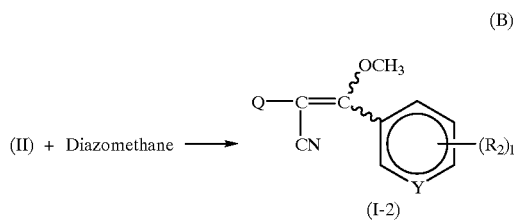

The reaction (B) will be described in detail. In the reaction (B), Q, Y, $R_2$, l and the formula (II) are as defined above.

The reaction (B) is carried out usually in the presence of a solvent. As such a solvent, one or more may suitably be selected for use from e.g. aromatic hydrocarbons such as benzene, toluene, xylene and chlorobenzene; cyclic or non-cyclic aliphatic hydrocarbons such as carbon tetrachloride, methyl chloride, chloroform, dichloromethane, dichloroethane, trichloroethane, hexane and cyclohexane; ethers such as dioxane, tetrahydrofuran and diethyl ether; esters such as methyl acetate and ethyl acetate; nitriles such as acetonitrile, propionitrile and acrylonitrile; and ketones such as acetone and methyl ethyl ketone.

The reaction temperature for the reaction (B) is usually from 0 to 100° C., preferably from 0 to 50° C., and the reaction time is usually from 0.1 to 24 hours, preferably from 0.1 to 12 hours.

In a case where in the formula (I), $R_1$ is —C(=O)$R_5$, —C(=S)$R_5$ or —S(O)$_w$$R_5$:

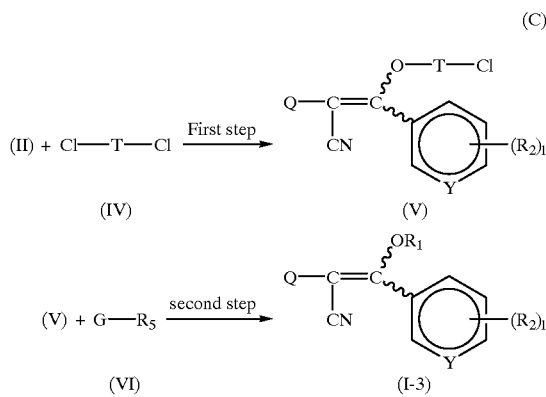

The reaction (C) will be described. In the reaction (C), Q, Y, $R_2$, $R_5$, l and the formula (II) are as defined above, T is —C(=O)—, —C(=S)— or —S(O)$_w$—, G is hydrogen, Li, MgBr, MgCl or MgI, and $R_{1a}$ is —C(=O)$R_5$, —C(=S)$R_5$ or —S(O)$_w$$R_5$ (wherein $R_5$ and w are as defined above).

The first step in the reaction (C) is carried out, if necessary, in the presence of a base. As such a base, one or more may suitably be selected for use from e.g. tertiary amines such as trimethylamine, triethylamine, pyridine and 4-dimethylaminopyridine.

The first step of the reaction (C) is carried out usually in the presence of a solvent. Such a solvent may be any solvent so long as it is inert to the reaction. For example, one or more may suitably selected for use from e.g. aromatic hydrocarbons such as benzene, toluene, xylene and chlorobenzene; cyclic or non-cyclic aliphatic hydrocarbons such as carbon tetrachloride, methyl chloride, chloroform, dichloromethane, dichloroethane, trichloroethane, hexane and cyclohexane; ethers such as dioxane, tetrahydrofuran and diethyl ether; and esters such as methyl acetate and ethyl acetate.

The reaction temperature for the first step of the reaction (C) is usually from −80 to +150° C., preferably from −50 to +80° C., and the reaction time is usually from 0.1 to 48 hours, preferably from 0.5 to 24 hours. The compound of the formula (V) prepared by the first step of the reaction (C) is a novel intermediate compound useful in the present invention.

The second step of the reaction (C) is carried out, if necessary, in the presence of a base. As such a base, one or more may suitably be selected for use from e.g. carbonates such as potassium carbonate and sodium carbonate; and tertiary amines such as trimethylamine, triethylamine, pyridine and 4-dimethylaminopyridine.

The second step of the reaction (C) is carried out usually in the presence of a solvent. Such a solvent may be any solvent so long as it is inert to the reaction. For example, one or more may suitably be selected for use from e.g. aromatic hydrocarbons such as benzene, toluene, xylene and chlorobenzene; cyclic or non-cyclic aliphatic hydrocarbons such as carbon tetrachloride, methyl chloride, chloroform, dichloromethane, dichloroethane, trichloroethane, hexane and cyclohexane; ethers such as dioxane, tetrahydrofuran and diethyl ether; esters such as methyl acetate and ethyl acetate; nitriles such as acetonitrile, propionitrile and acrylonitrile; and ketones such as acetone and methyl ethyl ketone.

The reaction temperature for the second step of the reaction (C) is usually from −80 to +150° C., preferably from −80 to +80° C., and the reaction time is usually from 0.1 to 48 hours, preferably from 0.5 to 24 hours.

The compounds of the formula (II) in the above reactions (A) to (C) are intermediate compounds useful for producing the compounds of the present invention, and novel compounds are included therein.

The compound of the formula (II) may form a salt. Such a salt may be any salt so long as it is agriculturally acceptable. For example, it may be an inorganic salt such as a hydrochloride, a sulfate or a nitrate; an organic salt such as an acetate or a methane sulfonate, an alkali metal salt such as a sodium salt or a potassium salt; an alkaline earth metal salt such as a magnesium salt or a calcium salt; or a quaternary ammonium salt such as dimethylammonium or triethylammonium.

The compound of the formula (II) has geometrical isomers (E-isomer and Z-isomer). The present invention includes such isomers and mixtures thereof. The compound of the formula (II) may also be present in the form of tautomers represented by the following formula:

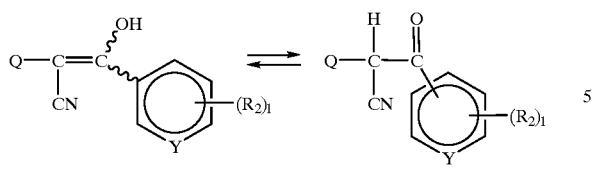

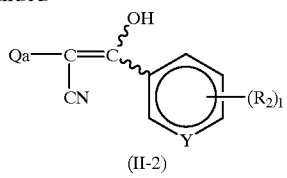

(II-2)

The present invention includes such tautomers and mixtures thereof.

Further, the compounds of the formula (II) include those which exhibit pesticidal activities.

The compound of the formula (II) or its salt may be prepared e.g. by reactions (D) to (F), or by a conventional method for producing a salt.

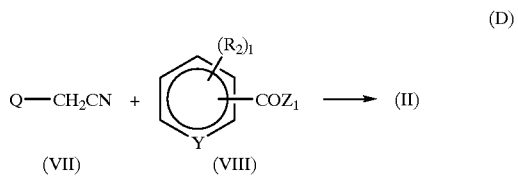

The reaction (D) will be described. In the reaction (D), Q, Y, $R_2$, 1 and the formula (II) are as defined above, and $Z_1$ is alkoxy.

The reaction (D) is carried out usually in the presence of a base and a solvent. As such a base, one or more may suitably be selected for use from e.g. alkali metals such as sodium and potassium; alkali metal alcoholates such as sodium methylate, sodium ethylate and potassium tertiary butoxide; metal hydrides such as potassium hydride and sodium hydride; and organic lithium such as methyllithium, butyllithium, tert-butyllithium and phenyllithium. As the solvent, one or more may suitably selected for use from e.g. aromatic hydrocarbons such as benzene, toluene, xylene and chlorobenene; ethers such as dioxane, tetrahydrofuran and diethyl ether; and alcohols such as methanol, ethanol, propanol and tert-butanol.

The reaction temperature for the reaction (D) is usually from −80 to +150° C., preferably from −50 to +120° C., and the reaction time is usually from 0.1 to 48 hours, preferably from 0.5 to 24 hours.

In a case where in the formula (II), Q is Qa:

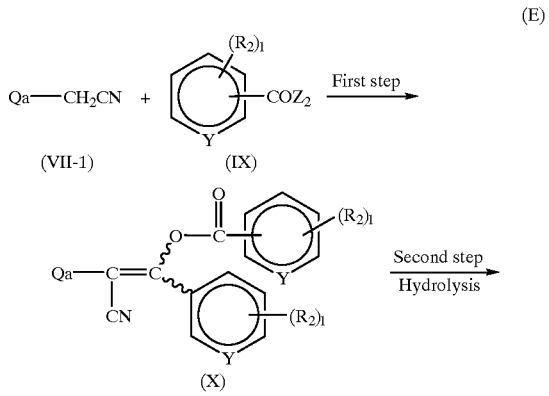

The reaction (E) will be described as follows. In the reaction (E), Qa, Y, $R_2$ and 1 are as defined above, and $Z_2$ is halogen.

The first step of the reaction (E) is carried out usually in the presence of a base. As such a base, one or more may suitably be selected for use from e.g. alkali metals such as sodium and potassium; alkali metal alcoholates such as sodium methylate, sodium ethylate and potassium tertiary butoxide; carbonates such as potassium carbonate and sodium carbonate; bicarbonates such as potassium bicarbonate and sodium bicarbonate; metal hydroxides such as potassium hydroxide and sodium hydroxide, metal hydrides such as potassium hydride and sodium hydride; amines such as monomethylamine, dimethylamine and trimethylamine; and pyridines such as pyridine and 4-dimethylaminopyridine.

The first step of the reaction (E) is carried out, if necessary, in the presence of a solvent. Such a solvent may be any solvent so long as it is inert to the reaction. For example, one or more may suitably be selected for use from e.g. aromatic hydrocarbons such as benzene, toluene, xylene and chlorobenene; cyclic or non-cyclic aliphatic hydrocarbons such as carbon tetrachloride, methyl chloride, chloroform, dichloromethane, dichloroethane, trichloroethane, hexane and cyclohexane; ethers such as dioxane, tetrahydrofuran and diethyl ether; esters such as methyl acetate and ethyl acetate; dipolar aprotic solvents such as dimethylsulfoxide, sulfolane, dimethylacetamide, dimethylformamide, N-methylpyrrolidone and pyridine; ketones such as acetone and methyl ethyl ketone; amines such as monomethylamine, dimethylamine and triethylamine; and water.

For the first step of the reaction (E), a catalyst such as 4-dimethylaminopyridine may be used, as the case requires.

The reaction temperature for the first step of the reaction (E) is usually from −80 to +150° C., preferably from −50 to +120° C., and the reaction time is usually from 0.1 to 48 hours, preferably from 0.5 to 24 hours.

The compound of the formula (X) prepared by the first step of the reaction (E) is a novel intermediate compound useful in the present invention and at the same time includes a compound of the present invention. Accordingly, the compound of the present invention can be prepared also by the first step of the reaction (E).

The second step of the reaction (E) is a hydrolysis reaction which is carried out usually in the presence of a base or an acid. As the base, one or more may suitably be selected for use from e.g. carbonates such as potassium carbonate and sodium carbonate; metal hydroxides such as potassium hydroxide and sodium hydroxide; and amines such as monomethylamine, dimethylamine and triethylamine. As the acid, one or more may suitably be selected for use from e.g. inorganic acids such as hydrochloric acid and sulfuric acid; and organic acids such as acetic acid.

The second step of the reaction (E) is carried out, if necessary, in the presence of a solvent. Such a solvent may be any solvent so long as it is inert to the reaction. For example, one or more may suitably be selected for use from e.g. nitriles such as acetonitrile, propionitrile and acrylonitrile; alcohols such a methanol, ethanol, propanol and tert-butanol; organic acids such as acetic acid and propionic acid; aqueous ammonia; and water.

The reaction temperature for the second step of the reaction (E) is usually from 0 to 100° C., preferably from 0 to 50° C., and the reaction time is usually from 0.1 to 48 hours, preferably from 0.5 to 24 hours.

In a case where in the formula (II), Q is Qc:

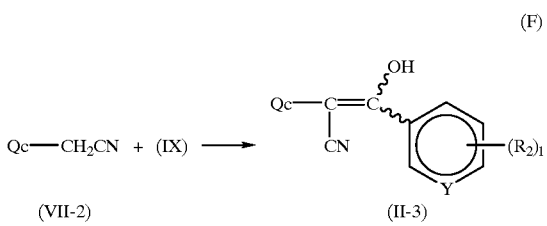

The reaction (F) will be described as follows. In the reaction (F), Qc, Y, $R_2$, 1 and the formula (IX) are as defined above.

The reaction (F) is carried out in accordance with the first step of the reaction (E).

Among compounds of the formula (II) thus prepared, the following compounds are particularly useful and novel.

Compounds of the formula (II-1) or their salts:

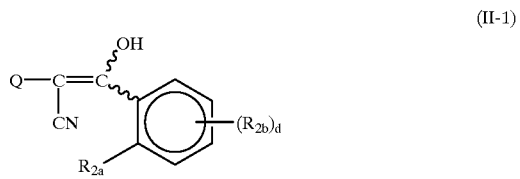

wherein Q, $R_{2a}$, $R_{2b}$ and d are as defined above, provided that when Q is Qc, (1) q is not 0, or (2) $R_3$ is not alkyl.

Particularly preferred compounds among the compounds of the formula (II-1) are as follows.

(n) A compound of the above formula (II-1) wherein Q is Qa or Qb, or its salts.

(o) A compound of the above formula (II-1) wherein Q is Qa, or its salt.

(p) A compound of the above formula (II-1), (n) or (o) wherein d is 0, or its salt.

The compounds of the present invention are useful as active ingredients for pesticides. They are particularly useful as active ingredients of pesticides such as an insecticide, a miticide, a nematicide, a soil pesticide, a fungicide and a marine antifouling agent.

Preferred embodiments of pesticides containing the compounds of the present invention will now be described. Firstly, pesticides such as an insecticide, a miticide, a nematicide, a soil pesticide and a fungicide, will be described.

The pesticides containing the compounds of the present invention are useful as an insecticide, a miticide, a nematicide and a soil pesticide (hereinafter referred to as insect pest control agents), and they are effective for controlling plant parasitic mites such as two-spotted spider mite (*Tetranychus urticae*), carmine spider mite (*Tetranychus cinnabarinus*), kanzawa spider mite (*Tetranychus kanzawai*), citrus red mite (*Panonychus citri*), European red mite (*Panonychus ulmi*), broad mite (*Polyphagotarsonemus latus*), pink citrus rust mite (*Aculops pelekassi*) and bulb mite (*Rhizoglyphus echinopus*); animal parasitic mites such as Ixodes; aphids such as green peach aphid (*Myzus persicae*) and cotton aphid (*Aphis gossypii*); agricultural insect pests such as diamondback moth (*Plutella xylostella*), cabbage armyworm (*Mamestra brassicae*), common cutworm (*Spodoptera litura*), codling moth (*Laspeyresia pomonella*), bollworm (*Heliothis zea*), tobacco budworm (*Heliothis virescens*), gypsy moth (*Lymantria dispar*), rice leafroller (*Cnaphalocrocis medinalis*), Adoxophyes sp., colorado potato beetle (*Leptinotarsa decemlineata*), cucurbit leaf beetle (*Aulacophora femoralis*), boll weevil (*Anthonomus grandis*), planthoppers, leafhoppers (Circulifer sp.), scales, bugs, whiteflies, thrips, grasshoppers, anthomyiid flies, scarabs, black cutworm (*Agrotis ipsilon*), cutworm (*Agrotis segetum*) and ants; plant parasitic nematodes such as root-knot nematodes, cyst nematodes, root-lesion nematodes, rice white-tip nematode (*Aphelenchoides besseyi*), strawberry bud nematode (*Nothotylenchus acris*), pine wood nematode (*Bursaphelenchus lignicolus*); gastropods such as slugs and snails; soil pests such as isopods such as pillbugs (*Armadilidium vulgare*) and pillbugs (*Porcellio scaber*); hygienic insect pests such as tropical rat mite (*Ornithonyssus bacoti*), cockroachs, housefly (*Musca domestica*) and house mosquto (*Culex pipiens*); stored grain insect pests such as angoumois grai moth (*Sitotroga cerealella*), adzuki bean weevil (*Callosobruchus chinensis*), red flour beetle (*Tribolium castaneum*) and mealworms; household goods insect pests such as casemaking clothes moth (*Tinea pellionella*), black carpet beetle (*Anthrenus scrophularidae*) and subterranean termites; domestic mites such as mold mite (*Tyrophagus putrescentiae*), *Dermatophagoides farinae* and *Chelacaropsis moorei*; and others such as fleas, lice and flies, which are parasitic to e.g. domestic animals. Among them, the insect pest control agents containing the compounds of the present invention are particularly effective for controlling plant parasitic mites, animal parasitic mites, agricultural insect pests, hygienic insect pests, household goods insect pests, domestic mites or the like. Further, they are effective against insect pests having acquired resistance to organophosphorus, carbamate and/or synthetic pyrethroid insecticides. Moreover, the compounds of the present invention have excellent systemic properties, and by the application of the compounds of the present invention to solid treatment, not only noxious insects, noxious mites, noxious nematodes, noxious gastropods and noxious isopods in soil but also foliage pests can be controlled.

Further, the pesticides containing compounds of the present invention are useful as fungicides. For example, they are effective for controlling diseases, such as blast (*Pyricularia oryzae*), sheath blight (*Rhizoctonia solani*) and brown spot (*Cochliobolus miyabeanus*) against rice; powdery mildew (*Erysiphe graminis*), scab (*Gibberella zeae*), rust (*Puccinia striiformis, P. coronata, P. graminis, P. recondita, P. hordei*), snow blight (Typhula sp., *Micronectriella nivalis*), loose smut (*Ustilago tritici, U. nuda*), eye spot (*Pseudocercosporella herpotrichoides*), leaf blotch (*Septoria tritici*) and glume blotch (*Leptosphaeria nodorum*) against cereals; melanose (*Diaporthe citri*) and scab (*Elsinoe fawcetti*) against citrus; blossom blight (*Sclerotinia mali*), powdery mildew (*Podosphaera leucotricha*), alternaria blotch (*Alternaria mali*) and scab (*Venturia inaequalis*) against apples; scab (*Venturia nashicola*) and black spot (*Alternaria kikuchiana*) against pears; brown rot (*Monilinia fructicola*), scab (*Cladosporium carpophilum*) and phomopsis rot (Phomopsis sp.) against peaches; anthracnose (*Elsinoe ampelina*) ripe rot (*Glomerella cingulata*), powdery mildew (*Uncinula necator*) and downy mildew (*Plasmopara viticola*) against grapes; anthracnose (*Gloeosporium kaki*) and angular leaf spot (*Cercospora kaki*) against Japanese persimon; anthracnose (*Colletotrichum lagenarium*), powdery mildew (*Sphaerotheca fuliginia*), gummy stem blight (*Mycosphacrella melonis*) and downy mildew (*Pseudopernospora cubensis*) against cucurbits; early blight (*Alternaria solani*), leaf mold (*Cladosporium fulvum*) and late blight (*Phytophthora infestans*) against tomatoes; alternaria leaf spot (*Alternaria brassicae*) against crucifer; early blight (*Alternaria solani*) and late blight (*Phytophthora infestans*) against potatoes; powdery mildew (*Sphaerotheca humuli*) against strawberry; gray mold (*Botrytis cinerea*) and sclerotinial rot (*Sclerotinia sclerotiorum*) against various crop plants. Further, they are effective also for controlling soil diseases brought about by plant pathogenic fungi such as Fusarium sp., Pythium sp., Rhizoctonia sp., Verticillium sp., and Plasmodiophora sp.

Another preferred embodiments of the pesticides containing compounds of the present invention may be agricultural and horticultural pesticides which collectively control the above-mentioned plant parasitic mites, agricultural insect pests, plant parasitic nematodes, gastropods, soil pests, various diseases and various soil diseases.

The pesticide such as the insect pests control agent or the fungicide containing the compound of the present invention, is usually formulated by mixing the compound with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected for use among those known in this field, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the compound of the present invention to the various agricultural adjuvants is usually from 0.001:99.999 to 95:5, preferably from 0.005:99.995 to 90:10.

In the actual application of such a formulation, it may be used as it is, or may be diluted to a predetermined concentration with a diluent such as water, and various extenders may be added thereto, as the case requires.

The application of the pesticide such as the insect pest control agent or the fungicide containing the compound of the present invention can not generally be defined, as it varies depending upon the weather conditions, the type of the formulation, the application season, the application site or the types or degree of outbreak of the pest insects. However, it is usually applied in a concentration of the active ingredient being from 0.05 to 800,000 ppm, preferably from 0.5 to 500,000 ppm, and the dose per unit area is such that the compound of the present invention is from 0.05 to 10,000 g, preferably from 1 to 5,000 g, per hectare. The application of the insect pest control agent as a preferred embodiment of the pesticide containing the compound of the present invention, can not generally be defined, as it varies depending upon various conditions as mentioned above, but is usually carried out in a concentration of the active ingredient being from 0.1 to 500,000 ppm, preferably from 1 to 100,000 ppm, and the dose per unit area is such that the compound of the present invention is from 0.1 to 10,000 g, preferably from 10 to 1,000 g, per hectare. The application of the fungicide can not generally be defined, as it varies depending upon various conditions as described above, but is usually carried out in a concentration of the active ingredient being from 0.1 to 500,000 ppm, preferably from 1 to 100,000 ppm, and the dose per unit area is such that the compound of the present invention is from 0.1 to 10,000 g, preferably from 10 to 1,000 g, per hectare. Further, agricultural and horticultural pesticides as another preferred embodiment of pesticides containing the compounds of the present invention may be applied in accordance with the above-described application of insect pest control agents and fungicides. The present invention includes such a method for controlling insect pests by such applications.

Various formulations of pesticides such as insect pest control agents or fungicides containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Further, the pesticides such as insect pest control agents or fungicides containing compounds of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, an insecticide, a miticide, a nematicide, a soil pesticide, a fungicide, an antivirus agent, an attractant, an antibiotic, a plant hormone and a plant growth regulating agent. Especially, with a mixed pesticide having a compound of the present invention mixed with or used in combination with one or more active compounds of other agricultural chemicals, the application range, the application time, the pesticidal activities, etc. may be improved to preferred directions. The compound of the present invention and the active compounds of other agricultural chemicals may separately be formulated so that they may be mixed for use at the time of application, or they may be formulated together. The present invention includes such a mixed pesticidal composition.

The mixing ratio of the compound of the present invention to the active compounds of other agricultural chemicals can not generally be defined, since it varies depending upon the weather conditions, the types of formulations, the application time, the application site, the types or degree of outbreak of insect pests, etc., but it is usually within a range of from 1:300 to 300:1, preferably from 1:100 to 100:1, by weight. Further, the dose for the application is such that the total amount of the active compounds is from 0.1 to 5,000 g, preferably from 10 to 3,000 g, per hectare. The present invention includes a method for controlling insect pests by an application of such a mixed pesticide composition.

The active compounds of insect pest control agents such as insecticides, miticides, nematicides or soil pesticides in the above-mentioned other agricultural chemicals, include, for example, (by common names, some of them are still in an application stage) organic phosphate compounds such as Profenofos, Dichlorvos, Fenamiphos, Fenitrothion, EPN, Diazinon, Chlorpyrifos-methyl, Acephate, Prothiofos, Fosthiazate and Phosphocarb; carbamate compounds such as Carbaryl, Propoxur, Aldicarb, Carbofuran, Thiodicarb, Methomyl, Oxamyl, Ethiofencarb, Pirimicarb, and Fenobucarb; nereistoxin derivatives such as Cartap, and Thiocyclam; organic chlorine compounds such as Dicofol, and Tetradifon; organometallic compounds such as Fenbutatin Oxide; pyrethroid compounds such as Fenvalerate, Permethrin, Cypermethrin, Deltamethrin, Cyhalothrin, Tefluthrin, and Ethofenprox; benzoylurea compounds such as Diflubenzuron, Chlorfluazuron, Teflubenzuron, and Novaluron; juvenile hormone-like compounds such as Methoprene; pyridazinone compounds such as Pyridaben; pyrazole compounds such as Fenpyroximate, Fipronil, and Tebufenpyrad; neonicotinoids such as Imidacloprid, Nitenpyram, Acetamiprid, Diacloden, and Thiacloprid; hydrazine compounds such as Tebufenozide, Methoxyfenozide, and Chromafenozide; dinitro compounds; organic sulfur compounds; urea compounds; triazine compounds; hydrazone compounds; and other compounds, such as Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, and Cyromazin. Further, BT agents, microbial agricultural chemicals such as insect viruses, or antibiotics such as Avermectin, Milbemycin and Spinosad, may be used in admixture or in combination.

The active compounds of fungicides among the above-mentioned other agricultural chemicals include, for example, (by common names, some of which are still in an application stage) pyrimidinamine compounds such as Mepanipyrim, Pyrimethanil, and Cyprodinil; azole compounds such as Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, and Tetraconazole; quinoxaline compounds such as Quinomethionate; dithiocarbamate compounds such as Maneb, Zineb, Mancozeb, Polycarbamate, Propineb; organic chlorine compounds such as Fthalide, Chlorothalonil, and Quintozene; imidazole compounds such as Benomyl, Thiophanate-Methyl, Carbendazim, and 4-chloro-2-cyano-1-dimethylsulfamoyl-5-(4-methylphenyl) imidazole; pyridinamine compounds such as Fluazinam; cyanoacetamide compounds such as Cymoxanil; phenylamide compounds such as Metalaxyl, Oxadixyl, Ofurace, Benalaxyl, Furalaxyl, and Cyprofuram; sulfenic acid compounds such as Dichlofluanid; copper compounds such as cupric hydroxide, and Oxine Copper; isoxazole compounds such as Hydroxyisoxazole; organophosphorus compounds such as Fosetyl-Al, Tolcofos-Methyl, S-benzyl O,O-diisopropylphosphorothioate, O-ethyl S,S-diphenylphosphorodithioate, and aluminumethylhydrogen phosphonate; N-halogenothioalkyl compounds such as Captan, Captafol, and Folpet; dicarboximide compounds such as Procymidone, Iprodione, and Vinclozolin; benzanilide compounds such as Flutolanil, and Mepronil; piperazine compounds such as Triforine; pyrizine compounds such as Pyrifenox; carbinol compounds such as Fenarimol; and Flutriafol; piperidine compounds such as Fenpropidine; morpholine compounds such as Fenpropimorph; organotin compounds such as Fentin Hydroxide, and Fentin Acetate; urea compounds such as Pencycuron; cinnamic acid compounds such as Dimethomorph; phenylcarbamate compounds such as Diethofencarb; cyanopyrrole compounds such as Fludioxonil, and Fenpiclonil; β-methoxyacrylate compounds such a Azoxystrobin, Kresoxim-Methyl, and Metominofen; oxazolidinedione compounds such as Famoxadone; anthraquinone compounds; crotonic acid compounds; antibiotics; and other compounds, such as Isoprothiolane, Tricyclazole, Pyroquilon, Diclomezine, Pro. benazole, Quinoxyfen, Propamocarb Hydrochloride and Spiroxamine.

Now, pesticides like marine antifouling agents will be described.

The marine antifouling agents containing the compounds of the present invention are effective for controlling noxious marine organisms against ships or underwater structures (such as harbour structures, buoys, pipelines, bridges, submarine bases, seabed oilfield drilling installations, water conduits for power plants, fixed shore nets and culturing nets). Specifically, they are effective for preventing the attachment and propagation of plants such as green algae and brown algae, animals such as a barnacle, a serpla, an ascidian, a sea mussel and an oyster, various bacteria called slime, and aquatics such as mold and a diatom, at the bottoms of ships or on underwater structures.

The marine antifouling agents containing the compounds of the present invention provide antifouling and antislime properties over a long period of time and exhibit excellent effects for preventing the attachment and propagation of noxious marine organisms against ships or underwater structures.

The marine antifouling agents containing the compounds of the present invention are usually formulated and used in the form of paint compositions. However, they may be formulated and used in other forms (such as solutions, emulsifiable concentrates, or pellets) as the case requires. Paint vehicles to be used for formulating the compounds of the present invention into coating compositions, may be resin vehicles which are commonly used. For example, a vinyl chloride resin, a vinyl chloride-vinyl acetate copolymer, a vinyl chloride-vinyl isobutyl ether copolymer, a chlorinated rubber resin, a chlorinated polyethylene resin, a chlorinated polypropylene resin, an acrylic resin, a styrene-butadiene resin, a polyester resin, an epoxy resin, a phenol resin, a synthetic rubber, a silicone rubber, a silicone resin, a petroleum resin, a oil and fat resin, a rosin ester resin, a rosin soap or rosin, may be mentioned. Further, as a vehicle having antifouling properties, an acrylic copolymer resin composition containing, as constituting units, an organotin compound salt of an unsaturated mono- or di-carboxylic acid, obtainable by a condensation reaction of (meth)acrylic acid with an organotin compound such as bis(tributyltin)oxide or triphenyltin hydroxide, or a resin containing a metal element such as copper, zinc or tellurium in its side chains, may, for example, be used.

When the compound of the present invention is formulated as a coating composition, the blend proportion is adjusted so that the compound of the present invention will be contained in an amount of from 0.1 to 60 wt %, preferably from 1 to 40 wt %, based on the entire coating composition.

The coating composition containing the compound of the present invention can be prepared by using e.g. a ball mill, a pebble mill, a roll mill or a sand grinder in accordance with a method which is well known in the field of preparing coating materials. Further, the above coating composition may contain a plasticizer, a coloring pigment, an extender pigment, an organic solvent, etc. which are commonly used in this field.

The coating composition containing the compound of the present invention may further contain any other known inorganic or organic antifouling agent, as the case requires. Such an antifouling agent includes, for example, cuprous oxide, copper rhodanide, copper hydroxide, copper naphthenate, metallic copper and various tin compounds and dithiocarbamic acid derivatives, such as tetramethylthiuram monosulfide, tetramethylthiuram disulfide, zinc bis-(dimethyldithiocarbamate), zinc ethylene-bis (dithiocarbamate), manganese ethylene-bis (dithiocarbamate), and copper bis (dimethyldithiocarbamate).

As described in the foregoing, the compound of the present invention or the compound of the formula (II) as its intermediate, is effective as an active ingredient of a pesticide. Various embodiments thereof will be summarized as follows.

(1) A pesticide containing a compound of the above formula (I) or (II), or its salt, as an active ingredient, or a method for controlling pests by employing such a compound.

(2) An agricultural and horticultural pesticide containing a compound of the above formula (I) or (II), or its salt, as an active ingredient, or a method for controlling pests in an agricultural and horticultural field by employing such a compound.

(3) An insect pest control agent containing a compound of the above formula (I) or (II), or its salt, as an active ingredient, or a method for controlling pests by employing such a compound.

(4) An insecticide containing a compound of the above formula (I) or (II), or its salt, as an active ingredient, or a method for controlling noxious insects by employing such a compound.

(5) A miticide containing a compound of the above formula (I) or (II), or its salt, as an active ingredients, or a method for controlling mites by employing such a compound.

(6) A nematicide containing a compound of the above formula (I) or (II), or its salt, as an active ingredient, or a method for controlling nematodes by employing such a compound.

(7) A soil pesticide containing a compound of the above formula (I) or (II), or its salt, as an active ingredient, or a method for controlling soil pests by employing such a compound.

(8) A fungicide containing a compound of the above formula (I) or (II), or its salt, as an active ingredient, or a method for controlling fungi by employing such a compound.

(9) A marine antifouling agent containing a compound of the above formula (I) of (II), or its salt, as an active ingredient, or a method for controlling marine fouling organisms by employing such a compound.

Now, the present invention will be described in further detail with reference to Examples. However, it should be understood that the present invention is by no means restricted to such specific Examples. Firstly, Examples for preparing compounds of the present invention will be described.

PREPARATION EXAMPLE 1

Preparation of β-(2-chlorophenyl)-β-isopropylcarbonyloxy-α-(2-thienyl)acrylonitrile (after-mentioned Compound No. b-35)

1) 1.12 g of sodium was added to 25 ml of dry ethanol, followed by heating to a reflux temperature. Then, a mixture comprising 5.0 g of 2-thiopheneacetonitrile, 7.49 g of ethyl 2-chlorobenzoate and 25 ml of dry ethanol, was dropwise added. After completion of the dropwise addition, the mixture was reacted for 1 hour under reflux.

After completion of the reaction, the reaction mixture was cooled and put into water, and the aqueous layer washed with methylene chloride was weakly acidified with hydrochloric acid and extracted with methylene chloride. The obtained extracted layer was dried over anhydrous sodium sulfate and concentrated under reduced pressure to obtain 1.6 g of β-(2-chlorophenyl)-β-hydroxy-α-(2-thienyl) acrylonitrile having a melting point of from 164 to 167° C. The NMR spectrum data of this compound were as follows.

$^1$H-NMR δppm (Solvent: CDCl$_3$/400 MHz)
6.54(s,1H), 7.18(dd,1H), 7.38–7.60(m,5H), 7.57(dd,1H)

2) 46 mg of triethylamine was added to a mixture comprising 0.12 g of β-(2-chlorophenyl)-β-hydroxy-α-(2-thienyl)acrylonitrile and 5 ml of dichloroethane, followed by cooling with ice. Then, a mixture comprising 54 mg of isobutylyl chloride and 2 ml of dichloroethane, was dropwise added. After completion of the dropwise addition, the mixture was returned to room temperature and reacted for 1.5 hours.

After completion of the reaction, the reaction mixture was put into water and extracted with methylene chloride. The extracted layer was washed with water, dried over anhydrous sodium sulfate and then concentrated under reduced pressure. The obtained residue was purified by silica gel column chromatography (developing solvent: ethyl acetate/n-hexane=1/4) to obtain 0.12 g of the desired product having a melting point of from 84 to 86° C. The NMR spectrum data of this product were as follows.

$^1$H-NMR δppm (Solvent: CDCl$_3$/400 MHz) 1.27(d,6H), 2.90(m,1H), 7.11(dd,1H), 7.33–7.40(m,2H), 7.45(d,2H), 7.52(d,1H), 7.65(dd,1H)

PREPARATION EXAMPLE 2

Preparation of α-(2,4-dichlorophenyl)-β-ethylsulfonyloxy-β-(2-trifluoromethylphenyl)acrylonitrile (after-mentioned Compound No. a-63)

1) A mixture comprising 3.7 g of 2-trifluoromethylbenzoyl chloride and 15 ml of toluene, were dropwise added with stirring at room temperature to a mixture comprising 3.0 g of 2,4-dichlorophenylacetonitrile, 45 ml of toluene, 1.63 g of triethylamine and 0.1 g of 4-dimethylaminopyridine. After completion of the dropwise addition, the mixture was reacted for 2 hours under reflux.

After completion of the reaction, the reaction mixture was cooled, put into water and extracted with methylene chloride. The obtained extracted layer was washed with water, dried over anhydrous sodium sulfate and then concentrated under reduced pressure to obtain 6.13 g of α-(2,4-dichlorophenyl)-β-(2-trifluoromethylphenyl)-β-(2-trifluoromethylbenzoyloxy)acrylonitrile. The NMR spectrum data of this compound were as follows.

$^1$H-NMR δppm (Solvent: $CDCl_3$/400 MHz) 7.21–7.45(m, 3H), 7.49–7.88(m,8H)

2) 6.13 g of α-(2,4-dichlorophenyl)-β-(2-trifluoromethylphenyl)-β-(2-trifluoromethylbenzoyloxy)acrylonitrile obtained in the above step, was, without purification, dissolved in 90 ml of ethanol. A mixture comprising 0.69 g of sodium hydroxide and 12 ml of water, was added thereto, and the mixture was reacted at room temperature for 2.5 hours.

After completion of the reaction, the reaction mixture was put into water, and the aqueous layer washed with methylene chloride was weakly acidified with hydrochloric acid and extracted with methylene chloride. The obtained extracted layer was washed with water, dried over anhydrous sodium sulfate and then concentrated under reduced pressure to obtain 2.5 g of α-(2,4-dichlorophenyl)-β-hydroxy-β-(2-trifluoromethylphenyl)acrylonitrile (after-mentioned Intermediate No. II-4) having a melting point of from 182 to 183° C. The NMR spectrum data of this compound were as follows.

$^1$H-NMR δppm (Solvent: $CDCl_3$/400 MHz) 5.81(s,1H), 7.38–7.48(m,2H), 7.54–7.65(m,1H), 7.66–7.82(m,4H)

3) 0.118 g of ethanesulfonyl chloride was added under cooling with ice to a mixture comprising 0.30 g of α-(2,4-dichlorophenyl)-β-hydroxy-β-(2-trifluoromethylphenyl)acrylonitrile, 7 ml of dichloroethane and 93 mg of triethylamine. Then, the mixture was returned to room temperature and reacted for 15 hours.

After completion of the reaction, the reaction mixture was washed with water, dried over anhydrous sodium sulfate and then concentrated under reduced pressure. The obtained residue was purified by silica gel column chromatography (developing solvent: ethyl acetate/n-hexane=1/4) to obtain 0.21 g of the desired product having a melting point of from 114 to 116° C. The NMR spectrum data of this product were as follows.

$^1$H-NMR δppm (Solvent: $CDCl_3$/400 MHz) 1.14(t,3H), 2.75–2.94(m,2H), 7.40(dd,1H), 7.47(d,1H), 7.57(d,1H), 7.71–7.78(m,2H), 7.85–7.89(m,2H)

PREPARATION EXAMPLE 3

Preparation of α-(2,4-dichlorophenyl)-β-methylsulfonyloxy-β-(2-trifluoromethylphenyl)-acrylonitrile (after-mentioned Compound No. a-55)

93 mg of triethylamine was added to a mixture comprising 0.30 g of α-(2,4-dichlorophenyl)-β-hydroxy-β-(2-trifluoromethylphenyl)acrylonitrile and 7 ml of dichloroethane. Then, 96 mg of methanesulfonyl chloride was added thereto, and the mixture was reacted for 17 hours at room temperature.

After completion of the reaction, the reaction mixture was washed with water, dried over anhydrous sodium sulfate and then concentrated under reduced pressure. The obtained residue was purified by silica gel column chromatography (developing solvent: ethyl acetate/n-hexane=1/6) to obtain 0.13 g of the desired oily product. The NMR spectrum data of this product were as follows.

$^1$H-NMR δppm (Solvent: $CDCl_3$/400 MHz) 2.68(s,3H), 7.38(d,1H), 7.46(d,1H), 7.54(s,1H), 7.70–7.77(m,2H), 7.84–7.89(m,2H)

PREPARATION EXAMPLE 4

Preparation of α-(2,4-dichlorophenyl)-β-(n-propylsulfonyloxy)-β-(2-trifluoromethylphenyl)-acrylonitrile (after-mentioned Compound No. a-67)

Process 1

93 mg of triethylamine was added to a mixture comprising 0.30 g of α-(2,4-dichlorophenyl)-β-hydroxy-β-(2-trifluoromethylphenyl)acrylonitrile and 7 ml of dichloroethane. Then, 0.13 g of n-propanesulfonyl chloride was added thereto, and the mixture was reacted for 15 hours at room temperature.

After completion of the reaction, the reaction mixture was washed with water, dried over anhydrous sodium sulfate and then concentrated under reduced pressure. The obtained residue was purified by silica gel column chromatography (developing solvent: ethyl acetate/n-hexane=1/4) to obtain 0.15 g of the desired oily product. The NMR spectrum data of this product were as follows.

$^1$H-NMR δppm (Solvent: $CDCl_3$/400 MHz) 0.87(t,3H), 1.52–1.64(m,2H), 2.65–2.73(m,1H), 2.79–2.86(m,1H), 7.40 (dd,1H), 7.47(d,1H), 7.57(d,1H), 7.71–7.78(m,2H), 7.85–7.89(m,2H)

PREPARATION EXAMPLE 5

Preparation of α-(2,4-dichlorophenyl)-β-(n-propylsulfonyloxy)-β-(2-trifluoromethylphenyl)-acrylonitrile (after-mentioned Compound No. a-67)

Process 2

2.22 g of triethylamine was added to a mixture comprising 5.60 g of α-(2,4-dichlorophenyl)-β-hydroxy-β-(2-trifluoromethylphenyl)acrylonitrile and 50 ml of dichloroethane. Then, a mixture comprising 2.90 g of n-propanesulfonyl chloride and 10 ml of dichloroethane, was dropwise added thereto. After completion of the dropwise addition, the mixture was reacted for 2 hours at room temperature.

After completion of the reaction, the reaction mixture was washed with water, dried over anhydrous sodium sulfate and then concentrated under reduced pressure. The obtained residue was purified by silica gel column chromatography (developing solvent: ethyl acetate/n-hexane=1/6) to obtain 2.8 g of the desired product having a melting point of from 95 to 96° C.

PREPARATION EXAMPLE 6

Preparation of α-(4-chlorophenyl)-β-(n-butylsulfonyloxy)-β-(2-trifluoromethylphenyl)acrylonitrile (after-mentioned Compound No. a-156)

1) A mixture comprising 6.19 g of 2-trifluoromethylbenzoyl chloride and 15 ml of toluene, was dropwise added with stirring at room temperature to a mixture comprising 3.0 g of 4-chlorophenylacetonitrile, 30 ml of toluene, 3.0 g of triethylamine and 0.1 g of 4-dimethylaminopyridine. After completion of the dropwise addition, the mixture was reacted for 8 hours under reflux.

After completion of the reaction, the reaction mixture was cooled, put into water and extracted with methylene chloride. The obtained extracted layer was washed with water, dried over anhydrous sodium sulfate and then concentrated under reduced pressure to obtain 3.08 g of α-(4-chlorophenyl)-β-(2-trifluoromethylphenyl)-β-(2-trifluoromethylbenzoyloxy)acrylonitrile.

2) 3.08 g of α-(4-chlorophenyl)-β-(2-trifluoromethylphenyl)-β-(2-trifluoromethylbenzoyloxy) acrylonitrile obtained in the above step was, without purification, dissolved in 40 ml of ethanol. A mixture comprising 0.50 g of sodium hydroxide and 10 ml of water was added thereto, and the mixture was reacted for 2 hours at room temperature.

After completion of the reaction, the reaction mixture was put into water, and the aqueous layer washed with methylene chloride was weakly acidified with hydrochloric acid and extracted with methylene chloride. The obtained extracted layer was washed with water, dried over anhydrous sodium sulfate and then concentrated under reduced pressure to obtain 1.68 g of α-(4-chlorophenyl)-β-hydroxy-β-(2-trifluoromethylphenyl)acrylonitrile (after-mentioned Intermediate No. II-2) having a melting point of from 146 to 148° C. The NMR spectrum data of this product were as follows.

$^1$H-NMR δppm (Solvent: CDCl$_3$/400 MHz) 7.41(d,2H), 7.58–7.68(m,5H), 7.75(m,1H)

3) 86 mg of triethylamine was added to a mixture comprising 0.25 g of α-(4-chlorophenyl)-β-hydroxy-β-(2-trifluoromethylphenyl)acrylonitrile and 8 ml of dichloroethane. Then, a mixture comprising 0.133 g of n-butanesulfonyl chloride and 2 ml of dichloroethane, was dropwise added thereto. After completion of the dropwise addition, the mixture was reacted for 15 hours at room temperature.

After completion of the reaction, the reaction mixture was washed with water, and the organic layer was dried over anhydrous sodium sulfate and then concentrated under reduced pressure. The obtained residue was purified by silica gel-column chromatography (developing solvent: ethyl acetate/n-hexane=1/6) to obtain 0.12 g of the desired product having a melting point of from 63 to 64° C. The NMR spectrum data of this product were as follows.

$^1$H-NMR δppm (Solvent: CDCl$_3$/400 MHz) 0.78(t,3H), 1.25(m,2H), 1.58(m,2H), 2.78(m,2H), 7.45(d,2H), 7.63(d,2H), 7.72(m,2H), 7.82(m,2H)

PREPARATION EXAMPLE 7

Preparation of α-(4-bromophenyl)-β-(ethylsulfonyloxy)-β-(2-trifluoromethylphenyl)acrylonitrile (after-mentioned Compound No. a-21)

1) A mixture comprising 17.55 g of 2-trifluoromethylbenzoyl chloride and 30 ml of toluene, was dropwise added with stirring at room temperature to a mixture comprising 15.0 g of 4-bromophenylacetonitrile, 120 ml of toluene, 8.52 g of triethylamine and 0.5 g of 4-dimethylaminopyridine. After completion of the dropwise addition, the mixture was reacted for 4 hours under reflux.

After completion of the reaction, the reaction mixture was cooled, put into water and extracted with methylene chloride. The obtained extracted layer was washed with water, dried over anhydrous sodium sulfate and then concentrated under reduced pressure to obtain 21.25 g of α-(4-bromophenyl)-β-(2-trifluoromethylphenyl)-β-(2-trifluoromethylbenzoyloxy)acrylonitrile.

2) 21.25 g of α-(4-bromophenyl)-β-(2-trifluoromethylphenyl)-β-(2-trifluoromethylbenzoyloxy) acrylonitrile obtained in the above step was, without purification, dissolved in 60 ml of ethanol. Then, a mixture comprising 2.36 g of sodium hydroxide and 15 ml of water, was added thereto, and the mixture was reacted for 2 hours at room temperature.

After completion of the reaction, the reaction mixture was put into water, and the aqueous layer washed with methylene chloride was weakly acidified with hydrochloric acid and extracted with methylene chloride. The obtained extracted layer was washed with water, dried over anhydrous sodium sulfate and then concentrated under reduced pressure to obtain 9.52 g of α-(4-bromophenyl)-β-hydroxy-β-(2-trifluoromethylphenyl)acrylonitrile (after-mentioned Intermediate No. II-3) having a melting point of from 168 to 173° C.

3) 91 mg of triethylamine was added to a mixture comprising 0.30 g of α-(4-bromophenyl)-β-hydroxy-β-(2-trifluoromethylphenyl)acrylonitrile and 8 ml of dichloroethane. Then, a mixture comprising 0.11 g of ethanesulfonyl chloride and 2 ml of dichloroethane, was dropwise added thereto. After completion of the dropwise addition, the mixture was reacted for 15 hours at room temperature.

After completion of the reaction, the reaction mixture was washed with water, and the organic layer was dried over anhydrous sodium sulfate and then concentrated under reduced pressure. The obtained residue was purified by silica gel column chromatography (developing solvent: ethyl acetate/n-hexane=1/4) to obtain 0.14 g of the desired product having a melting point of from 131 to 132° C. The NMR spectrum data of this product were as follows.

$^1$H-NMR δppm (Solvent: CDCl$_3$/400 MHz) 1.23(t,3H), 2.85(m,2H), 7.56–7.62(m,4H), 7.71(m,2H), 7.83(m,2H)

PREPARATION EXAMPLE 8

Preparation of α-(4-bromophenyl)-β-(n-propylsulfonyloxy)-β-(2-trifluoromethylphenyl) acrylonitrile (after-mentioned Compound No. a-22)

60 mg of triethylamine was added to a mixture comprising 0.20 g of α-(4-bromophenyl)-β-hydroxy-β-(2-trifluoromethylphenyl)acrylonitrile and 6 ml of dichloroethane. Then, a mixture comprising 77 mg of n-propanesulfonyl chloride and 2 ml of dichloroethane, was dropwise added thereto. After completion of the dropwise addition, the mixture was reacted for 15 hours at room temperature.

After completion of the reaction, the reaction mixture was washed with water, and the organic layer was dried over anhydrous sodium sulfate and then concentrated under reduced pressure. The obtained residue was purified by silica gel column chromatography (developing solvent: ethyl acetate/n-hexane=1/9) to obtain 0.10 g of the desired oily product. The NMR spectrum data of this product were as follows.

$^1$H-NMR δppm (Solvent: CDCl$_3$/400 MHz) 0.86(t,3H), 1.65(m,2H), 2.76(m,2H), 7.56–7.63(m,4H), 7.71(m,2H), 7.81(m,2H)

PREPARATION EXAMPLE 9

Preparation of α-(4-bromophenyl)-β-(n-butylsulfonyloxy)-β-(2-trifluoromethylphenyl)acrylonitrile (after-mentioned Compound No. a-23)

60 mg of triethylamine was added to a mixture comprising 0.20 g of α-(4-bromophenyl)-β-hydroxy-β-(2-trifluoromethylphenyl)acrylonitrile and 6 ml of dichloroethane. Then, a mixture comprising 85 mg of n-butanesulfonyl chloride and 2 ml of dichloroethane, was dropwise added thereto. After completion of the dropwise addition, the mixture was reacted for 15 hours at room temperature.

After completion of the reaction, the reaction mixture was washed with water, and the organic layer was dried over anhydrous sodium sulfate and then concentrated under reduced pressure. The obtained residue was purified by silica gel column chromatography (developing solvent: ethyl acetate/n-hexane=1/9) to obtain 70 mg of the desired oily product. The NMR spectrum data of this product were as follows.

$^1$H-NMR δppm (Solvent: CDCl$_3$/400 MHz) 0.78(t,3H), 1.23(m,2H), 1.59(m,2H), 2.78(m,2H), 7.57–7.63(m,4H), 7.71(m,2H), 7.82(m,2H)

PREPARATION EXAMPLE 10

Preparation of α-(4-chlorophenyl)-β-(dimethylthiocarbamoyloxy)-β-(2-trifluoromethylphenyl)-acrylonitrile (after-mentioned Compound No. a-316)

A mixed solution comprising 0.42 g of dimethylthiocarbamoyl chloride and 5 ml of acetonitrile, was dropwise added at room temperature to a mixed solution comprising 1.0 g of α-(4-chlorophenyl)-β-hydroxy-β-(2-trifluoromethylphenyl)acrylonitrile, 0.47 g of triethylamine, a catalytic amount of 4-dimethylaminopyridine and 20 ml of acetonitrile. After completion of the dropwise addition, the mixture was reacted for 2 hours at 50° C.

After completion of the reaction, acetonitrile was distilled off under reduced pressure. Ethyl acetate and water were added to the residue to carry out extraction. The organic layer was washed with water and a saturated sodium chloride aqueous solution and dried over anhydrous magnesium sulfate. Then, the solvent was distilled off, and the residue was purified by silica gel column chromatography (developing solvent: ethyl acetate/n-hexane=1/4) to obtain 0.82 g of the desired product having a melting point of 137.9° C. The NMR spectrum data of this product were as follows.

$^1$H-NMR δppm (Solvent: CDCl$_3$/400 MHz) 3.10(s,3H), 3.22(s,3H), 7.35–8.15(m,8H)

PREPARATION EXAMPLE 11

Preparation of α-(4-chlorophenyl)-β-(S-ethyldithiocarbonyloxy)-β-(2-trifluoromethylphenyl)-acrylonitrile (after-mentioned Compound No. a-306)

A mixed solution comprising 500 mg of α-(4-chlorophenyl)-β-hydroxy-β-(2-trifluoromethylphenyl)acrylonitrile and 2 ml of N,N-dimethylformamide were dropwise added under cooling with ice to a mixture comprising 68 mg of 60% sodium hydride and 10 ml of N,N-dimethylformamide. After completion of the dropwise addition, the mixture was gradually returned to room temperature, and stirring was continued until generation of hydrogen gas completed. Then, the mixture was again cooled with ice, and a mixed solution comprising 240 mg of ethyl chlorodithiocarbonate and 2 ml of N,N-dimethylformamide, was dropwise added. After completion of the dropwise addition, the mixture was reacted for 2 hours at room temperature.

After completion of the reaction, the reaction mixture was poured into 100 ml of ice water and then extracted with 150 ml of ethyl ether. The organic layer was washed with water and a saturated sodium chloride aqueous solution and dried over anhydrous magnesium sulfate. Then, the solvent was distilled off, and the residue was purified by silica gel column chromatography (developing solvent: ethyl acetate/n-hexane=1/9) to obtain 380 mg of the desired product having a refractive index $n_D^{27.2}$ of 1.5612. The NMR spectrum data of this product were as follows.

$^1$H-NMR δppm (Solvent: CDCl$_3$/400 MHz) 1.29(t,3H,J=7.80 Hz), 3.08(q,2H,J=7.80 Hz), 7.01–7.93(m,8H)

PREPARATION EXAMPLE 12

Preparation of α-(4-chlorophenyl)-β-(diethylaminosulfonyloxy)-β-(2-trifluoromethylphenyl)-acrylonitrile (after-mentioned Compound No. a-286)

0.18 g of triethylamine was added to a mixture comprising 0.3 g of α-(4-chlorophenyl)-β-hydroxy-β-(2-trifluoromethylphenyl)acrylonitrile and 5 ml of dichloroethane. Then, 0.27 g of diethylsulfamoyl chloride was added thereto, and the mixture was reacted for 3 hours under reflux.

After completion of the reaction, water was put into the reaction mixture and extracted with methylene chloride. The extracted organic layer was washed with water and dried over anhydrous sodium sulfate. Then, it was concentrated under reduced pressure, and the obtained residue was purified by silica gel column chromatography (developing solvent: ethyl acetate/n-hexane=15/85) to obtain 78 mg of the desired oily product. The NMR spectrum data of this product were as follows.

$^1$H-NMR δppm (Solvent: CDCl$_3$/400 MHz) 1.05(t,6H), 3.06(m,4H), 7.42(d,2H), 7.57(d,2H), 7.63–7.80(m,4H)

PREPARATION EXAMPLE 13

Preparation of α-(4-chlorophenyl)-β-(S-methyldithiocarbonyloxy)-β-(2-trifluoromethylphenyl)-acrylonitrile (after-mentioned Compound No. a-305)

A mixed solution comprising 800 mg of α-(4-chlorophenyl)-β-hydroxy-β-(2-trifluoromethylphenyl)acrylonitrile and 2 ml of N,N-dimethylformamide were dropwise added under cooling with ice to a mixture comprising 110 mg of 60% sodium hydride and 10 ml of N,N-dimethylformamide. After completion of the dropwise addition, the mixture was gradually returned to room temperature, and the stirring was continued until generation of hydrogen gas completed. Then, the mixture was cooled again with ice, and a mixed solution comprising 340 mg of methyl chlorodithiocarbonate and 2 ml of N,N-dimethylformamide, was dropwise added thereto. After completion of the dropwise addition, the mixture was reacted for 2 hours at room temperature.

After completion of the reaction, the reaction mixture was poured into 100 ml of ice water. Then, 150 ml of ethyl ether was added thereto for extraction. The organic layer was washed with water and a saturated sodium chloride aqueous solution and dried over anhydrous magnesium sulfate. Then, the solvent was distilled off, and the residue was purified by silica gel column chromatography (developing solvent: ethyl acetate/n-hexane=1/9) to obtain 610 mg of the desired product having a refractive index $n_D^{39.4}$ of 1.5930. The NMR spectrum data of this product were as follows.

$^1$H-NMR δppm (Solvent: CDCl$_3$/400 MHz) 2.47(s,3H), 2.53(s,3H), 7.07–7.99(m,8H)

PREPARATION EXAMPLE 14

Preparation of α-(4-chlorophenyl)-β-(dimethylaminosulfonyloxy)-β-(2-trifluoromethylphenyl)-acrylonitrile (after-mentioned Compound No. a-218)

1.25 g of triethylamine was added to a mixture comprising 2.0 g of α-(4-chlorophenyl)-β-hydroxy-β-(2-trifluoromethylphenyl)acrylonitrile and 40 ml of dichloroethane. Then, 1.68 g of dimethylsulfamoyl chloride was added thereto, and the mixture was reacted for 2 hours under reflux.

After completion of the reaction, water was added to the reaction mixture and extracted with methylene chloride. The extracted organic layer was washed with water and dried over anhydrous sodium sulfate. Then, it was concentrated under reduced pressure, and the obtained residue was purified by silica gel column chromatography (developing solvent: ethyl acetate/n-hexane=15/85) to obtain 2.50 g of the desired product having a melting point of from 110 to 112° C. The NMR spectrum data of this product were as follows.

$^1$H-NMR δppm (Solvent: CDCl$_3$/400 MHz) 2.66(s,6H), 7.43(d,2H), 7.60(d,2H), 7.67–7.82(m,4H)

PREPARATION EXAMPLE 15

Preparation of α-(4-chlorophenyl)-β-(ethyldithiooxy)-β-(2-trifluoromethylphenyl)acrylonitrile (after-mentioned Compound No. a-488)

1) 0.109 g of sulfur dichloride was added to a mixture comprising 0.25 g of α-(4-chlorophenyl)-β-hydroxy-β-(2-trifluoromethylphenyl)acrylonitrile and 10 ml of ethyl ether. Then, a mixture comprising 67 mg of pyridine and 10 ml of ethyl ether, was dropwise added thereto at −10° C., and the mixture was returned to room temperature and reacted for 3 hours.

After completion of the reaction, the reaction mixture was filtered, and the filtrate was concentrated under reduced pressure to obtain 0.30 g of α-(4-chlorophenyl)-β-chlorosulfenyloxy-β-(2-trifluoromethylphenyl)acrylonitrile.

2) 0.30 g of α-(4-chlorophenyl)-β-chlorosulfenyloxy-β-(2-trifluoromethylphenyl)acrylonitrile obtained in the above step was, without purification, dissolved in 10 ml of dichloroethane. Then, 58 mg of ethanethiol was added thereto, and then 94 mg of triethylamine was added thereto under cooling with ice. The mixture was returned to room temperature and reacted for 1 hour.

After completion of the reaction, water was added to the reaction mixture and extracted with methylene chloride. The extracted organic layer was washed with water, dried over anhydrous sodium sulfate and then concentrated under reduced pressure. The obtained residue was purified by silica gel column chromatography (developing solvent: ethyl acetate/n-hexane=15/85) to obtain 0.20 g of the desired oily product. The NMR spectrum data of this product were as follows.

$^1$H-NMR δppm (Solvent: CDCl$_3$/400 MHz) 1.24(t,3H), 2.62–2.79(m,2H), 7.12(d,1H), 7.43(d,2H), 7.49(t,1H), 7.60(d,2H), 7.74(d,1H)

Now, typical examples of the compound of the present invention of the above formula (I) will be shown in Tables 1-a, 1-b, 1-c and 1-d, and typical examples of the intermediate compound of the formula (II) will be shown in Table 2. These compounds can be synthesized in accordance with the above-described Preparation Examples or the above-described various methods for producing the compound of the present invention or its intermediate compound.

TABLE I-a $$(Ia)$$

| Comp. No. | $(R_3)_m$ | $R_1$ | $(R_2)_l$ | Physical Property (Melting point) |
|---|---|---|---|---|
| a-1 | phenyl | —SO$_2$CH$_2$CH$_3$ | 2-CF$_3$-phenyl | 74~75° C. |
| a-2 | phenyl | —SO$_2$N(CH$_3$)$_2$ | 2-CF$_3$-phenyl | 102~104° C. |
| a-3 | 2-Cl-phenyl | —COCH$_3$ | 2-Cl-phenyl | 98~100° C. |
| a-4 | 2-Cl-phenyl | —COCH$_3$ | 2,4-Cl$_2$-phenyl | Oily |
| a-5 | 2-Cl-phenyl | —CO(CH$_2$)$_2$CH$_3$ | 2-Cl-phenyl | Oily |

TABLE I-a-continued

| Comp. No. | (R₃)ₘ (phenyl) | R₁ | (R₂)ₗ Y (phenyl) | Physical Property (Melting point) |
|---|---|---|---|---|
| a-6 | 2-Cl phenyl | —CO(CH₂)₂CH₃ | 3,4-diCl phenyl | Oily |
| a-7 | 2-Cl phenyl | —COCH(CH₃)₂ | 2-Cl phenyl | Oily |
| a-8 | 2-Cl phenyl | —COC(CH₃)₃ | 2-Cl phenyl | 83–84° C. |
| a-9 | 2-Cl phenyl | —COC(CH₃)₃ | 3,4-diCl phenyl | Oily |
| a-10 | 4-Cl phenyl | —CO(CH₂)₂CH₃ | 2-CF₃ phenyl | Oily |

TABLE I-a-continued
(Ia)
| Comp. No. | (R₃)ₘ | R₁ | (R₂)ₗ Y | Physical Property (Melting point) |
|---|---|---|---|---|
| a-11 | 4-Cl-C₆H₄ | —COC(CH₃)₃ | 2-CF₃-C₆H₄ | 87~92° C. |
| a-12 | 4-Cl-C₆H₄ | —SO₂CH₃ | 2-CF₃-C₆H₄ | 104~108° C. |
| a-13 | 4-Cl-C₆H₄ | —SO₂CH₂CH₃ | 2-CF₃-C₆H₄ | 109~112° C. |
| a-14 | 4-Cl-C₆H₄ | —SO₂(CH₂)₂CH₃ | 2-CF₃-C₆H₄ | 86–89° C. |
| a-15 | 4-Br-C₆H₄ | —COCH₃ | 2-CF₃-C₆H₄ | |

TABLE I-a-continued

| Comp. No. | (R₃)ₘ | R₁ | (R₂)ₗ | Physical Property (Melting point) |
|---|---|---|---|---|
| a-16 | 4-Br-C₆H₄ | —COCH₂CH₃ | 2-CF₃-C₆H₄ | |
| a-17 | 4-Br-C₆H₄ | —CO(CH₂)₂CH₃ | 2-CF₃-C₆H₄ | |
| a-18 | 4-Br-C₆H₄ | —COCH(CH₃)₂ | 2-CF₃-C₆H₄ | |
| a-19 | 4-Br-C₆H₄ | —COC(CH₃)₃ | 2-CF₃-C₆H₄ | |
| a-20 | 4-Br-C₆H₄ | —SO₂CH₃ | 2-CF₃-C₆H₄ | 105~12° C. |

TABLE I-a-continued
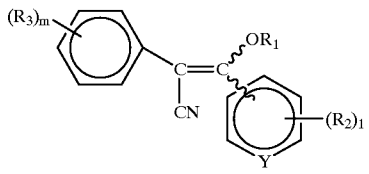
| Comp. No. | (R₃)ₘ | R₁ | (R₂)ₗ Y | Physical Property (Melting point) |
|---|---|---|---|---|
| a-21 |  | —SO₂CH₂CH₃ |  | 131~132° C. |
| a-22 |  | —SO₂(CH₂)₂CH₃ |  | Oily |
| a-23 |  | —SO₂(CH₂)₃CH₃ |  | Oily |
| a-24 |  | —COSCH₃ |  | Oily |
| a-25 |  | —COSCH₂CH₃ | 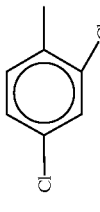 | Oily |

TABLE I-a-continued (Ia) [structure: (R3)m-phenyl-C(OR1)=C(CN)-phenyl-(R2)l]

| Comp. No. | (R3)m (phenyl) | R1 | (R2)l Y (phenyl) | Physical Property (Melting point) |
|---|---|---|---|---|
| a-26 | 2-methyl-4-chlorophenyl | —CH3 | 2-methyl-6-CF3-phenyl | |
| a-27 | 2-methyl-4-chlorophenyl | —CH2CH3 | 2-methyl-6-CF3-phenyl | 133~135° C. |
| a-28 | 2-methyl-4-chlorophenyl | —CH2CF3 | 2-methyl-6-CF3-phenyl | |
| a-29 | 2-methyl-4-chlorophenyl | —CH2OCH3 | 2-methyl-6-CF3-phenyl | E-isomer 99~103° C. |
| a-30 | 2-methyl-4-chlorophenyl | —COCH3 | 2-methyl-6-Cl-phenyl | 138~140° C. |

TABLE I-a-continued (Ia)

| Comp. No. | (R₃)ₘ ring | R₁ | (R₂)ₗ ring Y | Physical Property (Melting point) |
|---|---|---|---|---|
| a-31 | 2-methyl-4-chlorophenyl (Cl,Cl) | —COCH₃ | 2-CF₃-phenyl | 75~78° C. |
| a-32 | 2-methyl-4-chlorophenyl | —COCH₃ | 3-Cl-2-methylpyridine | |
| a-33 | 2-methyl-4-chlorophenyl | —COCH₃ | 3-CF₃-2-methylpyridine | |
| a-34 | 2-methyl-4-chlorophenyl | —COCH₂CH₃ | 3-Cl-2-methylphenyl | 93~94° C. |
| a-35 | 2-methyl-4-chlorophenyl | —COCH₂CH₃ | 3-CF₃-2-methylphenyl | |

TABLE I-a-continued

| Comp. No. | $(R_3)_m$ | $R_1$ | $(R_2)_l$ Y | Physical Property (Melting point) |
|---|---|---|---|---|
| a-36 | 2-CH₃, 4-Cl phenyl | —COCH₂CH₃ | 2-CH₃, 3-Cl pyridyl | |
| a-37 | 2-CH₃, 4-Cl phenyl | —COCH₂CH₃ | 2-F₃C, 3-CH₃ pyridyl | 59–60° C. |
| a-38 | 2-CH₃, 4-Cl phenyl | —CO(CH₂)₂CH₃ | 2-CH₃, 3-Cl phenyl | |
| a-39 | 2-CH₃, 4-Cl phenyl | —CO(CH₂)₂CH₃ | 2-F₃C, 3-CH₃ phenyl | Oily |
| a-40 | 2-CH₃, 4-Cl phenyl | —CO(CH₂)₂CH₃ | 2-CH₃, 3-Cl pyridyl | |

TABLE I-a-continued
| Comp. No. | (R₃)ₘ  | R₁ | 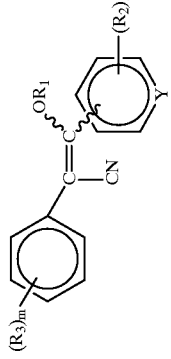 (R₂)ₗ | Physical Property (Melting point) |
|---|---|---|---|---|
| a-41 |  | —CO(CH₂)₂CH₃ |  | |
| a-42 |  | —COCH(CH₃)₂ |  | 92–94° C. |
| a-43 |  | —COCH(CH₃)₂ |  | Oily |
| a-44 | 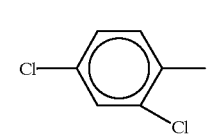 | —COCH(CH₃)₂ |  | |
| a-45 |  | —COCH(CH₃)₂ |  | |

TABLE I-a-continued
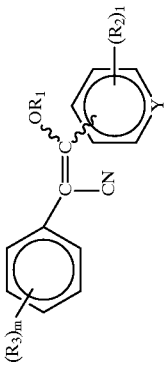
(Ia)
| Comp. No. | (R3)m | R1 | (R2)l Y | Physical Property (Melting point) |
|---|---|---|---|---|
| a-46 | 2,4-diCl-phenyl (with CH3) | —CO(CH2)3CH3 | 2-Cl-phenyl (with CH3) | Oily |
| a-47 | 2,4-diCl-phenyl (with CH3) | —COC(CH3)3 | 2-Cl-phenyl (with CH3) | Oily |
| a-48 | 2,4-diCl-phenyl (with CH3) | —COC(CH3)3 | 2-CF3-phenyl (with CH3) | Oily |
| a-49 | 2,4-diCl-phenyl (with CH3) | —COC(CH3)3 | 2-Cl-pyridyl (with CH3) | |
| a-50 | 2,4-diCl-phenyl (with CH3) | —COC(CH3)3 | 2-CF3-pyridyl (with CH3) | |

TABLE I-a-continued

| Comp. No. | (R₃)ₘ phenyl | R₁ | Y-ring (R₂)₁ | Physical Property (Melting point) |
|---|---|---|---|---|
| a-51 | 2-CH₃, 4-Cl phenyl | —CO(CH₂)₂Cl | 2-Cl phenyl | |
| a-52 | 2-CH₃, 4-Cl phenyl | —CO(CH₂)₂Cl | 2-CF₃ phenyl | |
| a-53 | 2-CH₃, 4-Cl phenyl | —SO₂CH₃ | 2-Cl phenyl | Z-isomer 121~123° C. |
| a-54 | 2-CH₃, 4-Cl phenyl | —SO₂CH₃ | 2-Cl phenyl | E-isomer 115~117° C. |
| a-55 | 2-CH₃, 4-Cl phenyl | —SO₂CH₃ | 2-CF₃ phenyl | Oily |

TABLE I-a-continued $$(Ia)$$

| Comp. No. | $(R_3)_m$ | $R_1$ | $(R_2)_l$ Y | Physical Property (Melting point) |
|---|---|---|---|---|
| a-56 | 2-methyl-4-chlorophenyl | —SO$_2$CH$_3$ | 2-methyl-(OCF$_3$)phenyl | |
| a-57 | 2-methyl-4-chlorophenyl | —SO$_2$CH$_3$ | 2-methyl-(NO$_2$)phenyl | Amorphous |
| a-58 | 2-methyl-4-chlorophenyl | —SO$_2$CH$_3$ | 2-methyl-(CN)phenyl | |
| a-59 | 2-methyl-4-chlorophenyl | —SO$_2$CH$_3$ | 2-methyl-(SO$_2$CH$_3$)phenyl | |
| a-60 | 2-methyl-4-chlorophenyl | —SO$_2$CH$_3$ | 3-chloro-2-methylpyridyl | |

TABLE I-a-continued

| Comp. No. | (R₃)ₘ | R₁ | (R₂)ₗ Y | Physical Property (Melting point) |
|---|---|---|---|---|
| a-61 | 2,4-diCl-phenyl | —SO₂CH₃ | 2-methyl-3-CF₃-pyridyl | |
| a-62 | 2,4-diCl-phenyl | —SO₂CH₂CH₃ | 2-methyl-3-Cl-phenyl | |
| a-63 | 2,4-diCl-phenyl | —SO₂CH₂CH₃ | 2-methyl-3-CF₃-phenyl | |
| a-64 | 2,4-diCl-phenyl | —SO₂CH₂CH₃ | 2-methyl-3-Cl-pyridyl | |
| a-65 | 2,4-diCl-phenyl | —SO₂CH₂CH₃ | 2-methyl-3-CF₃-pyridyl | E-isomer 114~116° C. |

TABLE I-a-continued

| Comp. No. | (R₃)ₘ (phenyl) | R₁ | Y-ring with (R₂)₁ | Physical Property (Melting point) |
|---|---|---|---|---|
| a-66 | 2-methyl-4-chloro-phenyl (wait: 2,4-di with methyl/Cl) | —SO₂(CH₂)₂CH₃ | 2-chlorophenyl | |
| a-67 | 2-methyl-4-chlorophenyl | —SO₂(CH₂)₂CH₃ | 2-(trifluoromethyl)phenyl | E-isomer 95–96° C. |
| a-68 | 2-methyl-4-chlorophenyl | —SO₂(CH₂)₂CH₃ | 3-chloro-2-pyridyl | |
| a-69 | 2-methyl-4-chlorophenyl | —SO₂(CH₂)₂CH₃ | 3-(trifluoromethyl)-2-pyridyl | |
| a-70 | 2-methyl-4-chlorophenyl | —SO₂CH(CH₃)₂ | 2-(trifluoromethyl)phenyl | 109–112° C. |

TABLE I-a-continued (Ia)

| Comp. No. | (R₃)ₘ | R₁ | Y / (R₂)ₗ | Physical Property (Melting point) |
|---|---|---|---|---|
| a-71 | 2-CH₃, 4-Cl phenyl | —SO₂(CH₂)₃CH₃ | 2-Cl phenyl | Oily |
| a-72 | 2-CH₃, 4-Cl phenyl | —SO₂(CH₂)₃CH₃ | 2-F₃C phenyl | |
| a-73 | 2-CH₃, 4-Cl phenyl | —SO₂(CH₂)₃CH₃ | 2-Cl pyridyl | |
| a-74 | 2-CH₃, 4-Cl phenyl | —SO₂(CH₂)₃CH₃ | 2-F₃C pyridyl | |
| a-75 | 2-CH₃, 4-Cl phenyl | —SO₂(CH₂)₄CH₃ | 2-F₃C phenyl | |

TABLE I-a-continued $$(Ia)$$

| Comp. No. | $(R_3)_m$ | $R_1$ | $(R_2)_l$ | Physical Property (Melting point) |
|---|---|---|---|---|
| a-76 | 2-Me, 4-Cl-C6H3 | —SO2(CH2)2Cl | 2-CF3-C6H4 | |
| a-77 | 2-Me, 4-Cl-C6H3 | —SO2CF3 | 2-Cl-C6H4 | Oily |
| a-78 | 2-Me, 4-Cl-C6H3 | —SO2CF3 | 2-CF3-C6H4 | $n_D^{48.2}$ 1.5430 |
| a-79 | 2-Me, 4-Cl-C6H3 | —SO2CH2CF3 | 2-CF3-C6H4 | |
| a-80 | 2-Me, 4-Cl-C6H3 | —SO2CH=CH2 | 2-CF3-C6H4 | 117~120° C. |

TABLE I-a-continued

| Comp. No. | (R₃)ₘ | R₁ | (R₂)ₗ Y | Physical Property (Melting point) |
|---|---|---|---|---|
| a-81 | 2,4-diCl-phenyl | —SO₂CH₂CH=CH₂ | 2-CF₃-phenyl | |
| a-82 | 2,4-diCl-phenyl | —SO₂-(4-OCF₃-phenyl) | 2-CF₃-phenyl | 165~167° C. |
| a-83 | 2-Cl,4-F-phenyl | —SO₂CH₃ | 2-CF₃-phenyl | Oily |
| a-84 | 2-Cl,4-F-phenyl | —SO₂CH₃ | 2-CF₃-phenyl | |
| a-85 | pentafluorophenyl | —SO₂CH₃ | 2-CF₃-phenyl | |

TABLE I-a-continued

| Comp. No. | (R₃)ₘ phenyl | R₁ | (R₂)ₗ phenyl with Y | Physical Property (Melting point) |
|---|---|---|---|---|
| a-86 | 4-F₃C-phenyl | —COCH₃ | 2-Cl-phenyl | |
| a-87 | 4-F₃C-phenyl | —COCH₃ | 2-CF₃-phenyl | |
| a-88 | 4-F₃C-phenyl | —COCH₂CH₃ | 2-Cl-phenyl | |
| a-89 | 4-F₃C-phenyl | —COCH₂CH₃ | 2-CF₃-phenyl | |
| a-90 | 4-F₃C-phenyl | —CO(CH₂)₂CH₃ | 2-Cl-phenyl | |

TABLE I-a-continued (Ia) [structure with (R3)m-phenyl, C(OR1)=C(CN)-phenyl-(R2)l-Y]

| Comp. No. | (R3)m [phenyl] | R1 | (R2)l [phenyl]-Y | Physical Property (Melting point) |
|---|---|---|---|---|
| a-91 | 4-F3C-phenyl | —CO(CH2)2CH3 | 2-F3C-phenyl | |
| a-92 | 4-F3C-phenyl | —COCH(CH3)2 | 2-Cl-phenyl | |
| a-93 | 4-F3C-phenyl | —COCH(CH3)2 | 2-F3C-phenyl | |
| a-94 | 4-F3C-phenyl | —COC(CH3)3 | 2-Cl-phenyl | |
| a-95 | 4-F3C-phenyl | —COC(CH3)3 | 2-F3C-phenyl | |

TABLE I-a-continued $$(Ia)$$

[Structure: (R3)m-phenyl-C(OR1)(CN)=...-phenyl-(R2)l-Y]

| Comp. No. | (R3)m-phenyl | R1 | (R2)l-Y phenyl | Physical Property (Melting point) |
|---|---|---|---|---|
| a-96 | 4-F3C-C6H4 | —SO2CH3 | 2-Cl-C6H4 | 121~124° C. |
| a-97 | 4-F3C-C6H4 | —SO2CH3 | 2-F3C-C6H4 | 115~125° C. |
| a-98 | 4-F3C-C6H4 | —SO2CH2CH3 | 2-Cl-C6H4 | |
| a-99 | 4-F3C-C6H4 | —SO2CH2CH3 | 2-F3C-C6H4 | 68~71° C. |
| a-100 | 4-F3C-C6H4 | —SO2(CH2)2CH3 | 2-Cl-C6H4 | |

TABLE I-a-continued

| Comp. No. | (R$_3$)$_m$ | R$_1$ | (R$_2$)$_l$ Y | Physical Property (Melting point) |
|---|---|---|---|---|
| a-101 | 4-CF$_3$-phenyl | —SO$_2$(CH$_2$)$_2$CH$_3$ | 2-CF$_3$-phenyl | |
| a-102 | 4-CF$_3$-phenyl | —SO$_2$(CH$_2$)$_2$CH$_3$ | 2-Cl-phenyl | |
| a-103 | 4-CF$_3$-phenyl | —SO$_2$(CH$_2$)$_3$CH$_3$ | 2-CF$_3$-phenyl | |
| a-104 | 3-Cl-4-CF$_3$-phenyl | —COCH$_3$ | 2-Cl-phenyl | |
| a-105 | 3-Cl-4-CF$_3$-phenyl | —COCH$_3$ | 2-CF$_3$-phenyl | |

TABLE I-a-continued (Ia)

| Comp. No. | (R₃)ₘ─⟨phenyl⟩ | R₁ | ⟨phenyl⟩─(R₂)ₗ Y | Physical Property (Melting point) |
|---|---|---|---|---|
| a-106 | 2-Cl-4-CF₃-phenyl | —COCH₂CH₃ | 2-Cl-phenyl | |
| a-107 | 2-Cl-4-CF₃-phenyl | —COCH₂CH₃ | 2-CF₃-phenyl | |
| a-108 | 2-Cl-4-CF₃-phenyl | —CO(CH₂)₂CH₃ | 2-Cl-phenyl | |
| a-109 | 2-Cl-4-CF₃-phenyl | —CO(CH₂)₂CH₃ | 2-CF₃-phenyl | |
| a-110 | 2-Cl-4-CF₃-phenyl | —COCH(CH₃)₂ | 2-Cl-phenyl | |

TABLE I-a-continued (Ia)

[Structure: (R3)m-phenyl-C(OR1)=C(CN)-phenyl-(R2)l-Y]

| Comp. No. | (R3)m [phenyl] | R1 | (R2)l [phenyl-Y] | Physical Property (Melting point) |
|---|---|---|---|---|
| a-111 | 2-Cl, 4-CF3 | —COCH(CH3)2 | 2-CF3 | |
| a-112 | 2-Cl, 4-CF3 | —COC(CH3)3 | 2-Cl | |
| a-113 | 2-Cl, 4-CF3 | —COC(CH3)3 | 2-CF3 | |
| a-114 | 2-Cl, 4-CF3 | —SO2CH3 | 2-Cl | |
| a-115 | 2-Cl, 4-CF3 | —SO2CH3 | 2-CF3 | |

TABLE I-a-continued

| Comp. No. | (R$_3$)$_m$ | R$_1$ | (R$_2$)$_l$ Y | Physical Property (Melting point) |
|---|---|---|---|---|
| a-116 | 2-Cl, 4-CF$_3$ | —SO$_2$CH$_2$CH$_3$ | 2-Cl | |
| a-117 | 2-Cl, 4-CF$_3$ | —SO$_2$CH$_2$CH$_3$ | 2-CF$_3$ | |
| a-118 | 2-Cl, 4-CF$_3$ | —SO$_2$(CH$_2$)$_2$CH$_3$ | 2-Cl | |
| a-119 | 2-Cl, 4-CF$_3$ | —SO$_2$(CH$_2$)$_2$CH$_3$ | 2-CF$_3$ | |
| a-120 | 2-Cl, 4-CF$_3$ | —SO$_2$(CH$_2$)$_3$CH$_3$ | 2-Cl | |

TABLE I-a-continued

| Comp. No. | (R3)m [ring] | R1 | (R2)l [ring] Y | Physical Property (Melting point) |
|---|---|---|---|---|
| a-121 | 2-Cl, 4-CF3-phenyl | —SO2(CH2)3CH3 | 2-CF3-phenyl | |
| a-122 | 2-F, 4-CF3-phenyl | —SO2CH3 | 2-CF3-phenyl | |
| a-123 | 4-O2N-phenyl | —COCH3 | 2-CF3-phenyl | 92–95° C. |
| a-124 | 4-O2N-phenyl | —COCH2CH3 | 2-CF3-phenyl | |
| a-125 | 4-O2N-phenyl | —CO(CH2)2CH3 | 2-CF3-phenyl | |

TABLE I-a-continued

| Comp. No. | (R₃)ₘ | R₁ | (R₂)ₗ | Physical Property (Melting point) |
|---|---|---|---|---|
| a-126 | 4-O₂N-C₆H₄ | —COCH(CH₃)₂ | 2-F₃C-C₆H₄ | |
| a-127 | 4-O₂N-C₆H₄ | —COC(CH₃)₃ | 2-F₃C-C₆H₄ | 125~128° C. |
| a-128 | 4-O₂N-C₆H₄ | —SO₂CH₃ | 2-F₃C-C₆H₄ | |
| a-129 | 4-O₂N-C₆H₄ | —SO₂CH₂CH₃ | 2-F₃C-C₆H₄ | |
| a-130 | 4-O₂N-C₆H₄ | —SO₂(CH₂)₂CH₃ | 2-F₃C-C₆H₄ | |

TABLE I-a-continued
(Ia)
| Comp. No. | $(R_3)_m$ | $R_1$ | $(R_2)_l$ Y | Physical Property (Melting point) |
|---|---|---|---|---|
| a-131 | 4-$O_2N$-C$_6H_4$ | —SO$_2$(CH$_2$)$_3$CH$_3$ | 2-F$_3$C-C$_6H_4$ | |
| a-132 | 2-NO$_2$-4-Cl-C$_6H_3$ | —COCH$_3$ | 2-F$_3$C-C$_6H_4$ | |
| a-133 | 2-NO$_2$-4-Cl-C$_6H_3$ | —COCH$_2$CH$_3$ | 2-F$_3$C-C$_6H_4$ | |
| a-134 | 2-NO$_2$-4-Cl-C$_6H_3$ | —CO(CH$_2$)$_2$CH$_3$ | 2-F$_3$C-C$_6H_4$ | |
| a-135 | 2-NO$_2$-4-Cl-C$_6H_3$ | —COCH(CH$_3$)$_2$ | 2-F$_3$C-C$_6H_4$ | |

TABLE I-a-continued

| Comp. No. | (R3)m | R1 | (R2)l Y | Physical Property (Melting point) |
|---|---|---|---|---|
| a-136 | 4-Cl, 2-NO2 phenyl | —COC(CH3)3 | 2-CF3 phenyl | 130~133° C. |
| a-137 | 4-Cl, 2-NO2 phenyl | —SO2CH3 | 2-CF3 phenyl | |
| a-138 | 4-Cl, 2-NO2 phenyl | —SO2CH2CH3 | 2-CF3 phenyl | |
| a-139 | 4-Cl, 2-NO2 phenyl | —SO2(CH2)2CH3 | 2-CF3 phenyl | |
| a-140 | 4-Cl, 2-NO2 phenyl | —SO2(CH2)3CH3 | 2-CF3 phenyl | |

TABLE I-a-continued

| Comp. No. | (R₃)ₘ | R₁ | (R₂)ₗ Y | Physical Property (Melting point) |
|---|---|---|---|---|
| a-141 | 4-NO₂, 3-Cl-phenyl | —COCH₃ | 2-CF₃-phenyl | |
| a-142 | 4-NO₂, 3-Cl-phenyl | —COCH₂CH₃ | 2-CF₃-phenyl | |
| a-143 | 4-NO₂, 3-Cl-phenyl | —CO(CH₂)₂CH₃ | 2-CF₃-phenyl | |
| a-144 | 4-NO₂, 3-Cl-phenyl | —COCH(CH₃)₂ | 2-CF₃-phenyl | |
| a-145 | 4-NO₂, 3-Cl-phenyl | —COC(CH₃)₃ | 2-CF₃-phenyl | |

TABLE I-a-continued (Ia)

| Comp. No. | (R₃)ₘ phenyl | R₁ | (R₂)ₗ phenyl (Y) | Physical Property (Melting point) |
|---|---|---|---|---|
| a-146 | 2-Cl-4-NO₂-methylphenyl | —SO₂CH₃ | 2-CF₃-methylphenyl | |
| a-147 | 2-Cl-4-NO₂-methylphenyl | —SO₂CH₂CH₃ | 2-CF₃-methylphenyl | |
| a-148 | 2-Cl-4-NO₂-methylphenyl | —SO₂(CH₂)₂CH₃ | 2-CF₃-methylphenyl | |
| a-149 | 2-Cl-4-NO₂-methylphenyl | —SO₂(CH₂)₃CH₃ | 2-CF₃-methylphenyl | |
| a-150 | 2-Cl-4-H₃CS-methylphenyl | —COC(CH₃)₃ | 2-CF₃-methylphenyl | $n_D^{30.8}$ 1.5432 |

TABLE I-a-continued

| Comp. No. | (R3)m | R1 | (R2)l | Physical Property (Melting point) |
|---|---|---|---|---|
| a-151 | 3-Cl-4-CH3-5-(H3CO2S)-phenyl | —SO2CH3 | 2-CH3-3-CF3-phenyl | 147.3° C. |
| a-152 | 3-Cl-4-CH3-phenoxy-phenyl | —COC(CH3)3 | 2-CH3-3-CF3-phenyl | $n_D^{30.8}$ 1.5336 |
| a-153 | 4-Cl-2-CH3-phenyl | —COCH3 | 2-CH3-3-CF3-pyridyl | Oily |
| a-154 | 4-Cl-2-CH3-phenyl | —SO2N(CH3)2 | 2-CH3-3-CF3-pyridyl |  |
| a-155 | 2-CH3-4,5-diCl-phenyl | —COC6H5 | 2-CH3-3-CF3-phenyl |  |

TABLE I-a-continued

| Comp. No. | $(R_3)_m$ | $R_1$ | $(R_2)_l$ Y | Physical Property (Melting point) |
|---|---|---|---|---|
| a-156 | 4-Cl-C6H4 | —SO2(CH2)3CH3 | 2-CF3-C6H4 | 63–64° C. |
| a-157 | 4-Cl-C6H4 | —CS2C≡CH | 2-CF3-C6H4 | |
| a-158 | 2-Cl-C6H4 | —SO2CH3 | 2-CF3-C6H4 | 90–93° C. |
| a-159 | 3-Cl-C6H4 | —SO2CH3 | 2-CF3-C6H4 | Oily |
| a-160 | 4-Cl-C6H4 | —COCH3 | 2-CF3-C6H4 | 77–80° C. |

TABLE I-a-continued

| Comp. No. | (R₃)ₘ | R₁ | (R₂)ₗ | Physical Property (Melting point) |
|---|---|---|---|---|
| a-161 | 4-Cl-C₆H₄ | —COCH₂CH₃ | 2-CF₃-C₆H₄ | 65–69° C. |
| a-162 | 4-Cl-C₆H₄ | —COCH(CH₃)₂ | 2-CF₃-C₆H₄ | 83–84° C. |
| a-163 | 4-Cl-C₆H₄ | —SO₂(CH₂)₄CH₃ | 2-CF₃-C₆H₄ | Oily |
| a-164 | 4-Cl-C₆H₄ | —SO₂CH=CH₂ | 2-CF₃-C₆H₄ | 73–76° C. |
| a-165 | 4-Cl-C₆H₄ | —SO₂CF₃ | 2-CF₃-C₆H₄ | Oily |

TABLE I-a-continued

| Comp. No. | (R$_3$)$_m$ | R$_1$ | (R$_2$)$_l$ Y | Physical Property (Melting point) |
|---|---|---|---|---|
| a-166 | 4-Cl-C$_6$H$_4$ | —SO$_2$CH$_2$CF$_3$ | 2-CF$_3$-C$_6$H$_4$ | 102~105° C. |
| a-167 | 4-Cl-C$_6$H$_4$ | —SO$_2$(CH$_2$)$_3$Cl | 2-CF$_3$-C$_6$H$_4$ | Oily |
| a-168 | 4-Cl-C$_6$H$_4$ | —SO$_2$CH$_3$ | 2-CF$_3$-C$_6$H$_4$ | 95~100° C. |
| a-169 | 4-Cl-C$_6$H$_4$ | —SO$_2$CH$_3$ | 2,6-F$_2$-C$_6$H$_3$ | 121~123° C. |
| a-170 | 4-Cl-C$_6$H$_4$ | —SO$_2$CH$_3$ | 2-NO$_2$-C$_6$H$_4$ | Oily |

TABLE I-a-continued

| Comp. No. | (R₃)ₘ | R₁ | (R₂)ₗ Y | Physical Property (Melting point) |
|---|---|---|---|---|
| a-171 | 4-Cl-phenyl | —SO₂CH₃ | 2-Cl-3-methylpyridinyl | $n_D^{23.8}$ 1.5991 |
| a-172 | 4-Cl-phenyl | —SO₂CH₃ | 3-methyl-4-CF₃-pyridinyl | 101.9° C. |
| a-173 | 4-F-phenyl | —SO₂N(CH₃)CH₂CH₃ | 2-CF₃-phenyl | 77–79° C. |
| a-174 | 4-F-phenyl | —COCH₃ | 2-CF₃-phenyl | |
| a-175 | 4-F-phenyl | —SO₂CH₃ | 2-CF₃-phenyl | 95–98° C. |

TABLE I-a-continued

| Comp. No. | (R₃)ₘ | R₁ | (R₂)ₗ Y | Physical Property (Melting point) |
|---|---|---|---|---|
| a-176 | 4-F-C₆H₄ | —SO₂CH₂CH₃ | 2-CF₃-C₆H₄ | 99~102° C. |
| a-177 | 4-F-C₆H₄ | —SO₂(CH₂)₂CH₃ | 2-CF₃-C₆H₄ | 101~102° C. |
| a-178 | 4-F-C₆H₄ | —SO₂(CH₂)₃CH₃ | 2-CF₃-C₆H₄ | 83~85° C. |
| a-179 | 4-Br-C₆H₄ | —COSCH₃ | 2-CF₃-C₆H₄ | Oily |
| a-180 | 4-Br-C₆H₄ | —SO₂(CH₂)₄CH₃ | 2-CF₃-C₆H₄ | Oily |

TABLE I-a-continued
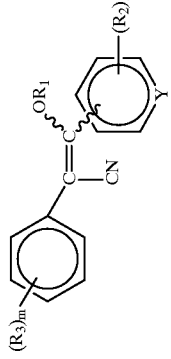
(Ia)
| Comp. No. | (R₃)ₘ | R₁ | (R₂)ₗ Y | Physical Property (Melting point) |
|---|---|---|---|---|
| a-181 | 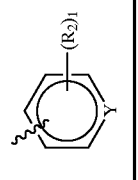 | —COSCH₂CH₃ | 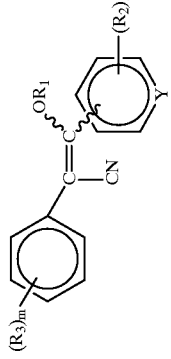 | 65~68° C. |
| a-182 |  | —COCH₃ | 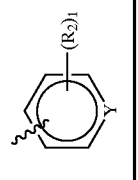 | |
| a-183 |  | —SO₂CH₃ | 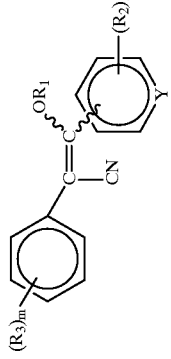 | 112~113° C. |
| a-184 | 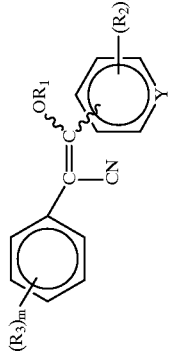 | —SO₂CH₂CH₃ | 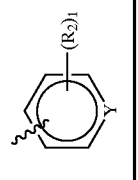 | 126~128° C. |
| a-185 | 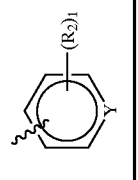 | —SO₂(CH₂)₂CH₃ | 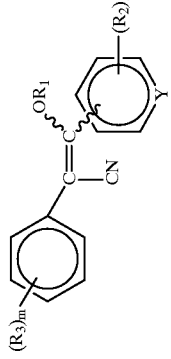 | 106~107° C. |

TABLE I-a-continued

| Comp. No. | (R3)m | R1 | (R2)l Y | Physical Property (Melting point) |
|---|---|---|---|---|
| a-186 | 4-I-phenyl | —SO2(CH2)3CH3 | 2-CF3-phenyl | 73~75° C. |
| a-187 | 2,4-diCl-phenyl | —SO2(CH2)3Cl | 2-CF3-phenyl | Oily |
| a-188 | 2,4-diCl-phenyl | —SO2(CH2)2CH3 | 2-CF3-phenyl | Z-isomer 75~77° C. |
| a-189 | 2,4-diCl-phenyl | —SO2CH2CH3 | 2-CF3-phenyl | Z-isomer Oily |
| a-190 | 3,4-diCl-phenyl | —SO2CH3 | 2-CF3-phenyl | 96~98° C. |

TABLE I-a-continued (Ia)

| Comp. No. | (R₃)ₘ | R₁ | (R₂)ₗ | Physical Property (Melting point) |
|---|---|---|---|---|
| a-191 | 2-F, 6-F phenyl (2-methyl, 6-F) | —SO₂CH₂CH₃ | 2-CF₃ phenyl (with methyl) | 84.2° C. |
| a-192 | 2-methyl, 3-F, 4-Cl phenyl | —SO₂N(CH₃)CH₂CH₃ | 2-CF₃ phenyl (with methyl) | |
| a-193 | 2-methyl, 3-F, 4-Cl phenyl | —COCH₃ | 2-CF₃ phenyl (with methyl) | |
| a-194 | 2-methyl, 3-F, 4-Cl phenyl | —SO₂CH₃ | 2-CF₃ phenyl (with methyl) | 81~84° C. |
| a-195 | 2-methyl, 3-F, 4-Cl phenyl | —SO₂CH₂CH₃ | 2-CF₃ phenyl (with methyl) | 122~125° C. |

TABLE I-a-continued (Ia)

| Comp. No. | (R₃)ₘ─⟨phenyl⟩ | R₁ | ─⟨phenyl⟩─(R₂)ₗ Y | Physical Property (Melting point) |
|---|---|---|---|---|
| a-196 | 3-F, 4-Cl | —SO₂(CH₂)₂CH₃ | 2-CF₃ | 65~66° C. |
| a-197 | 3-F, 4-Cl | —SO₂(CH₂)₃CH₃ | 2-CF₃ | Oily |
| a-198 | 3-F, 4-Cl | —SO₂N(CH₂)₂CH₃ CH₃ | 2-CF₃ | |
| a-199 | 3-Cl, 4-F | —COCH₃ | 2-CF₃ | |
| a-200 | 3-Cl, 4-F | —SO₂CH₂CH₃ | 2-CF₃ | 103~105° C. |

TABLE I-a-continued (Ia)

| Comp. No. | (R₃)ₘ─⟨⟩ | R₁ | ─⟨⟩─(R₂)₁ Y | Physical Property (Melting point) |
|---|---|---|---|---|
| a-201 | 2-Cl, 4-F-phenyl | —SO₂(CH₂)₂CH₃ | 2-CF₃-phenyl | 80–82° C. |
| a-202 | 2-Cl, 4-F-phenyl | —SO₂(CH₂)₃CH₃ | 2-CF₃-phenyl | 50–52° C. |
| a-203 | 4-CH₃-phenyl | —SO₂CH₃ | 2-CF₃-phenyl | 133–136° C. |
| a-204 | 4-(CH₃)₂CH-phenyl | —SO₂CH₃ | 2-CF₃-phenyl | 88–91° C. |
| a-205 | 4-(CH₃)₃C-phenyl | —S-phenyl | 2-CF₃-phenyl | |

TABLE I-a-continued

| Comp. No. | (R$_3$)$_m$ | R$_1$ | (R$_2$)$_l$ Y | Physical Property (Melting point) |
|---|---|---|---|---|
| a-206 | 4-(H$_3$C)$_3$C-C$_6$H$_4$ | —SO$_2$CH$_3$ | 2-CF$_3$-C$_6$H$_4$ | 101~103° C. |
| a-207 | 4-(H$_3$C)$_3$C-C$_6$H$_4$ | —SO$_2$(CH$_2$)$_2$CH$_3$ | 2-CF$_3$-C$_6$H$_4$ | 68~70° C. |
| a-208 | 4-H$_3$CO-C$_6$H$_4$ | —SO$_2$CH$_3$ | 2-CF$_3$-C$_6$H$_4$ | 127~130° C. |
| a-209 | 4-Cl-C$_6$H$_4$ | —CH$_2$CH$_3$ | 2-CF$_3$-C$_6$H$_4$ | 105~107° C. |
| a-210 | 4-Cl-C$_6$H$_4$ | —CH$_2$CH$_2$Cl | 2-CF$_3$-C$_6$H$_4$ | 71~73° C. |

TABLE I-a-continued (Ia) structure with (R3)m-phenyl-C(OR1)=C(CN)-phenyl-(R2)l, Y

| Comp. No. | (R3)m-phenyl | R1 | (R2)l-phenyl-Y | Physical Property (Melting point) |
|---|---|---|---|---|
| a-211 | 4-Cl-phenyl | —CH₂OCH₃ | 2-CF₃-phenyl | 68~72° C. |
| a-212 | 4-Cl-phenyl | —CH₂OCH₂CH₃ | 2-CF₃-phenyl | Oily |
| a-213 | 4-Cl-phenyl | —CH₂CH₂OCH₃ | 2-CF₃-phenyl | |
| a-214 | 4-Cl-phenyl | —SO₂CH(CH₃)₂ | 2-CF₃-phenyl | 82~84° C. |
| a-215 | 4-Cl-phenyl | —SO₂CH₂CH(CH₃)₂ | 2-CF₃-phenyl | 80~83° C. |

TABLE I-a-continued

| Comp. No. | (R₃)ₘ | R₁ | (R₂)ₗ | Physical Property (Melting point) |
|---|---|---|---|---|
| a-216 | 4-Cl-C₆H₄ | —SO₂CH(CH₃)CH₂CH₃ | 2-CF₃-C₆H₄ | |
| a-217 | 4-Cl-C₆H₄ | —SO₂C(CH₃)₃ | 2-CF₃-C₆H₄ | |
| a-218 | 4-Cl-C₆H₄ | —SO₂N(CH₃)₂ | 2-CF₃-C₆H₄ | 110–112° C. |
| a-219 | 4-F-C₆H₄ | —SO₂N(CH₃)₂ | 2-CF₃-C₆H₄ | 84–86° C. |
| a-220 | 4-Br-C₆H₄ | —SO₂N(CH₃)₂ | 2-CF₃-C₆H₄ | 120–121° C. |

TABLE I-a-continued (Ia)

| Comp. No. | (R₃)ₘ | R₁ | (R₂)₁ | Physical Property (Melting point) |
|---|---|---|---|---|
| a-221 | 4-I-phenyl | —SO₂N(CH₃)₂ | 2-CF₃-phenyl | 126~127° C. |
| a-222 | 2-Cl,4-Cl-phenyl | —CH₂CH₂Cl | 2-CF₃-phenyl | 88~90° C. |
| a-223 | 2-Cl,4-Cl-phenyl | —CH₂OCH₂CH₃ | 2-CF₃-phenyl | E-isomer 86~88° C. |
| a-224 | 2-Cl,4-Cl-phenyl | —CH₂OCH₂CH₃ | 2-CF₃-phenyl | Z-isomer 77~80° C. |
| a-225 | 2-Cl,4-Cl-phenyl | —CH₂CH₂OCH₃ | 2-CF₃-phenyl | 111~113° C. |

TABLE I-a-continued (Ia) structure with (R₃)ₘ-phenyl-C(OR₁)=C(CN)-Y-phenyl-(R₂)ₗ

| Comp. No. | (R₃)ₘ | R₁ | Y-ring (R₂)ₗ | Physical Property (Melting point) |
|---|---|---|---|---|
| a-226 | 2-CH₃, 4-Cl phenyl | —CH₂SCH₃ | 2-CH₃, 6-CF₃ phenyl | E-isomer 87–92° C. |
| a-227 | 2-CH₃, 4-Cl phenyl | —SO₂CH₂CH(CH₃)₂ | 2-CH₃, 6-CF₃ phenyl | Oily |
| a-228 | 2-CH₃, 4-Cl phenyl | —SO₂CH(CH₃)CH₂CH₃ | 2-CH₃, 6-CF₃ phenyl | |
| a-229 | 2-CH₃, 4-Cl phenyl | —SO₂C(CH₃)₃ | 2-CH₃, 6-CF₃ phenyl | |
| a-230 | 2-CH₃, 4-Cl phenyl | —SO₂N(CH₃)₂ | 2-CH₃, 6-CF₃ phenyl | 137–141° C. |

TABLE I-a-continued

| Comp. No. | (R₃)ₘ | R₁ | (R₂)ₗ | Physical Property (Melting point) |
|---|---|---|---|---|
| a-231 | 4-NC-C₆H₄ | —SO₂(CH₂)₂CH₃ | 2-CF₃-C₆H₄ | 113.1° C. |
| a-232 | C₆H₅ | —SO₂CH₃ | 2-CF₃-C₆H₄ | 95.3° C. |
| a-233 | 2-Cl-C₆H₄ | —SO₂CH₂CH₃ | 2-CF₃-C₆H₄ | Oily |
| a-234 | 4-Cl-C₆H₄ | —CH₃ | 2-CF₃-C₆H₄ | 100–101° C. |
| a-235 | 4-Cl-C₆H₄ | -(CH₂)₂CH₃ | 2-CF₃-C₆H₄ | Oily |

TABLE I-a-continued

| Comp. No. | (R₃)ₘ-phenyl | R₁ | (R₂)ₗ-Y-ring | Physical Property (Melting point) |
|---|---|---|---|---|
| a-236 | 4-Cl-C₆H₄ | —CH(CH₃)₂ | 2-CF₃-C₆H₄ | 81~82° C. |
| a-237 | 4-Cl-C₆H₄ | —(CH₂)₃CH₃ | 2-CF₃-C₆H₄ | Oily |
| a-238 | 4-Cl-C₆H₄ | —CH₂CH₂F | 2-CF₃-C₆H₄ | Oily |
| a-239 | 4-Cl-C₆H₄ | —CH₂CF₃ | 2-CF₃-C₆H₄ | Oily |
| a-240 | 4-Cl-C₆H₄ | —CH₂CH=CH₂ | 2-CF₃-C₆H₄ | Oily |

TABLE I-a-continued

| Comp. No. | (R₃)ₘ structure | R₁ | (R₂)₁ structure | Physical Property (Melting point) |
|---|---|---|---|---|
| a-241 | 4-Cl-C₆H₄ | —CH₂C(Cl)=CH₂ | 2-CF₃-C₆H₄ | |
| a-242 | 4-Cl-C₆H₄ | —CH₂C(Cl)=CHCl | 2-CF₃-C₆H₄ | |
| a-243 | 4-Cl-C₆H₄ | —CH₂C≡CH | 2-CF₃-C₆H₄ | |
| a-244 | 4-Cl-C₆H₄ | —COCH₂OCH₃ | 2-CF₃-C₆H₄ | Oily |
| a-245 | 4-Cl-C₆H₄ | —COSCH₂CH₃ | 2-CF₃-C₆H₄ | Oily |

TABLE I-a-continued (Ia)

| Comp. No. | (R₃)ₘ | R₁ | (R₂)ₗ Y | Physical Property (Melting point) |
|---|---|---|---|---|
| a-246 | 4-Cl-C₆H₄ | —COCH₂CH=CH₂ | 2-CF₃-C₆H₄ | |
| a-247 | 4-Cl-C₆H₄ | —COCH₂C(Cl)=CH₂ | 2-CF₃-C₆H₄ | |
| a-248 | 4-Cl-C₆H₄ | —COCH₂C≡CH | 2-CF₃-C₆H₄ | |
| a-249 | 4-Cl-C₆H₄ | —COCH₂C≡CCl | 2-CF₃-C₆H₄ | |
| a-250 | 4-Cl-C₆H₄ | —CO₂CH₃ | 2-CF₃-C₆H₄ | 60–63° C. |

TABLE I-a-continued

| Comp. No. | (R₃)ₘ | R₁ | (R₂)ₗ Y | Physical Property (Melting point) |
|---|---|---|---|---|
| a-251 | 4-Cl-C₆H₄ | —CO₂CH₂CH₃ | 2-CF₃-C₆H₄ | Oily |
| a-252 | 4-Cl-C₆H₄ | —CO₂CH₂CF₃ | 2-CF₃-C₆H₄ | |
| a-253 | 4-Cl-C₆H₄ | —CONH(CH₂)₂CH₃ | 2-CF₃-C₆H₄ | |
| a-254 | 4-Cl-C₆H₄ | —CON(CH₃)₂ | 2-CF₃-C₆H₄ | 58~61° C. |
| a-255 | 4-Cl-C₆H₄ | —CO—C₆H₅ (as drawn) | 2-CF₃-C₆H₄ | 135~138° C. |

TABLE I-a-continued (Ia)

| Comp. No. | $(R_3)_m$ | $R_1$ | $(R_2)_l$ Y | Physical Property (Melting point) |
|---|---|---|---|---|
| a-256 | 4-Cl-C6H4 | 2-Cl-C6H4 | 2-CF3-C6H4 | 109~111° C. |
| a-257 | 4-Cl-C6H4 | 3-Cl-C6H4 | 2-CF3-C6H4 | Oily |
| a-258 | 4-Cl-C6H4 | 4-Cl-C6H4 | 2-CF3-C6H4 | 106~109° C. |
| a-259 | 4-Cl-C6H4 | 3,4-di-Cl-C6H3 | 2-CF3-C6H4 | — |
| a-260 | 4-Cl-C6H4 | 4-Cl-3-CH3-C6H3 | 2-CF3-C6H4 | 123~124° C. |

TABLE I-a-continued (Ia)

| Comp. No. | (R₃)ₘ | R₁ | (R₂)₁ Y | Physical Property (Melting point) |
|---|---|---|---|---|
| a-261 | 4-Cl-C₆H₄ | 4-CH₃-C₆H₄-CO- | 2-CF₃-C₆H₄ | 124~127° C. |
| a-262 | 4-Cl-C₆H₄ | 4-OCH₃-C₆H₄-CO- | 2-CF₃-C₆H₄ | 110~113° C. |
| a-263 | 4-Cl-C₆H₄ | C₆H₅-CO₂- | 2-CF₃-C₆H₄ | Oily |
| a-264 | 4-Cl-C₆H₄ | 4-NO₂-C₆H₄-CO₂- | 2-CF₃-C₆H₄ | |
| a-265 | 4-Cl-C₆H₄ | 4-SO₂CH₃-C₆H₄-CO₂- | 2-CF₃-C₆H₄ | |

TABLE I-a-continued (Ia)

| Comp. No. | (R₃)ₘ | R₁ | (R₂)ₗ Y | Physical Property (Melting point) |
|---|---|---|---|---|
| a-266 | 4-Cl-C₆H₄ | —COS—C₆H₅ | 2-CF₃-C₆H₄ | |
| a-267 | 4-Cl-C₆H₄ | —COCH₂—C₆H₅ | 2-CF₃-C₆H₄ | 85–87° C. |
| a-268 | 4-Cl-C₆H₄ | —COCH₂—(4-Cl-C₆H₄) | 2-CF₃-C₆H₄ | |
| a-269 | 4-Cl-C₆H₄ | —COCH₂—(4-CH₃-C₆H₄) | 2-CF₃-C₆H₄ | |
| a-270 | 4-Cl-C₆H₄ | —COSCH₂—C₆H₅ | 2-CF₃-C₆H₄ | |

TABLE I-a-continued

| Comp. No. | (R3)m | R1 | (R2)l Y | Physical Property (Melting point) |
|---|---|---|---|---|
| a-271 | 4-Cl-C6H4 | pyrrolidine-CON | 2-CF3-C6H4 | |
| a-272 | 4-Cl-C6H4 | piperidine-CON | 2-CF3-C6H4 | |
| a-273 | 4-Cl-C6H4 | morpholine-CON | 2-CF3-C6H4 | |
| a-274 | 4-Cl-C6H4 | —SCH3 | 2-CF3-C6H4 | |
| a-275 | 4-Cl-C6H4 | —SOCH3 | 2-CF3-C6H4 | Oily |

TABLE I-a-continued

| Comp. No. | $(R_3)_m$ | $R_1$ | $(R_2)_l$ | Physical Property (Melting point) |
|---|---|---|---|---|
| a-276 | 4-Cl-C6H4 | —SOCH2CH3 | 2-CF3-C6H4 | |
| a-277 | 4-Cl-C6H4 | —SO2CH3 | 2-OCH3-C6H4 | 153.9° C. |
| a-278 | 4-Cl-C6H4 | —SO2CH3 | 2-OCF3-C6H4 | Oily |
| a-279 | 4-Cl-C6H4 | —SO2CH2OCH3 | 2-CF3-C6H4 | |
| a-280 | 4-Cl-C6H4 | —SO2CH2C(Cl)=CH2 | 2-CF3-C6H4 | |

TABLE I-a-continued

| Comp. No. | $(R_3)_m$ | $R_1$ | $(R_2)_l$ Y | Physical Property (Melting point) |
|---|---|---|---|---|
| a-281 | 4-Cl-C6H4 | —SO2CH2C≡CCl | 2-CF3-C6H4 | |
| a-282 | 4-Cl-C6H4 | —SO2OCH2CH3 | 2-CF3-C6H4 | 98~101° C. |
| a-283 | 4-Cl-C6H4 | —SO2SCH2CH3 | 2-CF3-C6H4 | |
| a-284 | 4-Cl-C6H4 | —SO2NH(CH2)2CH3 | 2-CF3-C6H4 | |
| a-285 | 4-Cl-C6H4 | —SO2NHC(CH3)3 | 2-CF3-C6H4 | |

TABLE I-a-continued (Ia)

| Comp. No. | (R$_3$)$_m$ | R$_1$ | (R$_2$)$_l$ Y | Physical Property (Melting point) |
|---|---|---|---|---|
| a-286 | 4-Cl-phenyl | —SO$_2$N(CH$_2$CH$_3$)$_2$ | 2-CF$_3$-phenyl | Oily |
| a-287 | 4-Cl-phenyl | —SO$_2$N(CH$_2$CH$_3$)$_2$ | 2-COSCH$_3$-phenyl | |
| a-288 | 4-Cl-phenyl | —SO$_2$N[(CH$_2$)$_2$CH$_3$][(CH$_2$)$_2$CH$_3$] | 2-CF$_3$-phenyl | Oily |
| a-289 | 4-Cl-phenyl | —SO$_2$N[(CH$_2$)$_2$CH$_3$][(CH$_2$)$_3$CH$_3$] | 2-CF$_3$-phenyl | |
| a-290 | 4-Cl-phenyl | —SO$_2$-phenyl | 2-CF$_3$-phenyl | 151~155° C. |

TABLE I-a-continued (Ia)

[Structure: (R3)m-phenyl-C(OR1)=C(CN)-phenyl-(R2)l-Y]

| Comp. No. | (R3)m | R1 | (R2)l Y | Physical Property (Melting point) |
|---|---|---|---|---|
| a-291 | 4-Cl-phenyl | 4-CH3-phenyl-SO2- | 2-F3C-phenyl | 152~156° C. |
| a-292 | 4-Cl-phenyl | phenyl-SO2O- | 2-F3C-phenyl | |
| a-293 | 4-Cl-phenyl | 4-CH3-phenyl-SO2O- | 2-F3C-phenyl | |
| a-294 | 4-Cl-phenyl | phenyl-SO2S- | 2-F3C-phenyl | |
| a-295 | 4-Cl-phenyl | phenyl-SO2CH2- | 2-F3C-phenyl | |

TABLE I-a-continued (Ia)

| Comp. No. | (R₃)ₘ-phenyl | R₁ | (R₂)ₗ-ring-Y | Physical Property (Melting point) |
|---|---|---|---|---|
| a-296 | 4-Cl-C₆H₄ | | 2-CF₃-C₆H₄ | |
| a-297 | 4-Cl-C₆H₄ | —SO₂CH₂-C₆H₄-4-F | 2-CF₃-C₆H₄ | 164~167° C. |
| a-298 | 4-Cl-C₆H₄ | —SO₂CH₂-C₆H₄-4-OCH₃ | 2-CF₃-C₆H₄ | Oily |
| a-299 | 4-Cl-C₆H₄ | —SO₂N(pyrrolidine) | 2-CF₃-C₆H₄ | |
| a-300 | 4-Cl-C₆H₄ | —SO₂N(piperidine) | 2-CF₃-C₆H₄ | 80~82° C. |
| | 4-Cl-C₆H₄ | —SO₂N(morpholine) | 2-CF₃-C₆H₄ | |

TABLE I-a-continued

| Comp. No. | $(R_3)_m$ | $R_1$ | $(R_2)_l$ Y | Physical Property (Melting point) |
|---|---|---|---|---|
| a-301 | 4-Cl-C6H4 | —CSCH3 | 2-CF3-C6H4 | |
| a-302 | 4-Cl-C6H4 | —CSCH2CH3 | 2-CF3-C6H4 | Oily |
| a-303 | 4-Cl-C6H4 | —CSOCH3 | 2-CF3-C6H4 | Oily |
| a-304 | 4-Cl-C6H4 | —CSOCH2CH3 | 2-CF3-C6H4 | |
| a-305 | 4-Cl-C6H4 | —CS2CH3 | 2-CF3-C6H4 | $n_D^{39.4}$ 1.5930 |

TABLE I-a-continued
(Ia)
| Comp. No. | (R3)m | R1 | (R2)l Y | Physical Property (Melting point) |
|---|---|---|---|---|
| a-306 | 4-Cl-C6H4 | —CS₂CH₂CH₃ | 2-CF₃-C6H4 | $n_D^{27.2}$ 1.5612 |
| a-307 | 4-Cl-C6H4 | —CS₂CH(CH₃)₂ | 2-CF₃-C6H4 | $n_D^{33.8}$ 1.5824 |
| a-308 | 4-Cl-C6H4 | —CS₂(CH₂)₃CH₃ | 2-CF₃-C6H4 | 80.3° C. |
| a-309 | 4-Cl-C6H4 | —CS₂CH₂CF₃ | 2-CF₃-C6H4 | |
| a-310 | 4-Cl-C6H4 | —CS₂CH₂CH=CH₂ | 2-CF₃-C6H4 | $n_D^{26.8}$ 1.6040 |

TABLE I-a-continued

| Comp. No. | (R₃)ₘ─⟨phenyl⟩ | R₁ | ─⟨phenyl⟩─(R₂)₁ | Physical Property (Melting point) |
|---|---|---|---|---|
| a-311 | 4-Cl-C₆H₄ | ─CS₂CH₂CH=CCl₂ | 2-CF₃-C₆H₄ | |
| a-312 | 4-Cl-C₆H₄ | ─CS₂CH₂C≡CH | 2-CF₃-C₆H₄ | |
| a-313 | 4-Cl-C₆H₄ | ─CS₂CH₂C≡CCl | 2-CF₃-C₆H₄ | |
| a-314 | 4-Cl-C₆H₄ | ─CS₂─cyclohexyl | 2-CF₃-C₆H₄ | |
| a-315 | 4-Cl-C₆H₄ | ─CSNHC(CH₃)₃ | 2-CF₃-C₆H₄ | |

TABLE I-a-continued

| Comp. No. | (R$_3$)$_m$ | R$_1$ | (R$_2$)$_l$ | Physical Property (Melting point) |
|---|---|---|---|---|
| a-316 | 4-Cl-phenyl | —CSN(CH$_3$)$_2$ | 2-CF$_3$-phenyl | 137.9° C. |
| a-317 | 4-Cl-phenyl | —CSN(CH$_2$CH$_3$)$_2$ | 2-CF$_3$-phenyl | 121~123° C. |
| a-318 | 4-Cl-phenyl | —CS-phenyl | 2-CF$_3$-phenyl | Oily |
| a-319 | 4-Cl-phenyl | —CSO-phenyl | 2-CF$_3$-phenyl | Oily |
| a-320 | 4-Cl-phenyl | —CSO-(4-CH$_3$-phenyl) | 2-CF$_3$-phenyl | |

TABLE I-a-continued (Ia)

[Structure: (R₃)ₘ-phenyl-C(OR₁)=C(CN)-phenyl-(R₂)ₗ-Y]

| Comp. No. | (R₃)ₘ-phenyl | R₁ | (R₂)ₗ-Y-phenyl | Physical Property (Melting point) |
|---|---|---|---|---|
| a-321 | 4-Cl-phenyl | —CSO—(4-OCH₃-phenyl) | 2-F₃C-phenyl | 113.8° C. |
| a-322 | 4-Cl-phenyl | —CS₂—phenyl | 2-F₃C-phenyl | $n_D^{39.4}$ 1.6204 |
| a-323 | 4-Cl-phenyl | —CS₂—(4-Cl-phenyl) | 2-F₃C-phenyl | |
| a-324 | 4-Cl-phenyl | —CS₂—(4-CH₃-phenyl) | 2-F₃C-phenyl | 71.9° C. |
| a-325 | 4-Cl-phenyl | —CS₂CH₂—phenyl | 2-F₃C-phenyl | |

TABLE I-a-continued $$(Ia)$$

| Comp. No. | $(R_3)_m$ | $R_1$ | $(R_2)_l$ Y | Physical Property (Melting point) |
|---|---|---|---|---|
| a-326 | 4-Cl-C$_6$H$_4$ | —CS$_2$CH$_2$-(4-Cl-C$_6$H$_4$) | 2-CF$_3$-C$_6$H$_4$ | |
| a-327 | 4-Cl-C$_6$H$_4$ | —CS$_2$CH$_2$-(4-CH$_3$-C$_6$H$_4$) | 2-CF$_3$-C$_6$H$_4$ | 129.6° C. |
| a-328 | 4-Cl-C$_6$H$_4$ | —CSN(pyrrolidinyl) | 2-CF$_3$-C$_6$H$_4$ | 125.8° C. |
| a-329 | 4-Cl-C$_6$H$_4$ | —CSN(morpholinyl) | 2-CF$_3$-C$_6$H$_4$ | |
| a-330 | 4-Cl-C$_6$H$_4$ | —CH$_2$CN | 2-CF$_3$-C$_6$H$_4$ | Oily |

TABLE I-a-continued (Ia)

| Comp. No. | (R₃)ₘ | R₁ | (R₂)ₗ/Y ring | Physical Property (Melting point) |
|---|---|---|---|---|
| a-331 | 4-Cl-phenyl | -CH₂-phenyl | 2-CH₃, 3-CF₃ phenyl | 114~116° C. |
| a-332 | 4-Cl-phenyl | -CH₂-(2,3-diCl-phenyl) | 2-CH₃, 3-CF₃ phenyl | 74~75° C. |
| a-333 | 4-Cl-phenyl | -CH₂-(3-Cl-phenyl) | 2-CH₃, 3-CF₃ phenyl | Oily |
| a-334 | 4-Cl-phenyl | -CH₂-(4-Cl-phenyl) | 2-CH₃, 3-CF₃ phenyl | 123~127° C. |
| a-335 | 4-Cl-phenyl | -CH₂-(2-F-phenyl) | 2-CH₃, 3-CF₃ phenyl | 93~94° C. |

TABLE I-a-continued

| Comp. No. | (R₃)ₘ | R₁ | (R₂)ₗ with Y ring | Physical Property (Melting point) |
|---|---|---|---|---|
| a-336 | 4-Cl-C₆H₄ | -CH₂-C₆H₄-4-F | 2-CF₃-C₆H₄ | 109–111° C. |
| a-337 | 4-Cl-C₆H₄ | -CH₂-C₆H₄-2-Br | 2-CF₃-C₆H₄ | 90–91° C. |
| a-338 | 4-Cl-C₆H₄ | -CH₂-C₆H₄-4-Br | 2-CF₃-C₆H₄ | 140–141° C. |
| a-339 | 4-Cl-C₆H₄ | -CH₂-C₆H₄-4-CH₃ | 2-CF₃-C₆H₄ | 136–137° C. |
| a-340 | 4-Cl-C₆H₄ | -CH₂-C₆H₄-4-CF₃ | 2-CF₃-C₆H₄ | 98–100° C. |

TABLE I-a-continued (Ia)

| Comp. No. | $(R_3)_m$ | $R_1$ | $(R_2)_l$ Y | Physical Property (Melting point) |
|---|---|---|---|---|
| a-341 | 4-Cl-C6H4 | —CH2—C6H4-4-NO2 | 2-CF3-C6H4 | 125~130° C. |
| a-342 | 4-Cl-C6H4 | —CH2OCH2—C6H5 | 2-CF3-C6H4 | Oily |
| a-343 | 4-Cl-C6H4 | —CH2OCH2—C6H4-4-CH3 | 2-CF3-C6H4 | |
| a-344 | 4-Cl-C6H4 | —CH2CO—C6H5 | 2-CF3-C6H4 | 105~110° C. |
| a-345 | 4-Cl-C6H4 | —CH2CO—C6H4-4-Cl | 2-CF3-C6H4 | |

TABLE I-a-continued

| Comp. No. | (R3)m | R1 | (R2)l Y | Physical Property (Melting point) |
|---|---|---|---|---|
| a-346 | 4-Cl-C6H4 | 4-CH3-C6H4-CH2CO- | 2-CF3-C6H4 | |
| a-347 | 4-Cl-C6H4 | 4-CF3-C6H4-CH2CO- | 2-CF3-C6H4 | |
| a-348 | 4-Cl-C6H4 | pyridin-2-yl-CH2- | 2-CF3-C6H4 | |
| a-349 | 4-Cl-C6H4 | pyridin-4-yl-CH2- | 2-CF3-C6H4 | |
| a-350 | 4-Cl-C6H4 | 5-CF3-pyridin-2-yl-CH2- | 2-CF3-C6H4 | Oily |

TABLE I-a-continued

| Comp. No. | (R₃)ₘ | R₁ | (R₂)ₗ | Physical Property (Melting point) |
|---|---|---|---|---|
| a-351 | 4-Cl-C₆H₄ | —CH₂COCH₃ | 2-CF₃-C₆H₄ | |
| a-352 | 4-Cl-C₆H₄ | —CH₂SOCH₃ | 2-CF₃-C₆H₄ | Oily |
| a-353 | 4-Cl-C₆H₄ | —CH₂Si(CH₃)₃ | 2-CF₃-C₆H₄ | |
| a-354 | 4-F-C₆H₄ | —CH₂C≡Cl | 2-CF₃-C₆H₄ | |
| a-355 | 4-F-C₆H₄ | —COS-C₆H₁₁ | 2-CF₃-C₆H₄ | |

TABLE I-a-continued $$(Ia)$$

| Comp. No. | (R₃)ₘ-phenyl | R₁ | (R₂)ₗ-Y | Physical Property (Melting point) |
|---|---|---|---|---|
| a-356 | 4-F-C₆H₄ | —SOCH₃ | 2-CF₃-C₆H₄ | |
| a-357 | 4-F-C₆H₄ | —SO₂CH₂C≡CH | 2-CF₃-C₆H₄ | |
| a-358 | 4-F-C₆H₄ | —SO₂N(CH₃)₂ | 2-SCH₃-C₆H₄ | |
| a-359 | 4-F-C₆H₄ | —SO₂N(CH₂CH₃)₂ | 2-CF₃-C₆H₄ | 44–45° C. |
| a-360 | 4-F-C₆H₄ | —SO₂N((CH₂)₂CH₃)₂ | 2-CF₃-C₆H₄ | 58–59° C. |

TABLE I-a-continued (Ia)

[Structure: (R3)m-phenyl-C(OR1)=C(CN)-phenyl-(R2)l with Y]

| Comp. No. | (R3)m | R1 | (R2)l Y | Physical Property (Melting point) |
|---|---|---|---|---|
| a-361 | 4-F-phenyl | 4-(SO2OCF3)-phenyl | 2-CF3-phenyl | |
| a-362 | 4-F-phenyl | —CS2CH2CH3 | 2-CF3-phenyl | $n_D^{31.0}$ 1.5762 |
| a-363 | 4-F-phenyl | —CSN(CH3)2 | 2-CF3-phenyl | 98–100° C. |
| a-364 | 4-F-phenyl | —CSN(CH3)CH2CH3 | 2-CF3-phenyl | |
| a-365 | 4-F-phenyl | —CSN(pyrrolidinyl) | 2-CF3-phenyl | 127.9° C. |

TABLE I-a-continued

| Comp. No. | (R$_3$)$_m$ | R$_1$ | (R$_2$)$_l$ | Physical Property (Melting point) |
|---|---|---|---|---|
| a-366 | 4-F-C$_6$H$_4$ | —CSN(piperidine) | 2-CF$_3$-C$_6$H$_4$ | |
| a-367 | 4-F-C$_6$H$_4$ | —CH$_2$-C$_6$H$_5$ | 2-CF$_3$-C$_6$H$_4$ | 101~104° C. |
| a-368 | 4-Br-C$_6$H$_4$ | —CH$_2$CH$_3$ | 2-CF$_3$-C$_6$H$_4$ | Oily |
| a-369 | 4-Br-C$_6$H$_4$ | —CO-C$_6$H$_4$-4-NO$_2$ | 2-CF$_3$-C$_6$H$_4$ | |
| a-370 | 4-Br-C$_6$H$_4$ | —SO$_2$-cyclopropyl | 2-CF$_3$-C$_6$H$_4$ | |

TABLE I-a-continued

| Comp. No. | (R₃)ₘ | R₁ | (R₂)ₗ | Physical Property (Melting point) |
|---|---|---|---|---|
| a-371 | 4-Br-phenyl | —SO₂N(CH₂CH₃)₂ | 2-CF₃-phenyl | 71~73° C. |
| a-372 | 4-Br-phenyl | —SO₂N(—(CH₂)₂CH₃)(CH₂)₂CH₃ | 2-CF₃-phenyl | 65~66° C. |
| a-373 | 4-Br-phenyl | pyrrolidinyl-SO₂— | 2-CF₃-phenyl | 173~176° C. |
| a-374 | 4-Br-phenyl | —CSCH₂OCH₂CH₃ | 2-CF₃-phenyl | — |
| a-375 | 4-Br-phenyl | —CS₂CH₂CH₃ | 2-CF₃-phenyl | 102.4° C. |

TABLE I-a-continued

| Comp. No. | (R₃)ₘ | R₁ | (R₂)ₗ | Physical Property (Melting point) |
|---|---|---|---|---|
| a-376 | 4-Br-C₆H₄ | —CSN(CH₃)₂ | 3-CF₃-2-CH₃-C₆H₃ | 124~128° C. |
| a-377 | 4-Br-C₆H₄ | —CSN(CH₃)₂ | 4'-CH₃-biphenyl-4-yl | |
| a-378 | 4-Br-C₆H₄ | —CSCH₂-C₆H₅ | 3-CF₃-2-CH₃-C₆H₃ | |
| a-379 | 4-Br-C₆H₄ | —CS₂CH₂-C₆H₅ | 3-CF₃-2-CH₃-C₆H₃ | |
| a-380 | 4-Br-C₆H₄ | —CS₂CH₂-(4-CN-C₆H₄) | 3-CF₃-2-CH₃-C₆H₃ | |

TABLE I-a-continued

| Comp. No. | (R₃)ₘ | R₁ | (R₂)₁ | Physical Property (Melting point) |
|---|---|---|---|---|
| a-381 | 4-Br-C₆H₄ | —CSN(pyrrolidine) | 2-CF₃-C₆H₄ | 136.2° C. |
| a-382 | 4-Br-C₆H₄ | —CH₂-C₆H₅ | 2-CF₃-C₆H₄ | Oily |
| a-383 | 4-I-C₆H₄ | —COSCH₂CF₃ | 2-CF₃-C₆H₄ | |
| a-384 | 4-I-C₆H₄ | —SO₂N(CH₂CH₃)₂ | 2-CF₃-C₆H₄ | Oily |
| a-385 | 4-I-C₆H₄ | —SO₂SCH₂-C₆H₅ | 2-CF₃-C₆H₄ | |

TABLE I-a-continued
(Ia)
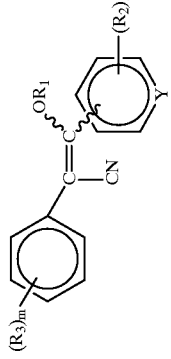
| Comp. No. | (R₃)ₘ | R₁ | (R₂)ₗ | Physical Property (Melting point) |
|---|---|---|---|---|
| a-386 | 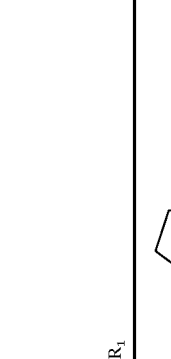 | —SO₂N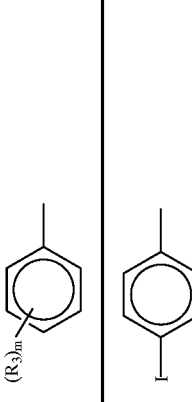 | 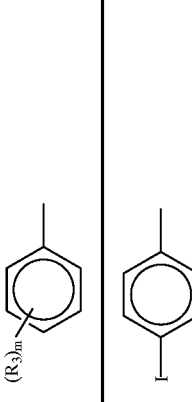 | 154~155° C. |
| a-387 | 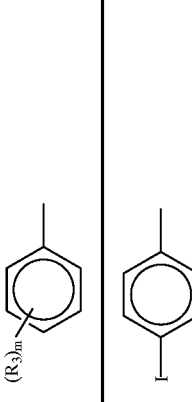 | —CS₂CH₃ | 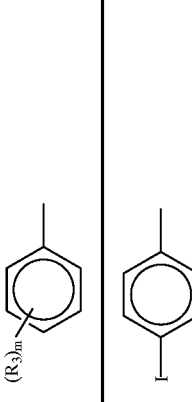 | 130.2° C. |
| a-388 | 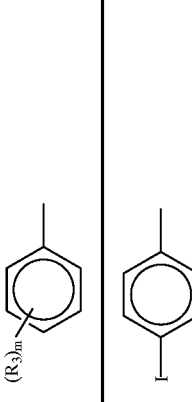 | —CSN(CH₃)₂ | 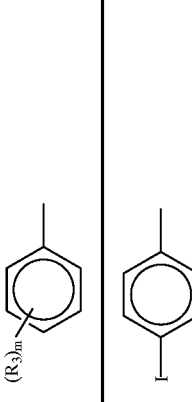 | 141~144° C. |
| a-389 | 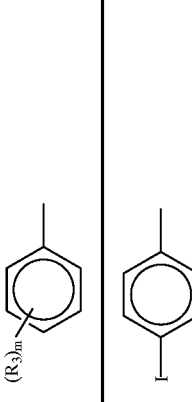 | —CH₂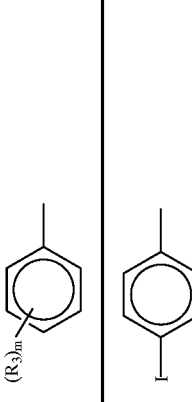 | 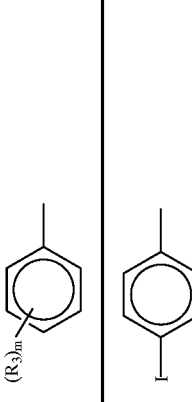 | |
| a-390 | 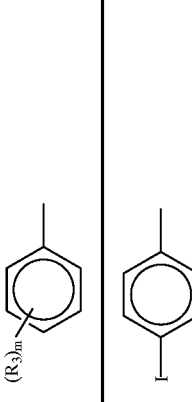 | —CH₂OCH₃ | 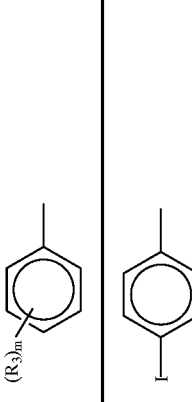 | Z-isomer 68~70° C. |

TABLE I-a-continued

| Comp. No. | (R₃)ₘ | R₁ | (R₂)ₗ Y | Physical Property (Melting point) |
|---|---|---|---|---|
| a-391 | 2-Cl, 4-Cl phenyl | —CH₂SCH₃ | 2-CH₃, 3-CF₃ phenyl | Z-isomer 113~118° C. |
| a-392 | 2-Cl, 4-Cl phenyl | —COCH₂OCH₃ | 2-CH₃, 3-CF₃ phenyl | Oily |
| a-393 | 2-Cl, 4-Cl phenyl | —COSCH₂CH=CH₂ | 2-CH₃, 3-CF₃ phenyl | |
| a-394 | 2-Cl, 4-Cl phenyl | —CO₂CH₃ | 2-CH₃, 3-CF₃ phenyl | Oily |
| a-395 | 2-Cl, 4-Cl phenyl | —CO₂CH₂CH₃ | 2-CH₃, 3-CF₃ phenyl | Oily |

TABLE I-a-continued

| Comp. No. | $(R_3)_m$ | $R_1$ | $(R_2)_l$-Y | Physical Property (Melting point) |
|---|---|---|---|---|
| a-396 | 2-CH3, 4-Cl (phenyl) | 4-CN-C6H4-CO- | 2-CF3-phenyl | |
| a-397 | 2-CH3, 4-Cl (phenyl) | 4-SO2CH3-C6H4-CO- | 2-CF3-phenyl | |
| a-398 | 2-CH3, 4-Cl (phenyl) | C6H5-CH2- | 2-CF3-phenyl | Oily |
| a-399 | 2-CH3, 4-Cl (phenyl) | —SO2(CH2)3CH3 | 2-CF3-phenyl | |
| a-400 | 2-CH3, 4-Cl (phenyl) | —SO2SCH2CH=CH2 | 2-CF3-phenyl | Z-isomer Oily |

TABLE I-a-continued (Ia)

| Comp. No. | (R3)m | R1 | (R2)l Y | Physical Property (Melting point) |
|---|---|---|---|---|
| a-401 | 2-methyl-4-chloro-phenyl (Cl, CH3) | —SO₂NH(CH₂)₂CH₃ | 2-CF₃-phenyl | |
| a-402 | 2-methyl-4-chloro-phenyl | —SO₂NHC(CH₃)₃ | 2-CF₃-phenyl | |
| a-403 | 2-methyl-4-chloro-phenyl | —SO₂N(CH₂CH₃)₂ | 2-CF₃-phenyl | |
| a-404 | 2-methyl-4-chloro-phenyl | —SO₂N—(CH₂)₂CH₃ / (CH₂)₂CH₃ | 2-CF₃-phenyl | 124~125° C. |
| a-405 | 2-methyl-4-chloro-phenyl | —SO₂N—(CH₂)₃CH₃ / (CH₂)₃CH₃ | 2-CF₃-phenyl | 105~107° C. |

TABLE I-a-continued

| Comp. No. | (R₃)ₘ | R₁ | (R₂)ₗ Y | Physical Property (Melting point) |
|---|---|---|---|---|
| a-406 | 2-CH₃, 4-Cl phenyl | 4-CF₃-phenyl-SO₂- | 2-CF₃-phenyl | 120–121° C. |
| a-407 | 2-CH₃, 4-Cl phenyl | pyrrolidin-1-yl-SO₂- | 2-CF₃-phenyl | |
| a-408 | 2-CH₃, 4-Cl phenyl | piperidin-1-yl-SO₂- | 2-CF₃-phenyl | |
| a-409 | 2-CH₃, 4-Cl phenyl | morpholin-4-yl-SO₂- | 2-CF₃-phenyl | |
| a-410 | 2-CH₃, 4-Cl phenyl | —CSCH₃ | 2-CF₃-phenyl | |

TABLE I-a-continued

| Comp. No. | (R₃)ₘ | R₁ | (R₂)ₗ Y | Physical Property (Melting point) |
|---|---|---|---|---|
| a-411 | 2-Cl, 4-Cl phenyl | —CSCH₂CH₃ | 2-CF₃ phenyl | |
| a-412 | 2-Cl, 4-Cl phenyl | —CSOCH₃ | 2-CF₃ phenyl | |
| a-413 | 2-Cl, 4-Cl phenyl | —CSOCH₂CH₃ | 2-CF₃ phenyl | Oily |
| a-414 | 2-Cl, 4-Cl phenyl | —CS₂CH₃ | 2-CF₃ phenyl | |
| a-415 | 2-Cl, 4-Cl phenyl | —CS₂CH₂CH₃ | 4-(4-CH₃-phenoxy)phenyl | $n_D^{39.6}$ 1.5998 |

TABLE I-a-continued (Ia)

| Comp. No. | (R₃)ₘ | R₁ | (R₂)ₗ Y | Physical Property (Melting point) |
|---|---|---|---|---|
| a-416 | 2-CH₃, 4-Cl phenyl | —CSCH₂C(Cl)=CHCl | 2-CF₃ phenyl | |
| a-417 | 2-CH₃, 4-Cl phenyl | —CSN(CH₃)₂ | 2-CF₃ phenyl | 97–98° C. |
| a-418 | 2-CH₃, 4-Cl phenyl | —CSN(CH₂CH₃)₂ | 2-CF₃ phenyl | Oily |
| a-419 | 2-CH₃, 4-Cl phenyl | —CSO-phenyl | 2-CF₃ phenyl | |
| a-420 | 2-CH₃, 4-Cl phenyl | —CO-(4-NO₂-phenyl) | 2-CF₃ phenyl | |

TABLE I-a-continued (Ia)

| Comp. No. | $(R_3)_m$ | $R_1$ | $(R_2)_l$ Y | Physical Property (Melting point) |
|---|---|---|---|---|
| a-421 | 2,4-diCl-phenyl | —CH$_2$OCH$_2$-phenyl | 2-CF$_3$-phenyl | Oily |
| a-422 | 2,4-diCl-phenyl | —CH$_2$CO$_2$CH$_3$ | 2-CF$_3$-phenyl | 77~80° C. |
| a-423 | 2,4-diCl-phenyl | —CH$_2$SO$_2$CH$_3$ | 2-CF$_3$-phenyl | Z-isomer 161~163° C. |
| a-424 | 2,4-diCl-phenyl | —CH$_2$SO$_2$CH$_3$ | 2-CF$_3$-phenyl | E-isomer 175~178° C. |
| a-425 | 2,4-diF-phenyl | —CS$_2$CH$_3$ | 2-CF$_3$-phenyl | $n_D^{26.8}$ 1.5680 |

TABLE I-a-continued

| Comp. No. | (R₃)ₘ | R₁ | (R₂)ₗ Y | Physical Property (Melting point) |
|---|---|---|---|---|
| a-426 | 2,4-difluorophenyl | —CSN(CH₃)₂ | 2-CF₃-phenyl | 109.2° C. |
| a-427 | 2,4-difluorophenyl | pyrrolidine-CSN | 2-CF₃-phenyl | 139.1° C. |
| a-428 | 4-Cl-2-F-phenyl | —SO₂CH₂CH(CH₃)₂ | 2-CF₃-phenyl | Oily |
| a-429 | 4-Cl-2-F-phenyl | —SO₂N(CH₃)₂ | 2-CF₃-phenyl | 64–68° C. |
| a-430 | 4-Cl-2-F-phenyl | —SO₂N(CH₂CH₃)₂ | 2-CF₃-phenyl | 95–98° C. |

TABLE I-a-continued

| Comp. No. | (R₃)ₘ | R₁ | (R₂)ₗ Y | Physical Property (Melting point) |
|---|---|---|---|---|
| a-431 | 4-Cl, 2-F, methyl | —CSN(CH₃)₂ | 2-CF₃ phenyl | 87~90° C. |
| a-432 | 4-C(CH₃)₃ phenyl | —COSCH₂CH=CCl₂ | 2-CF₃ phenyl | |
| a-433 | 4-C(CH₃)₃ phenyl | —SO₂SCH₂CH=CCl₂ | 2-CF₃ phenyl | |
| a-434 | 4-C(CH₃)₃ phenyl | —SO₂N(CH₃)₂ | 2-CF₃ phenyl | 78~80° C. |
| a-435 | 4-C(CH₃)₃ phenyl | —CSN(CH₃)₂ | 2-CF₃ phenyl | 105~107° C. |

TABLE I-a-continued

| Comp. No. | (R₃)ₘ | R₁ | (R₂)₁ | Physical Property (Melting point) |
|---|---|---|---|---|
| a-436 | 4-F₃C-C₆H₄ | —COSCH₂C≡CH | 2-F₃C-C₆H₄ | |
| a-437 | 4-F₃C-C₆H₄ | —COSCH₂C≡Cl | 2-F₃C-C₆H₄ | |
| a-438 | 4-F₃CO-C₆H₄ | —COCH₃ | 2-F₃C-C₆H₄ | |
| a-439 | 4-H₃COS-C₆H₄ | —SO₂CH₂CH₃ | 2-F₃C-C₆H₄ | |
| a-440 | 4-C₆H₅-C₆H₄ | —SO₂CH₂CH₃ | 2-F₃C-C₆H₄ | Oily |

TABLE I-a-continued

| Comp. No. | (R3)m | R1 | (R2)l Y | Physical Property (Melting point) |
|---|---|---|---|---|
| a-441 | 4-CH3-C6H4 | —CS2CH2CH3 | 2-CF3-C6H4 | |
| a-442 | 4-Cl-C6H4-O-C6H4- (3-CH3) | —CSN(CH3)2 | 2-CF3-C6H4 | |
| a-443 | 4-CH3-C6H4-O-C6H4- (3-H3C) | —COSCH3 | 2-CF3-C6H4 | |
| a-444 | 4-Cl-C6H4 | —CO-(2-pyridyl) | 2-CF3-C6H4 | Oily |
| a-445 | 4-Cl-C6H4 | —CO-(3-pyridyl) | 2-CF3-C6H4 | Oily |

TABLE I-a-continued

| Comp. No. | (R3)m | R1 | (R2)l Y | Physical Property (Melting point) |
|---|---|---|---|---|
| a-446 | 4-Cl-C6H4 | 4-pyridyl-CO- | 2-CF3-C6H4 | |
| a-447 | 4-Cl-C6H4 | 5-CF3-2-pyridyl-CO- | 2-CF3-C6H4 | |
| a-448 | 4-Cl-C6H4 | 2-pyridyl-SO2- | 2-CF3-C6H4 | |
| a-449 | 4-Cl-C6H4 | 3-pyridyl-SO2- | 2-CF3-C6H4 | |
| a-450 | 4-Cl-C6H4 | 4-pyridyl-SO2- | 2-CF3-C6H4 | |

TABLE I-a-continued

| Comp. No. | (R₃)ₘ | R₁ | (R₂)ₗ | Physical Property (Melting point) |
|---|---|---|---|---|
| a-451 | 4-Cl-C₆H₄ | —CS₂(CH₂)₂CH₃ | 2-CF₃-C₆H₄ | 71.9° C. |
| a-452 | 4-Cl-C₆H₄ | —CS₂CH₂CO₂CH₃ | 2-CF₃-C₆H₄ | $n_D^{26.6}$ 1.5825 |
| a-453 | 4-Cl-C₆H₄ | —CS₂CH₂CO₂CH₃ | 2-CF₃-C₆H₄ | |
| a-454 | 4-F-C₆H₄ | —CS₂CH₃ | 2-CF₃-C₆H₄ | |
| a-455 | 4-F-C₆H₄ | —CS₂CH₂CO₂CH₃ | 2-CF₃-C₆H₄ | |

TABLE I-a-continued

| Comp. No. | (R3)m | R1 | (R2)l | Physical Property (Melting point) |
|---|---|---|---|---|
| a-456 | 4-Br-C6H4 | N-piperidinyl-SO2– | 2-CF3-C6H4 | 100~101° C. |
| a-457 | 4-Br-C6H4 | –CS2CH3 | 2-CF3-C6H4 | |
| a-458 | 4-Br-C6H4 | –CS2CH2CO2CH3 | 2-CF3-C6H4 | |
| a-459 | 2,4-F2-C6H3 | –SO2N(CH3)2 | 2-CF3-C6H4 | 115~118° C. |
| a-460 | 2,4-F2-C6H3 | –SO2N(CH2CH3)2 | 2-CF3-C6H4 | Oily |

TABLE I-a-continued (Ia) structure with $(R_3)_m$-phenyl-C(OR$_1$)=C(CN)-phenyl-$(R_2)_l$-Y

| Comp. No. | $(R_3)_m$ | $R_1$ | $(R_2)_l$, Y | Physical Property (Melting point) |
|---|---|---|---|---|
| a-461 | 2-methyl-3-fluoro-4-chlorophenyl | —CS$_2$CH$_3$ | 2-CF$_3$-phenyl | $n_D^{26.2}$ 1.5364 |
| a-462 | 4-Cl, 2-CH$_3$ phenyl | 2-CH$_3$, 5-CH$_3$ benzoyl | 2-CF$_3$-phenyl | Oily |
| a-463 | 4-Cl, 2-CH$_3$ phenyl | 3-CH$_3$ benzoyl | 2-CF$_3$-phenyl | 72~74° C. |
| a-464 | 4-Cl, 2-CH$_3$ phenyl | 2,6-di-CH$_3$ benzoyl | 2-CF$_3$-phenyl | 152~155° C. |
| a-465 | 4-Cl, 2-CH$_3$ phenyl | 2,5-di-CH$_3$ benzoyl | 2-CF$_3$-phenyl | 110~113° C. |

TABLE I-a-continued
| Comp. No. | (R₃)ₘ | R₁ | (R₂)ₗ Y | Physical Property (Melting point) |
|---|---|---|---|---|
| a-466 |  |  |  | 104~106° C. |
| a-467 | 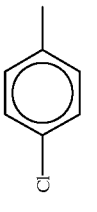 |  | 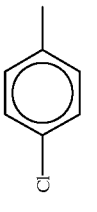 | 99~101° C. |
| a-468 |  | —COS(CH₂)₂CH₃ | 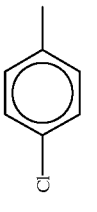 | |
| a-469 |  | —CONHCH₃ | 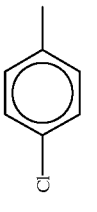 | Oily |
| a-470 |  | —SO₂N(CH₃)CH₂CH₃ | | 98~100° C. |

TABLE I-a-continued

| Comp. No. | (R₃)ₘ | R₁ | (R₂)ₗ | Physical Property (Melting point) |
|---|---|---|---|---|
| a-471 | 4-Cl-C₆H₄ | —SO₂N(CH₂)₂CH₃ with CH₃ | 2-CF₃-C₆H₄ | 55–57° C. |
| a-472 | 4-Cl-C₆H₄ | —S-C₆H₅ | 2-CF₃-C₆H₄ | Oily |
| a-473 | 4-Cl-C₆H₄ | —SO-C₆H₅ | 2-CF₃-C₆H₄ | 188–191° C. |
| a-474 | 4-Cl-C₆H₄ | —SCCl₃ | 2-CF₃-C₆H₄ | Oily |
| a-475 | 4-Cl-C₆H₄ | —SN(CH₃)₂ | 2-CF₃-C₆H₄ | Oily |

TABLE I-a-continued

| Comp. No. | (R₃)ₘ | R₁ | (R₂)ₗ | Physical Property (Melting point) |
|---|---|---|---|---|
| a-476 | 4-Cl-C₆H₄ | —SN(CH₂CH₃)₂ | 2-CF₃-C₆H₄ | |
| a-477 | 4-Cl-C₆H₄ | pyrrolidin-1-yl-S— | 2-CF₃-C₆H₄ | |
| a-478 | 4-Cl-C₆H₄ | —SCH₂CH₃ | 2-CF₃-C₆H₄ | |
| a-479 | 4-Cl-C₆H₄ | —S(CH₂)₂CH₃ | 2-CF₃-C₆H₄ | |
| a-480 | 4-Cl-C₆H₄ | —SCH(CH₃)₂ | 2-CF₃-C₆H₄ | |

TABLE I-a-continued

| Comp. No. | (R₃)ₘ | R₁ | (R₂)ₗ | Physical Property (Melting point) |
|---|---|---|---|---|
| a-481 | 4-Cl-C₆H₄ | —SC(CH₃)₃ | 2-CF₃-C₆H₄ | |
| a-482 | 4-Cl-C₆H₄ | —SCH₂Cl | 2-CF₃-C₆H₄ | |
| a-483 | 4-Cl-C₆H₄ | —SCHCl₂ | 2-CF₃-C₆H₄ | |
| a-484 | 4-Cl-C₆H₄ | —SCH₂OCH₃ | 2-CF₃-C₆H₄ | |
| a-485 | 4-Cl-C₆H₄ | —SCH₂SCH₃ | 2-CF₃-C₆H₄ | |

TABLE I-a-continued

| Comp. No. | (R₃)ₘ | R₁ | (R₂)ₗ | Physical Property (Melting point) |
|---|---|---|---|---|
| a-486 | 4-Cl-phenyl | —SCH₂N(CH₃)₂ | 2-CF₃-phenyl | |
| a-487 | 4-Cl-phenyl | —S₂CH₃ | 2-CF₃-phenyl | Oily |
| a-488 | 4-Cl-phenyl | —S₂CH₂CH₃ | 2-CF₃-phenyl | |
| a-489 | 4-Cl-phenyl | —S₂CH(CH₃)₂ | 2-CF₃-phenyl | |
| a-490 | 4-Cl-phenyl | —S₂C(CH₃)₃ | 2-CF₃-phenyl | |

TABLE I-a-continued

| Comp. No. | (R3)m | R1 | (R2)l Y | Physical Property (Melting point) |
|---|---|---|---|---|
| a-491 | 4-Cl-phenyl | —SN(CH₃)OCH₃ | 2-CF₃-phenyl | |
| a-492 | 4-Cl-phenyl | —SN(CH₂CH₃)OCH₃ | 2-CF₃-phenyl | |
| a-493 | 4-Cl-phenyl | —S₂-phenyl | 2-CF₃-phenyl | |
| a-494 | 4-Cl-phenyl | —S₂-(4-Cl-phenyl) | 2-CF₃-phenyl | |
| a-495 | 4-Cl-phenyl | —S₂-(4-CH₃-phenyl) | 2-CF₃-phenyl | |

TABLE I-a-continued

| Comp. No. | $(R_3)_m$ | $R_1$ | $(R_2)_l$ Y | Physical Property (Melting point) |
|---|---|---|---|---|
| a-496 | 4-Cl-C6H4 | 4-CF3-C6H4-S2- | 2-CF3-C6H4 | |
| a-497 | 4-Cl-C6H4 | 4-OCH3-C6H4-S2- | 2-CF3-C6H4 | |
| a-498 | 4-Cl-C6H4 | —SO2N(CH3)OCH3 | 2-CF3-C6H4 | |
| a-499 | 4-Cl-C6H4 | —SO2N(OCH3)(CH2CH3) | 2-CF3-C6H4 | |
| a-500 | 4-Cl-C6H4 | —SO2CH2N(CH3)2 | 2-CF3-C6H4 | |

TABLE I-a-continued (Ia)

| Comp. No. | (R₃)ₘ | R₁ | (R₂)ₗ Y | Physical Property (Melting point) |
|---|---|---|---|---|
| a-501 | 4-Cl-C₆H₄ | —SO₂(CH₂)₂N(CH₃)CH₃ | 2-F₃C-C₆H₄ | |
| a-502 | 4-Cl-C₆H₄ | —SO₂(CH₂)₂OCH₃ | 2-F₃C-C₆H₄ | |
| a-503 | 4-Cl-C₆H₄ | —SO₂CH₂SCH₃ | 2-F₃C-C₆H₄ | |
| a-504 | 4-Cl-C₆H₄ | —SO₂(CH₂)₂SCH₃ | 2-F₃C-C₆H₄ | |
| a-505 | 4-Cl-C₆H₄ | —SO₂-cyclopentyl | 2-F₃C-C₆H₄ | |

TABLE I-a-continued

| Comp. No. | (R$_3$)$_m$ | R$_1$ | (R$_2$)$_l$ Y | Physical Property (Melting point) |
|---|---|---|---|---|
| a-506 | 4-Cl-phenyl | 1-(imidazolyl-SO$_2$)- | 2-CF$_3$-phenyl | |
| a-507 | 4-Cl-phenyl | 1-(pyrrolyl-SO$_2$)- | 2-CF$_3$-phenyl | |
| a-508 | 4-Cl-phenyl | 2-(oxazolyl-SO$_2$)- | 2-CF$_3$-phenyl | |
| a-509 | 4-Cl-phenyl | 2-(thiazolyl-SO$_2$)- | 2-CF$_3$-phenyl | |
| a-510 | 4-Cl-phenyl | 4-(oxazolyl-SO$_2$)- | 2-CF$_3$-phenyl | |

TABLE I-a-continued

| Comp. No. | (R₃)ₘ | R₁ | (R₂)ₗ Y | Physical Property (Melting point) |
|---|---|---|---|---|
| a-511 | 4-Cl-phenyl | thiazol-4-yl-SO₂- | 2-F₃C-phenyl | |
| a-512 | 4-Cl-phenyl | isoxazol-5-yl-SO₂- | 2-F₃C-phenyl | |
| a-513 | 4-Cl-phenyl | isothiazol-5-yl-SO₂- | 2-F₃C-phenyl | |
| a-514 | 4-Cl-phenyl | pyrimidin-2-yl-SO₂- | 2-F₃C-phenyl | |
| a-515 | 4-Cl-phenyl | pyridazin-3-yl-SO₂- | 2-F₃C-phenyl | |

TABLE I-a-continued (Ia) structure: (R3)m-phenyl-C(OR1)=C(CN)-phenyl(R2)l-Y

| Comp. No. | (R3)m | R1 | (R2)l-Y | Physical Property (Melting point) |
|---|---|---|---|---|
| a-516 | 4-Cl-phenyl | 3-pyridyl-SO2— | 2-CF3-phenyl | |
| a-517 | 4-Cl-phenyl | pyrimidinyl-SO2— | 2-CF3-phenyl | |
| a-518 | 4-Cl-phenyl | —SON(CH3)2 | 2-CF3-phenyl | |
| a-519 | 4-Cl-phenyl | —SON(CH2CH3)2 | 2-CF3-phenyl | |
| a-520 | 4-Cl-phenyl | —SON(CH3)OCH3 | 2-CF3-phenyl | |

TABLE I-a-continued

| Comp. No. | (R₃)ₘ | R₁ | (R₂)₁ | Physical Property (Melting point) |
|---|---|---|---|---|
| a-521 | 4-Cl-C₆H₄ | —SON(CH₂CH₃)OCH₃ | 2-CF₃-C₆H₄ | |
| a-522 | 4-Cl-C₆H₄ | —S(=O)OCH₃ | 2-CF₃-C₆H₄ | |
| a-523 | 4-Cl-C₆H₄ | —S(=O)OCH₂CH₃ | 2-CF₃-C₆H₄ | |
| a-524 | 4-Cl-C₆H₄ | —S(=O)SCH₃ | 2-CF₃-C₆H₄ | |
| a-525 | 4-Cl-C₆H₄ | —S(=O)SCH₂CH₃ | 2-CF₃-C₆H₄ | |

TABLE I-a-continued (Ia)

| Comp. No. | $(R_3)_m$ | $R_1$ | $(R_2)_l$ | Physical Property (Melting point) |
|---|---|---|---|---|
| a-526 | 4-Cl-C$_6$H$_4$ | 4-C(CH$_3$)$_3$-C$_6$H$_4$-CO- | 2-CH$_3$-3-CF$_3$-C$_6$H$_3$ | 118~120° C. |
| a-527 | 4-Cl-C$_6$H$_4$ | 4-CF$_3$-C$_6$H$_4$-CO- | 2-CH$_3$-3-CF$_3$-C$_6$H$_3$ | |
| a-528 | 4-Cl-C$_6$H$_4$ | —COCH$_2$SOCH$_3$ | 2-CH$_3$-3-CF$_3$-C$_6$H$_3$ | |
| a-529 | 4-Cl-C$_6$H$_4$ | —COCH$_2$SO$_2$CH$_3$ | 2-CH$_3$-3-CF$_3$-C$_6$H$_3$ | |
| a-530 | 4-Cl-C$_6$H$_4$ | —CO(CH$_2$)$_2$NH$_2$ | 2-CH$_3$-3-CF$_3$-C$_6$H$_3$ | |

TABLE I-a-continued (Ia)

| Comp. No. | (R₃)ₘ | R₁ | (R₂)ₗ Y | Physical Property (Melting point) |
|---|---|---|---|---|
| a-531 | 4-Cl-C₆H₄ | —COCH₂NHCH₃ | 2-CF₃-C₆H₄ | |
| a-532 | 4-Cl-C₆H₄ | —COCH₂N(CH₃)₂ | 2-CF₃-C₆H₄ | |
| a-533 | 4-Cl-C₆H₄ | —CO₂CH₂-C₆H₅ | 2-CF₃-C₆H₄ | |
| a-534 | 4-Cl-C₆H₄ | —CO₂CH₂-C₆H₄-4-SO₂CF₃ | 2-CF₃-C₆H₄ | |
| a-535 | 4-Cl-C₆H₄ | —CO-C₆H₄-2-CF₃ | 2-CF₃-C₆H₄ | 123~124° C. |

TABLE I-a-continued

| Comp. No. | (R₃)ₘ | R₁ | (R₂)ₗ Y | Physical Property (Melting point) |
|---|---|---|---|---|
| a-536 | 4-Cl-C₆H₄ | 4-CH(CH₃)₂-C₆H₄-CO- | 2-CF₃-C₆H₄ | 125~128° C. |
| a-537 | 4-Cl-C₆H₄ | 4-OCH(CH₃)₂-C₆H₄-CO- | 2-CF₃-C₆H₄ | 28~30° C. |
| a-538 | 4-Cl-C₆H₄ | 4-SCH₃-C₆H₄-CO- | 2-CF₃-C₆H₄ | |
| a-539 | 4-Cl-C₆H₄ | 4-SO₂CH₃-C₆H₄-CO- | 2-CF₃-C₆H₄ | |
| a-540 | 4-Cl-C₆H₄ | 4-N(CH₃)₂-C₆H₄-CO- | 2-CF₃-C₆H₄ | 170~175° C. |

TABLE I-a-continued

| Comp. No. | $(R_3)_m$ | $R_1$ | $(R_2)_l$ | Physical Property (Melting point) |
|---|---|---|---|---|
| a-541 | 4-Cl-C6H4 | 2-(CH3)2N-C6H4-CO- | 2-CF3-C6H4 | |
| a-542 | 4-Cl-C6H4 | —CSOCH(CH3)2 | 2-CF3-C6H4 | |
| a-543 | 4-Cl-C6H4 | —CSOC(CH3)3 | 2-CF3-C6H4 | |
| a-544 | 4-Cl-C6H4 | —CSOCH2CF3 | 2-CF3-C6H4 | |
| a-545 | 4-Cl-C6H4 | —CSOCH2CH=CH2 | 2-CF3-C6H4 | |

TABLE I-a-continued

| Comp. No. | (R₃)ₘ | R₁ | (R₂)ₗ | Physical Property (Melting point) |
|---|---|---|---|---|
| a-546 | 4-Cl-C₆H₄ | —CSOCH₂C≡CH | 2-CF₃-C₆H₄ | |
| a-547 | 4-Cl-C₆H₄ | —CSOCH₂CH=CCl₂ | 2-CF₃-C₆H₄ | |
| a-548 | 4-Cl-C₆H₄ | —CSOCH₂C≡Cl | 2-CF₃-C₆H₄ | |
| a-549 | 4-Cl-C₆H₄ | —CSO-cyclopentyl | 2-CF₃-C₆H₄ | |
| a-550 | 4-Cl-C₆H₄ | —CSOCH₂-C₆H₅ | 2-CF₃-C₆H₄ | |

TABLE I-a-continued

| Comp. No. | $(R_3)_m$ | $R_1$ | $(R_2)_l$ Y | Physical Property (Melting point) |
|---|---|---|---|---|
| a-551 | 4-Cl-phenyl | —CSOCH$_2$-(4-NO$_2$-phenyl) | 2-CF$_3$-phenyl | |
| a-552 | 4-Cl-phenyl | —CSOCH$_2$-(4-OCF$_3$-phenyl) | 2-CF$_3$-phenyl | |
| a-553 | 4-Cl-phenyl | —CSOCH$_2$-(4-CN-phenyl) | 2-CF$_3$-phenyl | |
| a-554 | 4-Cl-phenyl | —CSO-(4-CF$_3$-phenyl) | 2-CF$_3$-phenyl | |
| a-555 | 4-Cl-phenyl | —CSO-(4-SCH$_3$-phenyl) | 2-CF$_3$-phenyl | |

TABLE I-a-continued

| Comp. No. | $(R_3)_m$ | $R_1$ | $(R_2)_l$ Y | Physical Property (Melting point) |
|---|---|---|---|---|
| a-556 | 4-Cl-C6H4 | 4-C(CH3)3-C6H4-CSO- | 2-F3C-C6H4 | |
| a-557 | 4-Cl-C6H4 | 3-CH3-4-CH3-C6H3-CSO- | 2-F3C-C6H4 | |
| a-558 | 4-Cl-C6H4 | C6H5-CH2S- | 2-F3C-C6H4 | |
| a-559 | 4-Cl-C6H4 | C6H5-CH2SO- | 2-F3C-C6H4 | |
| a-560 | 4-Cl-C6H4 | C6H5-CH2SO2- | 2-F3C-C6H4 | |

TABLE I-a-continued (Ia)

| Comp. No. | (R$_3$)$_m$ | R$_1$ | (R$_2$)$_l$ Y | Physical Property (Melting point) |
|---|---|---|---|---|
| a-561 | 4-Cl-C$_6$H$_4$ | —(CH$_2$)$_2$-C$_6$H$_5$ | 2-CF$_3$-C$_6$H$_4$ | |
| a-562 | 4-Cl-C$_6$H$_4$ | —CH$_2$O-C$_6$H$_5$ | 2-CF$_3$-C$_6$H$_4$ | |
| a-563 | 4-Cl-C$_6$H$_4$ | —CH$_2$SCH$_2$-C$_6$H$_5$ | 2-CF$_3$-C$_6$H$_4$ | |
| a-564 | 4-Cl-C$_6$H$_4$ | —CH$_2$CSCH$_3$ | 2-CF$_3$-C$_6$H$_4$ | |
| a-565 | 4-Cl-C$_6$H$_4$ | —CH$_2$CSOCH$_3$ | 2-CF$_3$-C$_6$H$_4$ | |

TABLE I-a-continued
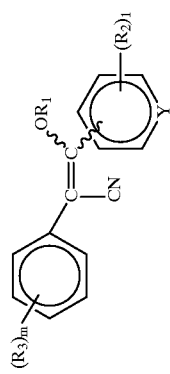
| Comp. No. | (R₃)ₘ | R₁ | (R₂)ₗ | Physical Property (Melting point) |
|---|---|---|---|---|
| a-566 | 4-Cl-C₆H₄ | 4-Cl-C₆H₄-SCH₂- | 2-CF₃-C₆H₄ | |
| a-567 | 4-Cl-C₆H₄ | 4-CF₃-C₆H₄-(CH₂)₂- | 2-CF₃-C₆H₄ | |
| a-568 | 4-Cl-C₆H₄ | thiophen-3-yl-CO₂- | 2-CF₃-C₆H₄ | |
| a-569 | 4-Cl-C₆H₄ | thiazol-4-yl-CO₂- | 2-CF₃-C₆H₄ | |
| a-570 | 4-Cl-C₆H₄ | isoxazol-3-yl-CO₂- | 2-CF₃-C₆H₄ | |

TABLE I-a-continued (Ia)

| Comp. No. | (R₃)ₘ | R₁ | (R₂)ₗ Y | Physical Property (Melting point) |
|---|---|---|---|---|
| a-571 | 4-Cl-C₆H₄ | isothiazol-4-yl-CO₂- | 2-CF₃-C₆H₄ | |
| a-572 | 4-Cl-C₆H₄ | pyridin-3-yl-CO₂- | 2-CF₃-C₆H₄ | |
| a-573 | 4-Cl-C₆H₄ | pyridin-3-yl-CS₂- | 2-CF₃-C₆H₄ | E-isomer 116.1° C. |
| a-574 | 4-Cl-C₆H₄ | pyridin-2-yl-CS₂- | 2-CF₃-C₆H₄ | Z-isomer n_D^{39.2} 1.5716 |
| a-575 | 4-Cl-C₆H₄ | pyridin-2-yl-CS₂- | 2-CF₃-C₆H₄ | |

TABLE I-a-continued (Ia)

| Comp. No. | (R₃)ₘ-phenyl | R₁ | (R₂)ₗ-Y ring | Physical Property (Melting point) |
|---|---|---|---|---|
| a-576 | 4-Cl-C₆H₄ | 5-CF₃-pyridin-2-yl (CS) | 2-F₃C-C₆H₄ | |
| a-577 | 4-Cl-C₆H₄ | thiophen-3-yl (CS) | 2-F₃C-C₆H₄ | |
| a-578 | 4-Cl-C₆H₄ | furan-3-yl (CS) | 2-F₃C-C₆H₄ | |
| a-579 | 4-Cl-C₆H₄ | isoxazol-4-yl (CS) | 2-F₃C-C₆H₄ | |
| a-580 | 4-Cl-C₆H₄ | 1-CH₃-3-CH₃-pyrazol-4-yl (CS) | 2-F₃C-C₆H₄ | |

TABLE I-a-continued

| Comp. No. | (R₃)ₘ | R₁ | (R₂)ₗ | Physical Property (Melting point) |
|---|---|---|---|---|
| a-581 | 4-Cl-C₆H₄ | -CH₂-(pyridin-3-yl) | 2-CF₃-C₆H₄ | |
| a-582 | 4-Cl-C₆H₄ | -CH₂-(2-chloropyridin-5-yl) | 2-CF₃-C₆H₄ | |
| a-583 | 4-Cl-C₆H₄ | -CH₂-(thiophen-2-yl) | 2-CF₃-C₆H₄ | |
| a-584 | 4-Cl-C₆H₄ | -CH₂-(furan-2-yl) | 2-CF₃-C₆H₄ | |
| a-585 | 4-Cl-C₆H₄ | -CH₂-(thiazol-2-yl) | 2-CF₃-C₆H₄ | |

TABLE I-a-continued

| Comp. No. | $(R_3)_m$ | $R_1$ | $(R_2)_l$ | Physical Property (Melting point) |
|---|---|---|---|---|
| a-586 | 4-Cl-C6H4 | ![imidazole-CH2] H3C-N/N-CH2- | 2-CF3-C6H4 | |
| a-587 | 4-Cl-C6H4 | —CS2(CH2)2N(CH3)CH3 | 2-CF3-C6H4 | |
| a-588 | 4-Cl-C6H4 | —CS2(CH2)2SCH3 | 2-CF3-C6H4 | |
| a-589 | 4-Cl-C6H4 | —CS2(CH2)2SCH2CH3 | 2-CF3-C6H4 | |
| a-590 | 4-Cl-C6H4 | —CS2(CH2)2CN | 2-CF3-C6H4 | |

TABLE I-a-continued

| Comp. No. | (R₃)ₘ | R₁ | (R₂)ₗ Y |
|---|---|---|---|
| a-591 | 4-Cl-C₆H₄ | —CS₂(CH₂)₂NO₂ | 2-CF₃-C₆H₄ |
| a-592 | 4-Cl-C₆H₄ | —CS₂(CH₂)₂OCHF₂ | 2-CF₃-C₆H₄ |
| a-593 | 4-Cl-C₆H₄ | —CS₂CCl₃ | 2-CF₃-C₆H₄ |
| a-594 | 4-Cl-C₆H₄ | —CS₂-(pyrrol-3-yl) | 2-CF₃-C₆H₄ |
| a-595 | 4-Cl-C₆H₄ | —CS₂-(thiazol-4-yl) | 2-CF₃-C₆H₄ |

TABLE I-a-continued

| Comp. No. | (R$_3$)$_m$ phenyl | R$_1$ | (R$_2$)$_l$ Y-ring | Physical Property (Melting point) |
|---|---|---|---|---|
| a-596 | 4-Cl-C$_6$H$_4$ | isoxazol-3-yl-CH$_2$S- | 2-CF$_3$-C$_6$H$_4$ | |
| a-597 | 4-Cl-C$_6$H$_4$ | isothiazol-4-yl-CH$_2$S- | 2-CF$_3$-C$_6$H$_4$ | |
| a-598 | 4-Cl-C$_6$H$_4$ | (1-CH$_3$-3-CH$_3$-pyrazol-4-yl)-CH$_2$S- | 2-CF$_3$-C$_6$H$_4$ | |
| a-599 | 4-Cl-C$_6$H$_4$ | —COCH$_3$ | 2-CHF$_2$-C$_6$H$_4$ | |
| a-600 | 4-Cl-C$_6$H$_4$ | —COCH$_2$CH$_3$ | 2-CHF$_2$-C$_6$H$_4$ | |

TABLE I-a-continued

| Comp. No. | (R₃)ₘ | R₁ | (R₂)ₗ | Physical Property (Melting point) |
|---|---|---|---|---|
| a-601 | 4-Cl-C₆H₄ | —COCH(CH₃)₂ | 2-CHF₂-C₆H₄ | |
| a-602 | 4-Cl-C₆H₄ | —COC(CH₃)₃ | 2-CHF₂-C₆H₄ | |
| a-603 | 4-Cl-C₆H₄ | —SO₂CH₃ | 2-CHF₂-C₆H₄ | |
| a-604 | 4-Cl-C₆H₄ | —SO₂CH₂CH₃ | 2-CHF₂-C₆H₄ | |
| a-605 | 4-Cl-C₆H₄ | —SO₂N(CH₃)₂ | 2-CHF₂-C₆H₄ | |

TABLE I-a-continued (Ia)

| Comp. No. | (R$_3$)$_m$ | R$_1$ | (R$_2$)$_l$ Y | Physical Property (Melting point) |
|---|---|---|---|---|
| a-606 | 4-Cl-C$_6$H$_4$ | —SO$_2$N(CH$_2$CH$_3$)$_2$ | 2-CHF$_2$-C$_6$H$_4$ | |
| a-607 | 4-Cl-C$_6$H$_4$ | —SO$_2$NCH$_2$CH$_3$ <br>         CH$_3$ | 2-CHF$_2$-C$_6$H$_4$ | |
| a-608 | 4-Cl-C$_6$H$_4$ | —CO$_2$CH$_3$ | 2-CHF$_2$-C$_6$H$_4$ | |
| a-609 | 4-Cl-C$_6$H$_4$ | —CO$_2$CH$_2$CH$_3$ | 2-CHF$_2$-C$_6$H$_4$ | |
| a-610 | 4-Cl-C$_6$H$_4$ | —CO—C$_6$H$_5$ | 2-CHF$_2$-C$_6$H$_4$ | |

TABLE I-a-continued

| Comp. No. | (R₃)ₘ | R₁ | (R₂)ₗ | Physical Property (Melting point) |
|---|---|---|---|---|
| a-611 | 4-Cl-C₆H₄ | —CSOCH₃ | 2-CHF₂-C₆H₄ | |
| a-612 | 4-Cl-C₆H₄ | —CSOCH₂CH₃ | 2-CHF₂-C₆H₄ | |
| a-613 | 4-Cl-C₆H₄ | —CSO-C₆H₅ | 2-CHF₂-C₆H₄ | |
| a-614 | 4-Cl-C₆H₄ | —CSN(CH₃)₂ | 2-CHF₂-C₆H₄ | |
| a-615 | 4-Cl-C₆H₄ | —CS₂CH₃ | 2-CHF₂-C₆H₄ | |

TABLE I-a-continued

| Comp. No. | $(R_3)_m$ | $R_1$ | $(R_2)_l$ | Physical Property (Melting point) |
|---|---|---|---|---|
| a-616 | 4-Cl-C$_6$H$_4$ | —CS$_2$CH$_2$CH$_3$ | 2-CHF$_2$-C$_6$H$_4$ | |
| a-617 | 4-Cl-C$_6$H$_4$ | —CS$_2$CH$_2$CH=CH$_2$ | 2-CHF$_2$-C$_6$H$_4$ | |
| a-618 | 4-Cl-C$_6$H$_4$ | —CSN(CH$_3$)$_2$ | 2-CHF$_2$-C$_6$H$_4$ | |
| a-619 | 4-Cl-C$_6$H$_4$ | —CS$_2$CH$_3$ | 2-CHF$_2$-C$_6$H$_4$ | |
| a-620 | 4-Cl-C$_6$H$_4$ | —CS$_2$CH$_2$CH$_3$ | 2-CHF$_2$-C$_6$H$_4$ | |

TABLE I-a-continued (Ia)

| Comp. No. | (R₃)ₘ | R₁ | (R₂)ₗ Y | Physical Property (Melting point) |
|---|---|---|---|---|
| a-621 | 4-Cl-C₆H₄ | —CS₂CH₂CH=CH₂ | 2-CHF₂-C₆H₄ | |
| a-622 | 4-Cl-C₆H₄ | —SO₂N(CH₃)₂ | 2-CHF₂-C₆H₄ | |
| a-623 | 4-Cl-C₆H₄ | —SO₂N(CH₂CH₃)₂ | 2-CH₂F-C₆H₄ | |
| a-624 | 4-Cl-C₆H₄ | —SO₂NCH₂CH₃ / CH₃ | 2-CH₂F-C₆H₄ | |
| a-625 | 4-Cl-C₆H₄ | —COCH₃ | 2-CF₃-3-Cl-C₆H₃ | |

TABLE I-a-continued

| Comp. No. | (R₃)ₘ–phenyl | R₁ | (R₂)ₗ–Y ring | Physical Property (Melting point) |
|---|---|---|---|---|
| a-626 | 4-Cl-C₆H₄ | —COCH(CH₃)₂ | 2-CH₃-3-CF₃-C₆H₃-O- (OCH₃ on ring with CH₃ and CF₃) | |
| a-627 | 4-Cl-C₆H₄ | —COC(CH₃)₃ | 2-CH₃-3-CF₃-C₆H₃-S- (SCH₃) | |
| a-628 | 4-Cl-C₆H₄ | —SO₂CH₃ | 2-CH₃-3-CF₃-C₆H₃-SO₂CH₃ | |
| a-629 | 4-Cl-C₆H₄ | —SO₂CH₂CH₃ | 2-CH₃-3-CF₃-C₆H₃-CF₃ | |

TABLE I-a-continued (Ia)

| Comp. No. | (R₃)ₘ | R₁ | Y(R₂)ₗ | Physical Property (Melting point) |
|---|---|---|---|---|
| a-630 | 4-Cl-C₆H₄ | —SO₂N(CH₃)₂ | 3-F, 2-CF₃-C₆H₃ | |
| a-631 | 4-Cl-C₆H₄ | —SO₂N(CH₂CH₃)₂ | 3-F, 2-CF₃-C₆H₃ | |
| a-632 | 4-Cl-C₆H₄ | —SO₂N(CH₂CH₃)CH₃ | 3-F, 2-CF₃-C₆H₃ | |
| a-633 | 4-Cl-C₆H₄ | —SO₂N(CH₃)₂ | 4-F, 2-CF₃-C₆H₃ | |
| a-634 | 4-Cl-C₆H₄ | —SO₂N(CH₃)₂ | 4-CF₃, 2-CF₃-C₆H₃ | |

TABLE I-a-continued

| Comp. No. | (R₃)ₘ | R₁ | (R₂)ₗ Y | Physical Property (Melting point) |
|---|---|---|---|---|
| a-635 | 4-Cl-C₆H₄ | —SO₂N(CH₃)₂ | 2-CF₃-3-Cl-C₆H₃ | |
| a-636 | 4-Cl-C₆H₄ | —SO₂N(CH₃)₂ | 2-CF₃-3-CH₃-C₆H₃ | |
| a-637 | 4-F-C₆H₄ | —COSCH₃ | 2-CF₃-C₆H₄ | Oily |
| a-638 | 4-F-C₆H₄ | —COSCH₂CH₃ | 2-CF₃-C₆H₄ | Oily |
| a-639 | 4-F-C₆H₄ | —SO₂N(pyrrolidinyl) | 2-CF₃-C₆H₄ | 107~110° C. |

TABLE I-a-continued

| Comp. No. | (R₃)ₘ | R₁ | (R₂)ₗ | Physical Property (Melting point) |
|---|---|---|---|---|
| a-640 | 4-F-C₆H₄ | —SO₂N(piperidine) | 2-CF₃-C₆H₄ | 83–84° C. |
| a-641 | 4-Br-C₆H₄ | —SO₂NCH₂CH₃ / CH₃ | 2-CF₃-C₆H₄ | 110–111° C. |
| a-642 | 4-F-C₆H₄ | —COCH₃ | 4-(CH=CCl₂)-C₆H₄ | |
| a-643 | 4-Cl-C₆H₄ | —COCH₂CH₃ | 4-SCF₃-C₆H₄ | |
| a-644 | 4-Br-C₆H₄ | —COCH(CH₃)₂ | 4-SOCF₃-C₆H₄ | |

TABLE I-a-continued (Ia)

| Comp. No. | $(R_3)_m$ | $R_1$ | $(R_2)_l$ Y | Physical Property (Melting point) |
|---|---|---|---|---|
| a-645 | 4-I-phenyl | —COC(CH$_3$)$_3$ | 4-SO$_2$CF$_3$-phenyl | |
| a-646 | 2,4-diF-phenyl | —SO$_2$CH$_3$ | 4-C≡CH-phenyl | |
| a-647 | 2-F,4-Cl-phenyl | —SO$_2$CH$_2$CH$_3$ | 4-(4-Cl-phenylthio)-phenyl | |
| a-648 | 2,4-diCl-phenyl | —SO$_2$N(CH$_3$)$_2$ | 4-(4-Cl-phenylsulfinyl)-phenyl | |
| a-649 | 4-C(CH$_3$)$_3$-phenyl | —SO$_2$N(CH$_2$CH$_3$)$_2$ | 4-(4-Cl-phenylsulfonyl)-phenyl | |

TABLE I-a-continued

| Comp. No. | $(R_3)_m$ | $R_1$ | $(R_2)_l$ Y | Physical Property (Melting point) |
|---|---|---|---|---|
| a-650 | 4-F-C6H4 | —SO2NCH2CH3 / CH3 | 4-CH3-C6H4-OCH2C≡CCl | |
| a-651 | 4-Cl-C6H4 | —SO2-pyrrolidinyl | 4-CH3-C6H4-OCH2CH=CCl2 | |
| a-652 | 4-Br-C6H4 | —CO2CH3 | 4-CH3-C6H4-SCH2CH=CCl2 | |
| a-653 | 4-I-C6H4 | —CO2CH2CH3 | 4-CH3-C6H4-SCH2C≡CCl | |
| a-654 | 2,4-F2-C6H3 | —CO-C6H5 | 4-CH3-C6H4-SOCH2CH=CCl2 | |

TABLE I-a-continued

| Comp. No. | (R3)m | R1 | Y(R2)l | Physical Property (Melting point) |
|---|---|---|---|---|
| a-655 | 4-Cl | —CO-(4-CH3-C6H4) | 4-(SO2CH2CH=CCl2)-C6H4- | |
| a-656 | 2-F, 4-Cl | —CSOCH3 | 4-(SOCH2C≡CCl)-C6H4- | |
| a-657 | 2-Cl, 4-Cl | —CSOCH2CH3 | 4-(SO2CH2C≡CCl)-C6H4- | |
| a-658 | 4-C(CH3)3 | —CSO-C6H5 | 4-(OCH2-(4-Cl-C6H4))-C6H4- | |
| a-659 | 4-F | —CSN(CH3)2 | 4-(SCH2-(4-Cl-C6H4))-C6H4- | |

TABLE I-a-continued

| Comp. No. | (R₃)ₘ | R₁ | Y-(R₂)ₗ ring | Physical Property (Melting point) |
|---|---|---|---|---|
| a-660 | 4-methylphenyl | | | |
| a-661 | 4-bromophenyl | —CS₂CH₃ | 4-methylphenyl-CO-(4-chlorophenyl) | |
| a-662 | 4-iodophenyl | —CS₂CH₂CH₃ | 4-methylphenyl-CH₂-phenyl | |
| a-663 | 2,4-difluorophenyl | —SO₂N(CH₂)₂CH₃ (CH₂)₂CH₃ | 2-(CF₃)phenyl | 57–58° C. |
| a-664 | 2-fluoro-4-chlorophenyl | —SO₂-pyrrolidinyl | 2-(CF₃)phenyl | 119–120° C. |
| | | —SO₂NCH₂CH₃ CH₃ | 2-(CF₃)phenyl | 130–132° C. |

TABLE I-a-continued
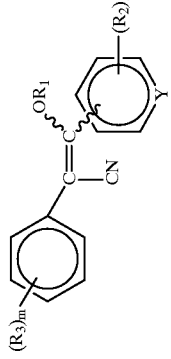
| Comp. No. | (R₃)ₘ | R₁ | (R₂)ₗ | Physical Property (Melting point) |
|---|---|---|---|---|
| a-665 | 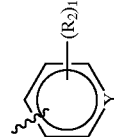 | —CS₂CH₃ |  | $n_D^{30.2}$ 1.5922 |
| a-666 | 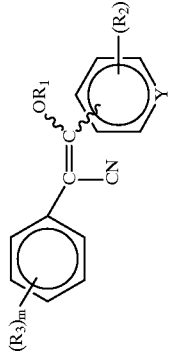 | —CS₂CH₃ | 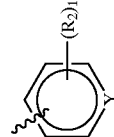 | E-isomer 79.2° C. |
| a-667 |  | —CS₂CH₃ | 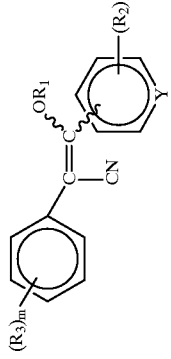 | Z-isomer $n_D^{18.6}$ 1.6004 |
| a-668 | 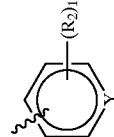 | —CS₂CH₃ |  | |
| a-669 | 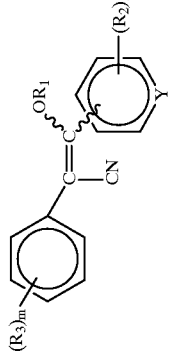 | —SO₂CH₃ | 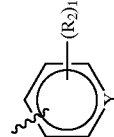 | $n_D^{38.8}$ 1.5062 |

TABLE I-a-continued

| Comp. No. | (R₃)ₘ─⟨⟩ | R₁ | ─⟨⟩─(R₂)₁ Y | Physical Property (Melting point) |
|---|---|---|---|---|
| a-670 | 4-Cl, 2-CH₃-phenyl | ─SO₂CH₂CH₃ | 2-CF₃-phenyl | |
| a-671 | 4-Cl, 2-CH₃-phenyl | ─SO₂N(CH₃)₂ | 2-CF₃-phenyl | |
| a-672 | 4-Cl, 2-CH₃-phenyl | ─SO₂N(CH₂CH₃)₂ | 2-CF₃-phenyl | |
| a-673 | 4-Cl, 2-CH₃-phenyl | ─SO₂NCH₂CH₃ (CH₃) | 2-CF₃-phenyl | |
| a-674 | 4-Cl, 2-CH₃-phenyl | ─SCH₃ | 2-CF₃-phenyl | |

TABLE I-a-continued

| Comp. No. | (R₃)ₘ | R₁ | (R₂)ₗ | Physical Property (Melting point) |
|---|---|---|---|---|
| a-675 | 4-Cl, 2-CH₃ phenyl | —SCH₂CH₃ | 2-CF₃ phenyl | |
| a-676 | 4-Cl, 2-CH₃ phenyl | —SCCl₃ | 2-CF₃ phenyl | |
| a-677 | 4-Cl, 2-CH₃ phenyl | —S-phenyl | 2-CF₃ phenyl | |
| a-678 | 4-Cl, 2-CH₃ phenyl | —SN(CH₃)₂ | 2-CF₃ phenyl | |
| a-679 | 4-Cl, 2-CH₃ phenyl | —SN(CH₂CH₃)₂ | 2-CF₃ phenyl | |

TABLE I-a-continued

| Comp. No. | (R3)m | R1 | (R2)l | Physical Property (Melting point) |
|---|---|---|---|---|
| a-680 | 4-(H3C)3C-C6H4 | —CSOCH3 | 2-CH3-6-CF3-C6H3 | Oily |
| a-681 | 4-(H3C)3C-C6H4 | —CSOCH2CH3 | 2-CH3-6-CF3-C6H3 | Oily |
| a-682 | 4-(H3C)3C-C6H4 | —CSO-C6H5 | 2-CH3-6-CF3-C6H3 | Oily |
| a-683 | 4-(H3C)3C-C6H4 | —COSCH3 | 2-CH3-6-CF3-C6H3 | Oily |
| a-684 | 4-(H3C)3C-C6H4 | —COSCH2CH3 | 2-CH3-6-CF3-C6H3 | 116~117° C. |

TABLE I-a-continued (Ia)

| Comp. No. | (R3)m | R1 | (R2)l Y | Physical Property (Melting point) |
|---|---|---|---|---|
| a-685 | 4-(H3C)3C-C6H4 | —CS-C6H5 | 2-F3C-C6H4 | |
| a-686 | 4-(H3C)3C-C6H4 | —CS2CH3 | 2-F3C-C6H4 | $n_D^{31.8}$ 1.5746 |
| a-687 | 4-(H3C)3C-C6H4 | —SCH3 | 2-F3C-C6H4 | |
| a-688 | 4-(H3C)3C-C6H4 | —SCH2CH3 | 2-F3C-C6H4 | |
| a-689 | 4-(H3C)3C-C6H4 | —SCCl3 | 2-F3C-C6H4 | |

TABLE I-a-continued

| Comp. No. | (R₃)ₘ | R₁ | (R₂)ₗ | Physical Property (Melting point) |
|---|---|---|---|---|
| a-690 | 4-CH₃-C₆H₄ | —SN(CH₃)₂ | 2-CF₃-C₆H₄ | |
| a-691 | 4-CH₃-C₆H₄ | —SN(CH₂CH₃)₂ | 2-CF₃-C₆H₄ | |
| a-692 | 3-(CH=CCl₂)-C₆H₄ | —CS₂CH₃ | 2-CF₃-C₆H₄ | 103.6° C. |
| a-693 | 3-(CH=CF₂)-C₆H₄ | —CS₂CH₃ | 2-CF₃-C₆H₄ | |
| a-694 | 4-SCF₃-C₆H₄ | —CS₂CH₃ | 2-CF₃-C₆H₄ | |

TABLE I-a-continued

| Comp. No. | (R₃)ₘ | R₁ | (R₂)ₗ Y | Physical Property (Melting point) |
|---|---|---|---|---|
| a-695 | 4-SOCF₃-phenyl | —CS₂CH₃ | 2-CF₃-phenyl | |
| a-696 | 3-SO₂CF₃-phenyl | —CS₂CH₃ | 2-CF₃-phenyl | |
| a-697 | 4-C≡CH-phenyl | —CS₂CH₃ | 2-CF₃-phenyl | |
| a-698 | 4-Cl-phenyl-S-4-CH₃-phenyl | —CS₂CH₃ | 2-CF₃-phenyl | |
| a-699 | 4-Cl-phenyl-SO-4-CH₃-phenyl | —CS₂CH₃ | 2-CF₃-phenyl | |

TABLE I-a-continued

| Comp. No. | $(R_3)_m$ | $R_1$ | $(R_2)_l$ | Physical Property (Melting point) |
|---|---|---|---|---|
| a-700 | 4-CH₃-C₆H₄- | | | |
| a-701 | 4-Cl-C₆H₄-SO₂-C₆H₄(4-CH₃)- | —CS₂CH₃ | 2-CF₃-6-CH₃-C₆H₃- | |
| a-702 | 2-(OCH₂CH=CCl₂)-4-CH₃-C₆H₃- | —CS₂CH₃ | 2-CF₃-6-CH₃-C₆H₃- | |
| a-703 | 2-(OCH₂C≡Cl)-4-CH₃-C₆H₃- | —CS₂CH₃ | 2-CF₃-6-CH₃-C₆H₃- | |
| a-704 | 2-(SCH₂CH=CCl₂)-4-CH₃-C₆H₃- | —CS₂CH₃ | 2-CF₃-6-CH₃-C₆H₃- | |
| | 2-(SCH₂C≡Cl)-4-CH₃-C₆H₃- | —CS₂CH₃ | 2-CF₃-6-CH₃-C₆H₃- | |

TABLE I-a-continued

| Comp. No. | (R₃)ₘ─⬡ | R₁ | ─⬡─(R₂)₁ Y | Physical Property (Melting point) |
|---|---|---|---|---|
| a-705 | 4-(SOCH₂CH=CCl₂)-phenyl | —CS₂CH₃ | 2-CF₃-phenyl | |
| a-706 | 4-(SO₂CH₂CH=CCl₂)-phenyl | —CS₂CH₃ | 2-CF₃-phenyl | |
| a-707 | 4-(SOCH₂C≡CCl)-phenyl | —CS₂CH₃ | 2-CF₃-phenyl | |
| a-708 | 4-(SO₂CH₂C≡CCl)-phenyl | —CS₂CH₃ | 2-CF₃-phenyl | |
| a-709 | 4-Cl-phenyl-O-CH₂-C(CH₃)₂-(4-methylphenyl) | —CS₂CH₃ | 2-CF₃-phenyl | |

TABLE I-a-continued

| Comp. No. | (R₃)ₘ─⟨phenyl⟩ | R₁ | ─⟨phenyl⟩─Y─(R₂)ₗ | Physical Property (Melting point) |
|---|---|---|---|---|
| a-710 | 4-(4-chlorophenyl-CH₂S)-3-methylphenyl | —CS₂CH₃ | 2-CF₃-phenyl | |
| a-711 | 4-(4-chlorophenoxy)-3-methylphenyl (CO linkage) | —CS₂CH₃ | 2-CF₃-phenyl | |
| a-712 | 4-benzyl-3-methylphenyl (CH₂) | —CS₂CH₃ | 2-CF₃-phenyl | |
| a-713 | 4-bromophenyl-methyl | —CS₂CH₃ | 2-CF₃-phenyl | 88.0° C. |

TABLE I-b
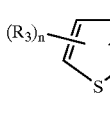
(Ib)
| Comp. No. | (R3)n─⟨S⟩─ | R1 | ─⟨Y⟩(R2)1 | Physical property (Melting point) |
|---|---|---|---|---|
| b-1 | 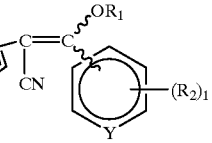 | ─CSOCH₃ |  | |
| b-2 | 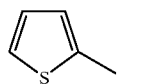 | ─CSOCH₂CH₃ | 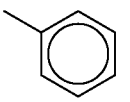 2-Cl | |
| b-3 | 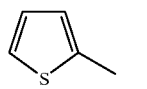 | ─CSO─Ph | 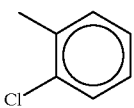 3-Cl | |
| b-4 | 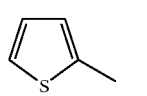 | ─CSCH₃ |  2-CF₃ | |
| b-5 | 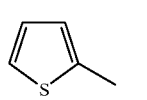 | ─CSCH₂CH₃ | 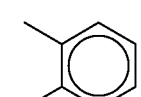 2-CF₃ | |
| b-6 | 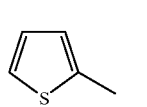 | ─CSCH₂CH=CH₂ | 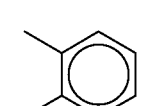 2-CF₃ | |
| b-7 |  | ─CSCH₂C≡Cl | 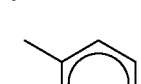 2-CF₃ | |
| b-8 | 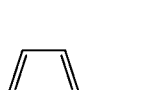 | ─CSOCH₃ | 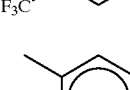 2-CF₃ | |
| b-9 | 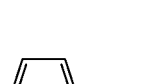 | ─CSOCH₂CH₃ | 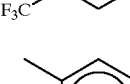 2-CF₃ | |
| b-10 | 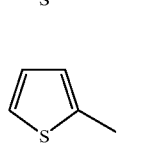 | ─CSOCH₂CH=CH₂ | 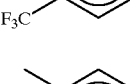 2-CF₃ | |

TABLE I-b-continued
(Ib)
| Comp. No. | (R₃)ₙ—[thiophene]— | R₁ | —[phenyl]—(R₂)₁ with Y | Physical property (Melting point) |
|---|---|---|---|---|
| b-11 |  | —CSOCH₂C≡Cl | 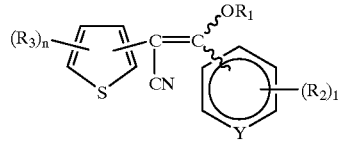 | |
| b-12 |  | —CS₂CH₃ | 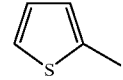 | $n_D^{38.2}$ 1.5888 |
| b-13 | 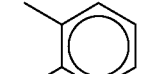 | —CS₂CH₂CH₃ | 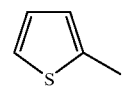 | 106.2° C. |
| b-14 | 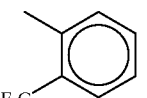 | —CS₂CH₂CH=CH₂ | 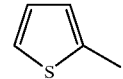 | |
| b-15 | 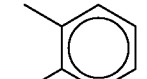 | —CS₂CH₂C≡Cl | 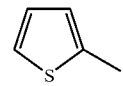 | |
| b-16 | 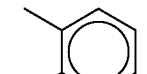 | —CS—<cyclopentyl> | 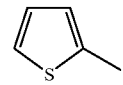 | |
| b-17 | 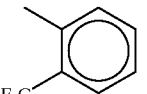 | —CSO—<cyclopentyl> | 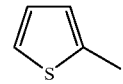 | |
| b-18 | 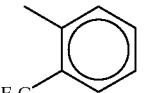 | —CS₂—<cyclopentyl> | 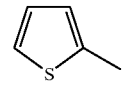 | |
| b-19 | 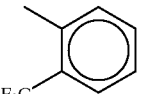 | —CS—<phenyl> | 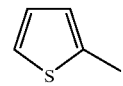 | |
| b-20 | 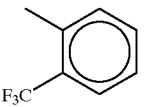 | —CS—<phenyl>—Cl | 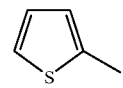 | |

TABLE I-b-continued (Ib)

| Comp. No. | (R₃)ₙ─⟨thiophene⟩ | R₁ | ⟨phenyl(R₂)₁, Y⟩ | Physical property (Melting point) |
|---|---|---|---|---|
| b-21 | 2-thienyl | —CSO—Ph | 2-CH₃-6-CF₃-phenyl | Oily |
| b-22 | 2-thienyl | —CS₂—Ph | 2-CH₃-6-CF₃-phenyl | |
| b-23 | 2-thienyl | —CSCH₂—Ph | 2-CH₃-6-CF₃-phenyl | |
| b-24 | 2-thienyl | —CSOCH₂—Ph | 2-CH₃-6-CF₃-phenyl | |
| b-25 | 2-thienyl | —CS₂CH₂—Ph | 2-CH₃-6-CF₃-phenyl | |
| b-26 | 2-thienyl | —CS₂—(oxazol-2-yl) | 2-CH₃-6-CF₃-phenyl | |
| b-27 | 2-thienyl | —CS₂—(thiazol-2-yl) | 2-CH₃-6-CF₃-phenyl | |
| b-28 | 2-thienyl | —CS₂—(oxazol-4-yl) | 2-CH₃-6-CF₃-phenyl | |
| b-29 | 2-thienyl | —CS₂—(thiazol-4-yl) | 2-CH₃-6-CF₃-phenyl | |

TABLE I-b-continued (Ib)

| Comp. No. | (R₃)ₙ─⟨thiophene⟩─ | R₁ | ⟨phenyl⟩(R₂)₁/Y | Physical property (Melting point) |
|---|---|---|---|---|
| b-30 | 2-thienyl | —CS₂-(isoxazol-5-yl) | 2-methyl-6-CF₃-phenyl | |
| b-31 | 2-thienyl | —CS₂-(isothiazol-5-yl) | 2-methyl-6-CF₃-phenyl | |
| b-32 | 2-thienyl | —CS₂-(pyrimidin-2-yl) | 2-methyl-6-CF₃-phenyl | |
| b-33 | 2-thienyl | —CS₂-(pyridazin-3-yl) | 2-methyl-6-CF₃-phenyl | |
| b-34 | 2-thienyl | —CS₂-(pyrazin-2-yl) | 2-methyl-6-CF₃-phenyl | |
| b-35 | 2-thienyl | —CS₂-(1,3,5-triazin-2-yl) | 2-methyl-6-CF₃-phenyl | |
| b-36 | 2-thienyl | —COSCH₃ | 2-methyl-6-CF₃-phenyl | |
| b-37 | 2-thienyl | —COSCH₂CH₃ | 2-methyl-6-CF₃-phenyl | |
| b-38 | 2-thienyl | —COSCH₂CH=CH₂ | 2-methyl-6-CF₃-phenyl | |
| b-39 | 2-thienyl | —COSCH₂C≡Cl | 2-methyl-6-CF₃-phenyl | |

TABLE I-b-continued
(Ib)
| Comp. No. | (R3)n-thiophene | R1 | phenyl-(R2)1-Y | Physical property (Melting point) |
|---|---|---|---|---|
| b-40 | 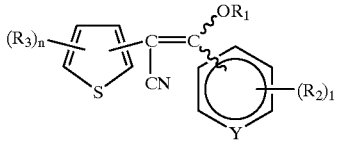 | —COS-cyclopentyl 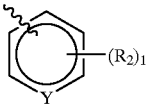 | 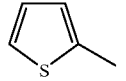 | |
| b-41 | 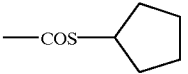 Cl | —CSOCH₃ | 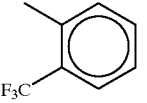 | |
| b-42 |  Br | —CSOCH₂CH₃ | 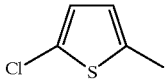 | |
| b-43 | 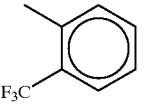 H₃C | —CS₂CH₃ | 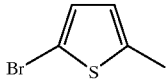 | |
| b-44 |  F₂HC | —CS₂CH₂CH₃ | 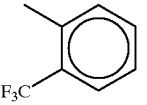 | |
| b-45 | 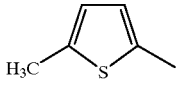 H₃CO | —CS₂CH₂CH=CH₂ |  | |
| b-46 | 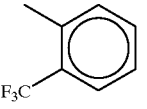 O₂N | —CSO-phenyl 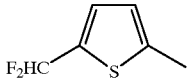 | 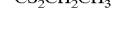 | |
| b-47 | 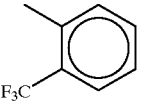 Cl | —COSCH₃ | 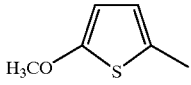 | |
| b-48 |  Br | —COSCH₂CH₃ | 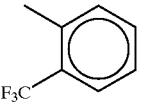 | |

TABLE I-b-continued
(Ib)
| Comp. No. |  | R₁ | 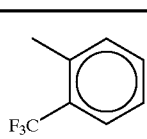 | Physical property (Melting point) |
|---|---|---|---|---|
| b-49 | 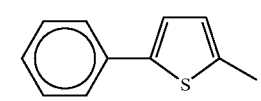 | —COSCH$_2$CH=CH$_2$ |  | |
| b-50 | 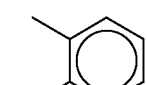 | —COSCH$_2$C≡Cl | 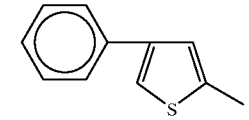 | |
| b-51 |  | —COS-cyclopentyl | 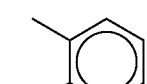 | |
TABLE I-c
(Ic)
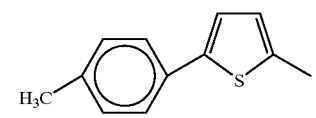
| Comp. No. | 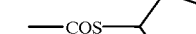 | R₁ | 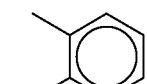 | Physical property (Melting point) |
|---|---|---|---|---|
| c-1 | 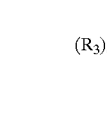 | —COCH$_3$ |  | 120~123° C. |
| c-2 | 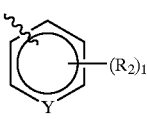 | —COCH$_3$ | 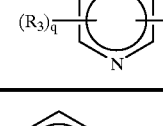 | |
| c-3 |  | —COCH$_2$CH$_3$ | 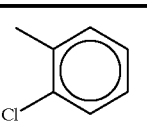 | |

TABLE I-c-continued (Ic)

| Comp. No. | (R3)q-pyridine | R1 | Y-phenyl-(R2)l | Physical property (Melting point) |
|---|---|---|---|---|
| c-4 | 2-methylpyridine | —CO(CH$_2$)$_2$CH$_3$ | 2-methyl-6-CF$_3$-phenyl | |
| c-5 | 2-methylpyridine | —COCH(CH$_3$)$_2$ | 2-methyl-6-CF$_3$-phenyl | |
| c-6 | 2-methylpyridine | —COC(CH$_3$)$_3$ | 2-methyl-6-Cl-phenyl | 93~95° C. |
| c-7 | 2-methylpyridine | —COC(CH$_3$)$_3$ | 2-methyl-6-CF$_3$-phenyl | |
| c-8 | 2-methylpyridine | —CON(CH$_3$)$_2$ | 2-methyl-6-Cl-phenyl | Oily |
| c-9 | 2-methylpyridine | —SO$_2$CH$_3$ | 2-methyl-6-CF$_3$-phenyl | |
| c-10 | 2-methylpyridine | —SO$_2$CH$_2$CH$_3$ | 2-methyl-6-CF$_3$-phenyl | |
| c-11 | 2-methylpyridine | —SO$_2$(CH$_2$)$_2$CH$_3$ | 2-methyl-6-CF$_3$-phenyl | |
| c-12 | 5-Cl-2-methylpyridine | —COCH$_3$ | 2-methyl-6-CF$_3$-phenyl | |
| c-13 | 6-Cl-2-methylpyridine | —COCH$_3$ | 2-methyl-6-Cl-phenyl | 101~102° C. |

TABLE I-c-continued
(Ic)
| Comp. No. | 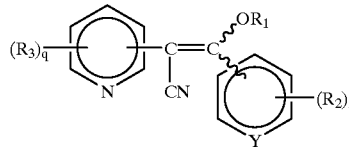 (R₃)q | R₁ | 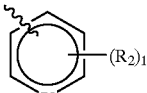 (R₂)l | Physical property (Melting point) |
|---|---|---|---|---|
| c-14 | 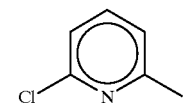 | —COCH₃ | 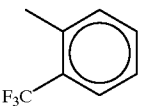 | |
| c-15 | 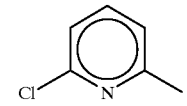 | —COCH₂CH₃ | 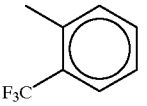 | |
| c-16 | 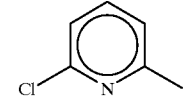 | —CO(CH₂)₂CH₃ | 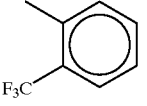 | |
| c-17 | 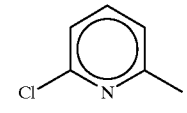 | —COCH(CH₃)₂ | 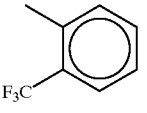 | |
| c-18 | 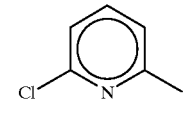 | —COC(CH₃)₃ | 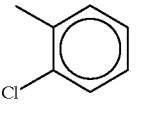 | 139~140° C. |
| c-19 | 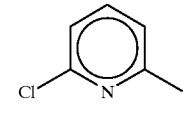 | —COC(CH₃)₃ | 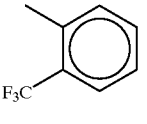 | |
| c-20 | 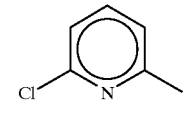 | —SO₂CH₃ | 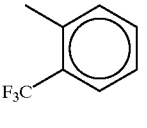 | |
| c-21 | 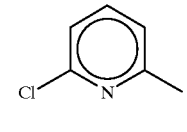 | —SO₂CH₂CH₃ | 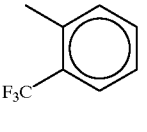 | |
| c-22 | 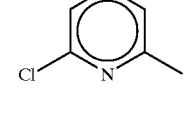 | —SO₂(CH₂)₂CH₃ | 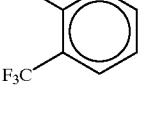 | |

TABLE I-c-continued

| Comp. No. | (R3)q—pyridine | R1 | Y—phenyl(R2)l | Physical property (Melting point) |
|---|---|---|---|---|
| c-23 | 5-Cl, 2-Me pyridine | —SO2CH3 | 2-Me, 6-CF3 phenyl | |
| c-24 | 2-Cl, 5-Me pyridine | —COCH3 | 2-Me, 6-CF3 phenyl | |
| c-25 | 2-Cl, 5-Me pyridine | —COCH2CH3 | 2-Me, 6-CF3 phenyl | |
| c-26 | 2-Cl, 5-Me pyridine | —CO(CH2)2CH3 | 2-Me, 6-CF3 phenyl | |
| c-27 | 2-Cl, 5-Me pyridine | —COCH(CH3)2 | 2-Me, 6-CF3 phenyl | |
| c-28 | 2-Cl, 5-Me pyridine | —COC(CH3)3 | 2-Me, 6-CF3 phenyl | |
| c-29 | 2-Cl, 5-Me pyridine | —SO2CH3 | 2-Me, 6-CF3 phenyl | |
| c-30 | 2-Cl, 5-Me pyridine | —SO2CH2CH3 | 2-Me, 6-CF3 phenyl | |
| c-31 | 2-Cl, 5-Me pyridine | —SO2(CH2)2CH3 | 2-Me, 6-CF3 phenyl | |
| c-32 | 5-Cl, 2-Me pyridine | —SO2CH2CH3 | 2-Me, 6-CF3 phenyl | |

TABLE I-c-continued
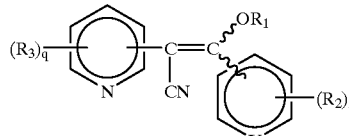
(Ic)
| Comp. No. | 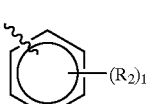 | R₁ | 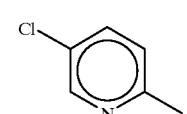 | Physical property (Melting point) |
|---|---|---|---|---|
| c-33 | 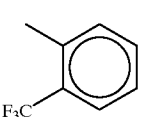 | —SO₂N(CH₃)₂ | 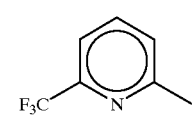 | |
| c-34 | 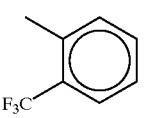 | —COCH₃ | 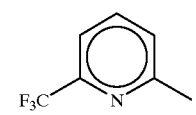 | 72~73° C. |
| c-35 | 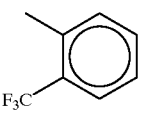 | —COCH₂CH₃ | 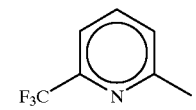 | |
| c-36 | 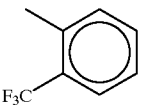 | —CO(CH₂)₂CH₃ | 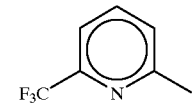 | |
| c-37 | 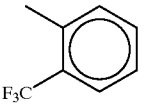 | —COCH(CH₃)₂ | 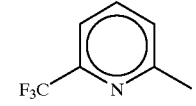 | |
| c-38 | 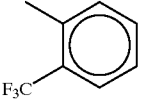 | —COC(CH₃)₃ | 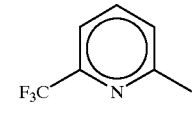 | |
| c-39 | 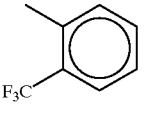 | —SO₂CH₃ | 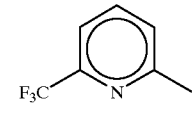 | |
| c-40 | 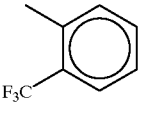 | —SO₂CH₂CH₃ | 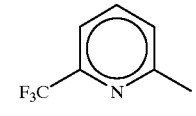 | |
| c-41 | | SO₂(CH₂)₂CH₃ | 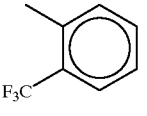 | |

TABLE I-c-continued
(Ic)
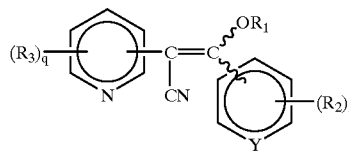
| Comp. No. | (R₃)q― pyridine ―  | R₁ | ―Y (R₂)₁ ring | Physical property (Melting point) |
|---|---|---|---|---|
| c-42 | 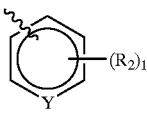 | —SO₂N(CH₃)₂ | 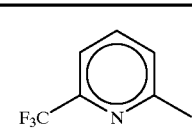 | 121~123° C. |
| c-43 | 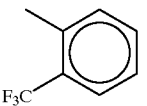 | —SO₂N(CH₃)₂ | 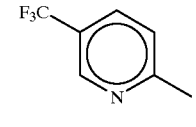 | 205~207° C. |
| c-44 | 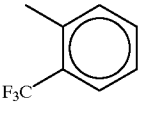 | —COCH₃ | 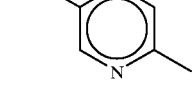 | 198~200° C. |
| c-45 | 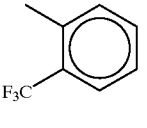 | —COCH₂CH₃ | 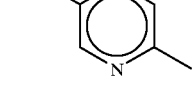 | |
| c-46 | 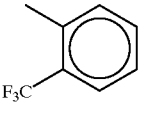 | —CO(CH₂)₂CH₃ | 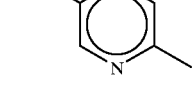 | |
| c-47 | 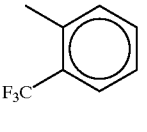 | —COCH(CH₃)₂ | 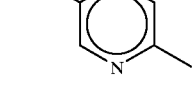 | |
| c-48 | 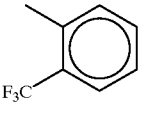 | —COC(CH₃)₃ | 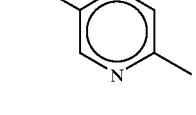 | |
| c-49 | 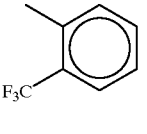 | —SO₂CH₃ | 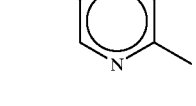 | |
| c-50 | 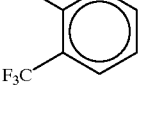 | —SO₂CH₂CH₃ | 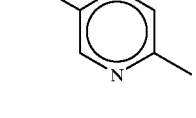 | |

TABLE I-c-continued

| Comp. No. | (R3)q-pyridine | R1 | Y-ring with (R2)l | Physical property (Melting point) |
|---|---|---|---|---|
| c-51 | 5-CF3, 2-methyl pyridine | —SO2(CH2)2CH3 | 2-methyl, 3-CF3 phenyl | |
| c-52 | 6-methyl, 2-phenyl pyridine | —COCH3 | 2-methyl, 3-Cl phenyl | |
| c-53 | 6-methyl, 2-phenyl pyridine | —COCH3 | 2-methyl, 3-CF3 phenyl | |
| c-54 | 6-methyl, 2-phenyl pyridine | —COCH2CH3 | 2-methyl, 3-CF3 phenyl | |
| c-55 | 6-methyl, 2-phenyl pyridine | —CO(CH2)2CH3 | 2-methyl, 3-CF3 phenyl | |
| c-56 | 6-methyl, 2-phenyl pyridine | —COCH(CH3)2 | 2-methyl, 3-CF3 phenyl | |
| c-57 | 6-methyl, 2-phenyl pyridine | —COC(CH3)3 | 2-methyl, 3-CF3 phenyl | |
| c-58 | 6-methyl, 2-phenyl pyridine | —SO2CH3 | 2-methyl, 3-CF3 phenyl | |

TABLE I-c-continued

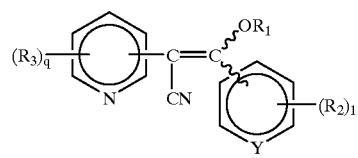
(Ic)

| Comp. No. | (R₃)q—[pyridine]— | R₁ | —[Y ring]—(R₂)l | Physical property (Melting point) |
|---|---|---|---|---|
| c-59 | 6-methyl-2-phenylpyridin-3-yl | —SO₂CH₂CH₃ | 2-(trifluoromethyl)phenyl | |
| c-60 | 6-methyl-2-phenylpyridin-3-yl | —SO₂(CH₂)₂CH₃ | 2-(trifluoromethyl)phenyl | |
| c-61 | 2-chloro-3-methylpyridin-... | —CO-(2,6-difluorophenyl) | 2,6-difluoro-3-methylphenyl | Z-isomer 116~120° C. |
| c-62 | 6-chloro-3-methylpyridin-... | —CO-(2-chlorophenyl) | 2-chloro-...phenyl | Oily |
| c-63 | 2-chloro-3-methylpyridin-... | —CO-(2,6-difluorophenyl) | 2,6-difluoro-3-methylphenyl | E-isomer 171~176° C. |
| c-64 | 6-chloro-3-methylpyridin-... | —CO-(2,6-difluorophenyl) | 2,6-difluoro-3-methylphenyl | 138~142° C. |
| c-65 | 2-(4-chlorophenyl)-6-methylpyridin-... | —SO₂N(CH₂CH₃)₂ | 2-(trifluoromethyl)phenyl | |

TABLE I-d
(Id)
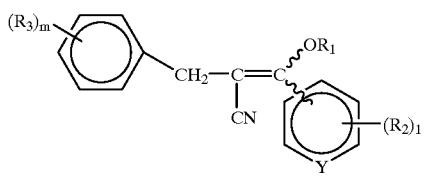
| Comp. No. | (R₃)ₘ-⌬-CH₂- | R₁ | ⌬-(R₂)ₗ / Y | Physical property (Melting point) |
|---|---|---|---|---|
| d-1 |  | —COCH₃ | 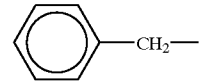 | |
| d-2 | 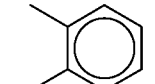 | —CO₂CH₃ | 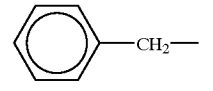 | |
| d-3 | 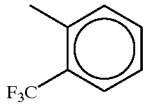 | —CS₂CH₃ | 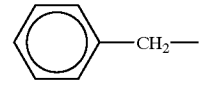 | E-isomer $n_D^{39.2}$ 1.5352 |
| d-4 | 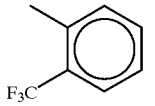 | —CS₂CH₃ | 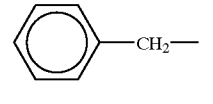 | Z-isomer $n_D^{39.2}$ 1.5651 |
| d-5 | 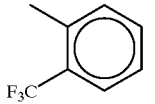 | —CS₂CH₂CH₃ | 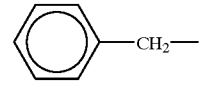 | |
| d-6 | 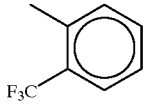 | —SO₂N(CH₃)₂ | 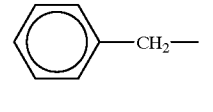 | |
| d-7 | 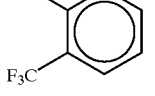 | —SO₂N(CH₂CH₃)₂ | 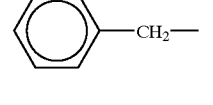 | |
| d-8 | 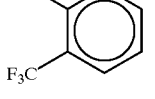 | —COCH₃ | 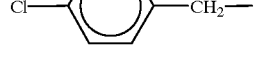 | |
| d-9 | 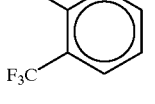 | —CO₂CH₃ |  | |

TABLE I-d-continued

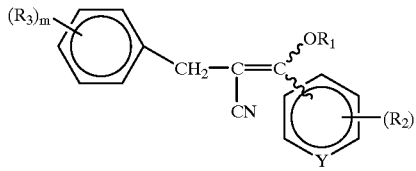

| Comp. No. | (R₃)ₘ-Ph-CH₂- | R₁ | Y ring (R₂)ₗ | Physical property (Melting point) |
|---|---|---|---|---|
| d-10 | 4-Cl-C₆H₄-CH₂- | —CS₂CH₃ | 2-CH₃-6-CF₃-phenyl | |
| d-11 | 4-Cl-C₆H₄-CH₂- | —CS₂CH₂CH₃ | 2-CH₃-6-CF₃-phenyl | |
| d-12 | 4-Cl-C₆H₄-CH₂- | —SO₂N(CH₃)₂ | 2-CH₃-6-CF₃-phenyl | |
| d-13 | 4-Cl-C₆H₄-CH₂- | —SO₂N(CH₂CH₃)₂ | 2-CH₃-6-CF₃-phenyl | |
| d-14 | 4-Br-C₆H₄-CH₂- | —COCH₃ | 2-CH₃-6-CF₃-phenyl | |
| d-15 | 4-Br-C₆H₄-CH₂- | —CO₂CH₃ | 2-CH₃-6-CF₃-phenyl | |
| d-16 | 4-Br-C₆H₄-CH₂- | —CS₂CH₃ | 2-CH₃-6-CF₃-phenyl | |
| d-17 | 4-Br-C₆H₄-CH₂- | —CS₂CH₂CH₃ | 2-CH₃-6-CF₃-phenyl | |
| d-18 | 4-Br-C₆H₄-CH₂- | —SO₂N(CH₃)₂ | 2-CH₃-6-CF₃-phenyl | |

TABLE I-d-continued (Id)

| Comp. No. | (R₃)ₘ—⌬—CH₂— | R₁ | ⌬—(R₂)₁ / Y | Physical property (Melting point) |
|---|---|---|---|---|
| d-19 | Br—⌬—CH₂— | —SO₂N(CH₂CH₃)₂ | 2-CH₃, 6-CF₃ phenyl | |
| d-20 | F—⌬—CH₂— | —COCH₃ | 2-CH₃, 6-CF₃ phenyl | |
| d-21 | F—⌬—CH₂— | —CO₂CH₃ | 2-CH₃, 6-CF₃ phenyl | |
| d-22 | F—⌬—CH₂— | —CS₂CH₃ | 2-CH₃, 6-CF₃ phenyl | |
| d-23 | F—⌬—CH₂— | —CS₂CH₂CH₃ | 2-CH₃, 6-CF₃ phenyl | |
| d-24 | F—⌬—CH₂— | —SO₂N(CH₃)₂ | 2-CH₃, 6-CF₃ phenyl | |
| d-25 | F—⌬—CH₂— | —SO₂N(CH₂CH₃)₂ | 2-CH₃, 6-CF₃ phenyl | |
| d-26 | 2,4-Cl₂-C₆H₃-CH₂— | —COCH₃ | 2-CH₃, 6-CF₃ phenyl | |
| d-27 | 2,4-Cl₂-C₆H₃-CH₂— | —CO₂CH₃ | 2-CH₃, 6-CF₃ phenyl | |

TABLE I-d-continued
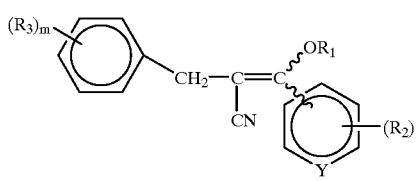
(Id)
| Comp. No. |  | $R_1$ | 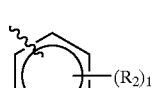 Y | Physical property (Melting point) |
|---|---|---|---|---|
| d-28 | 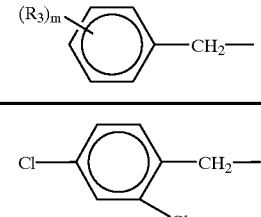 | —CS$_2$CH$_3$ | 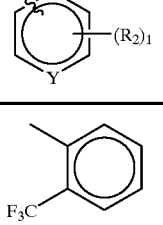 | |
| d-29 | 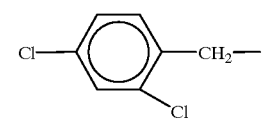 | —CS$_2$CH$_2$CH$_3$ | 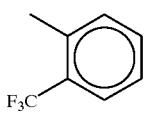 | |
| d-30 | 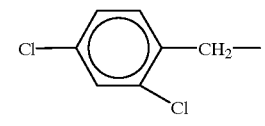 | —SO$_2$N(CH$_3$)$_2$ | 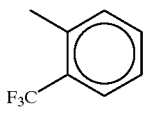 | |
| d-31 | 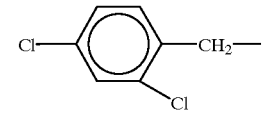 | —SO$_2$N(CH$_2$CH$_3$)$_2$ | 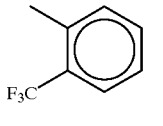 | |
| d-32 | 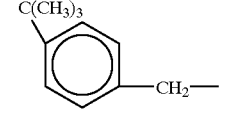 | —COCH$_3$ | 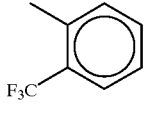 | |
| d-33 | 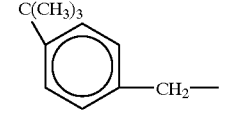 | —CO$_2$CH$_3$ | 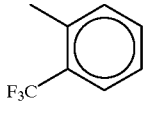 | |
| d-34 | 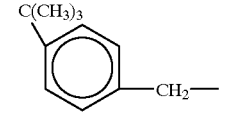 | —CS$_2$CH$_3$ | 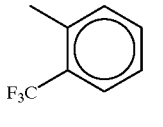 | |
| d-35 | 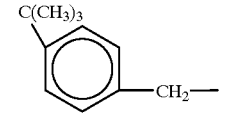 | —CS$_2$CH$_2$CH$_3$ | 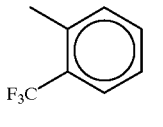 | |
| d-36 | 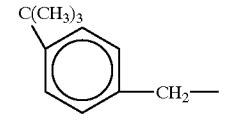 | —SO$_2$N(CH$_3$)$_2$ | 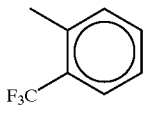 | |

TABLE I-d-continued
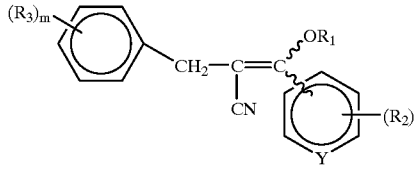
(Id)
| Comp. No. |  | $R_1$ | 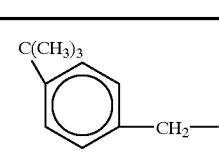 | Physical property (Melting point) |
|---|---|---|---|---|
| d-37 | 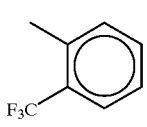 | —SO$_2$N(CH$_2$CH$_3$)$_2$ | 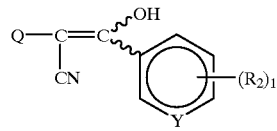 | |
TABLE 2
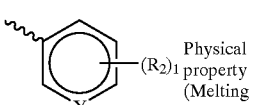
(II)
| Intermediate No. | Q | 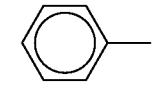 | Physical property (Melting point) |
|---|---|---|---|
| II-1 | 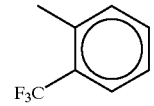 | 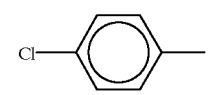 | 154~156° C. |
| II-2 | 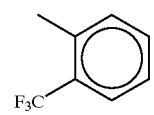 | 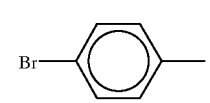 | 146~148° C. |
| II-3 | 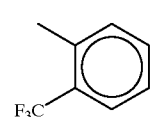 | 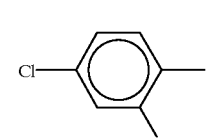 | 168~173° C. |
| II-4 | 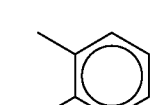 | 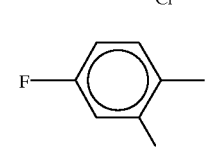 | 182~183° C. |
| II-5 | 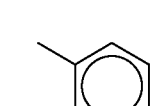 | | |

TABLE 2-continued (II)

$$Q-C(CN)=C(OH)-[Ar(R_2)_1 Y]$$

| Intermediate No. | Q | [Ar(R$_2$)$_1$ Y] | Physical property (Melting point) |
|---|---|---|---|
| II-6 | 4-F, 3-Cl-phenyl | 2-CF$_3$-phenyl | 120~130° C. |
| II-7 | pentafluorophenyl | 2-CF$_3$-phenyl | |
| II-8 | 4-CF$_3$-phenyl | 2-CF$_3$-phenyl | 164~167° C. |
| II-9 | 4-CF$_3$, 3-Cl-phenyl | 2-CF$_3$-phenyl | |
| II-10 | 4-CF$_3$, 3-F-phenyl | 2-CF$_3$-phenyl | |
| II-11 | 4-O$_2$N-phenyl | 2-CF$_3$-phenyl | 145~150° C. |
| II-12 | 4-Cl, 3-NO$_2$-phenyl | 2-CF$_3$-phenyl | 175~177° C. |
| II-13 | 4-O$_2$N, 3-Cl-phenyl | 2-CF$_3$-phenyl | |

TABLE 2-continued (II)

| Intermediate No. | Q | ~(R₂)₁ Y | Physical property (Melting point) |
|---|---|---|---|
| II-14 | H₃CS-C₆H₂(Cl)(CH₃)- | 2-CF₃-C₆H₄- | |
| II-15 | H₃CO₂S-C₆H₂(Cl)(CH₃)- | 2-CF₃-C₆H₄- | |
| II-16 | C₆H₅O-C₆H₂(Cl)(CH₃)- | 2-CF₃-C₆H₄- | |
| II-17 | 2-Cl-C₆H₄- | 2-CF₃-C₆H₄- | 187~189° C. |
| II-18 | 3-Cl-C₆H₄- | 2-CF₃-C₆H₄- | 118~121° C. |
| II-19 | 4-F-C₆H₄- | 2-CF₃-C₆H₄- | 139~144° C. |
| II-20 | 4-I-C₆H₄- | 2-CF₃-C₆H₄- | 170~180° C. |
| II-21 | 3,4-Cl₂-C₆H₃- | 2-CF₃-C₆H₄- | 188~189° C. |
| II-22 | 4-Cl-2-F-C₆H₃- | 2-CF₃-C₆H₄- | 176~180° C. |

TABLE 2-continued (II)

| Intermediate No. | Q | (R₂)₁ Y | Physical property (Melting point) |
|---|---|---|---|
| II-23 | H₃C—⌬— | 2-CH₃, 6-CF₃ phenyl | 87~90° C. |
| II-24 | (H₃C)₂CH—⌬— | 2-CH₃, 6-CF₃ phenyl | |
| II-25 | (H₃C)₃C—⌬— | 2-CH₃, 6-CF₃ phenyl | 156~158° C. |
| II-26 | H₃CO—⌬— | 2-CH₃, 6-CF₃ phenyl | 90~92° C. |
| II-27 | NC—⌬— | 2-CH₃, 6-CF₃ phenyl | |
| II-28 | F₃CO—⌬— | 2-CH₃, 6-CF₃ phenyl | |
| II-29 | H₃COS—⌬— | 2-CH₃, 6-CF₃ phenyl | |
| II-30 | ⌬—⌬— | 2-CH₃, 6-CF₃ phenyl | |
| II-31 | Cl—⌬—O—⌬— | 2-CH₃, 6-CF₃ phenyl | |
| II-32 | H₃C—⌬—O—⌬— | 2-CH₃, 6-CF₃ phenyl | |

TABLE 2-continued (II)

Structure: Q-C(CN)=C(OH)-Ar where Ar is a phenyl ring Y with (R₂)₁ substituents

| Intermediate No. | Q | Ar (with (R₂)₁, Y) | Physical property (Melting point) |
|---|---|---|---|
| II-33 | 4-Cl-C₆H₄- | 2-methyl-6-(CHF₂)-phenyl | |
| II-34 | 4-Cl-C₆H₄- | 2-methyl-6-(CH₂F)-phenyl | |
| II-35 | 4-Cl-C₆H₄- | 2-methyl-3-Cl-6-(CF₃)-phenyl | |
| II-36 | 4-Cl-C₆H₄- | 2-methyl-3-OCH₃-6-(CF₃)-phenyl | |
| II-37 | 4-Cl-C₆H₄- | 2-methyl-3-SCH₃-6-(CF₃)-phenyl | |
| II-38 | 4-Cl-C₆H₄- | 2-methyl-3-SO₂CH₃-6-(CF₃)-phenyl | |
| II-39 | 4-Cl-C₆H₄- | 2-methyl-3-CF₃-6-(CF₃)-phenyl | |
| II-40 | 4-Cl-C₆H₄- | 2-methyl-3-F-6-(CF₃)-phenyl | |

TABLE 2-continued (II) Structure: Q-C(=C-OH)(CN)-[Ar(R₂)₁ with Y]

| Intermediate No. | Q | Ar(R₂)₁ with Y | Physical property (Melting point) |
|---|---|---|---|
| II-41 | 4-Cl-C₆H₄- | 2-CH₃-4-F-5-CF₃-C₆H₂- | |
| II-42 | 4-Cl-C₆H₄- | 2-CH₃-4-CF₃-5-CF₃-C₆H₂- (2,5-bis-CF₃-4-CH₃) | |
| II-43 | 4-Cl-C₆H₄- | 2,3-(CH₃)-6-CF₃-C₆H₂- | |
| II-44 | 4-(C₆H₅O)-C₆H₄- | 2-CH₃-6-CF₃-C₆H₃- | |
| II-45 | 4-(SCHF₂)-C₆H₄- | 2-CH₃-6-CF₃-C₆H₃- | |
| II-46 | 4-(OCHF₂)-C₆H₄- | 2-CH₃-6-CF₃-C₆H₃- | |
| II-47 | 4-Cl-2-CH₃-C₆H₃- | 2-CH₃-6-CF₃-C₆H₃- | |
| II-48 | 4-(CH=CCl₃)-C₆H₄- | 2-CH₃-6-CF₃-C₆H₃- | |
| II-49 | 4-(CH=CF₂)-C₆H₄- | 2-CH₃-6-CF₃-C₆H₃- | |

TABLE 2-continued (II)

| Intermediate No. | Q | (ring with Y and (R₂)₁) | Physical property (Melting point) |
|---|---|---|---|
| II-50 | 4-(SCF₃)-C₆H₄- | 2-CH₃-6-(CF₃)-C₆H₃- | |
| II-51 | 4-(SOCF₃)-C₆H₄- | 2-CH₃-6-(CF₃)-C₆H₃- | |
| II-52 | 4-(SO₂CF₃)-C₆H₄- | 2-CH₃-6-(CF₃)-C₆H₃- | |
| II-53 | 4-(C≡Cl)-C₆H₄- | 2-CH₃-6-(CF₃)-C₆H₃- | |
| II-54 | 4-Cl-C₆H₄-S-C₆H₄-4-CH₃ | 2-CH₃-6-(CF₃)-C₆H₃- | |
| II-55 | 4-Cl-C₆H₄-SO-C₆H₄-4-CH₃ | 2-CH₃-6-(CF₃)-C₆H₃- | |
| II-56 | 4-Cl-C₆H₄-SO₂-C₆H₄-4-CH₃ | 2-CH₃-6-(CF₃)-C₆H₃- | |
| II-57 | 4-(OCH₂CH=CCl₂)-C₆H₄- | 2-CH₃-6-(CF₃)-C₆H₃- | |
| II-58 | 4-(OCH₂C≡Cl)-C₆H₄- | 2-CH₃-6-(CF₃)-C₆H₃- | |

TABLE 2-continued
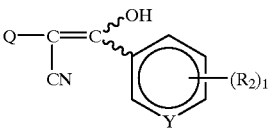
| Intermediate No. | Q | 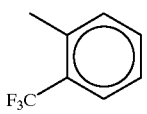 | Physical property (Melting point) |
|---|---|---|---|
| II-59 | 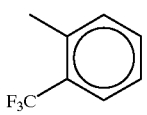 SCH₂CH=CCl₂ | 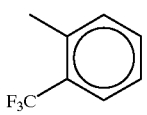 | |
| II-60 | 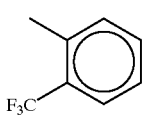 SCH₂C≡Cl | 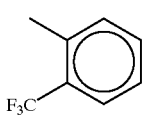 | |
| II-61 | 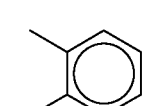 SOCH₂CH=CCl₂ | 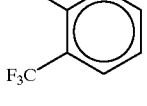 | |
| II-62 | 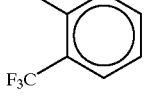 SO₂CH₂CH=CCl₂ | 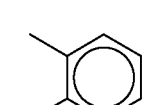 | |
| II-63 | 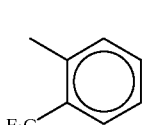 SOCH₂C≡Cl | 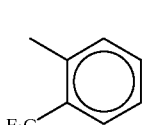 | |
| II-64 | 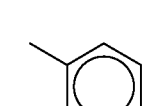 SO₂CH₂C≡Cl | 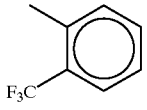 | |
| II-65 | 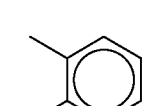 | 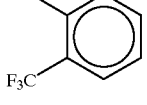 | |
| II-66 | 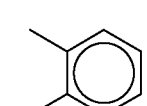 | | |
| II-67 | 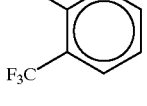 |  | |

TABLE 2-continued (II)

| Intermediate No. | Q | (R₂)₁ ring | Physical property (Melting point) |
|---|---|---|---|
| II-68 | benzyl-(4-methylphenyl)methyl (Ph-CH₂-C₆H₄-) | 2-CF₃, 6-CH₃ phenyl | |
| II-69 | 2-methylthiophene (thien-2-yl, 5-Me) | 2-CF₃, 6-CH₃ phenyl | 105~108° C. |
| II-70 | 5-chloro-2-methylthiophene | 2-CF₃, 6-CH₃ phenyl | |
| II-71 | 5-bromo-2-methylthiophene | 2-CF₃, 6-CH₃ phenyl | |
| II-72 | 2,5-dimethylthiophene | 2-CF₃, 6-CH₃ phenyl | |
| II-73 | 5-(difluoromethyl)-2-methylthiophene | 2-CF₃, 6-CH₃ phenyl | |
| II-74 | 5-methoxy-2-methylthiophene | 2-CF₃, 6-CH₃ phenyl | |
| II-75 | 5-nitro-2-methylthiophene | 2-CF₃, 6-CH₃ phenyl | |
| II-76 | 5-phenyl-2-methylthiophene | 2-CF₃, 6-CH₃ phenyl | |

TABLE 2-continued

| Intermediate No. | Q | Y-Ar(R₂)₁ | Physical property (Melting point) |
|---|---|---|---|
| II-77 | 4-phenyl-2-thienyl | 2-(trifluoromethyl)phenyl | |
| II-78 | 5-(4-methylphenyl)-2-thienyl | 2-(trifluoromethyl)phenyl | |
| II-79 | 5-chloro-2-pyridyl | 2-(trifluoromethyl)phenyl | |
| II-80 | 6-chloro-2-pyridyl | 2-(trifluoromethyl)phenyl | |
| II-81 | 6-chloro-3-pyridyl | 2-(trifluoromethyl)phenyl | |
| II-82 | 6-(trifluoromethyl)-2-pyridyl | 2-(trifluoromethyl)phenyl | 115~119° C. |
| II-83 | 5-(trifluoromethyl)-2-pyridyl | 2-(trifluoromethyl)phenyl | 206~213° C. |
| II-84 | 6-phenyl-2-pyridyl | 2-(trifluoromethyl)phenyl | |
| II-85 | 6-(4-chlorophenyl)-2-pyridyl | 2-(trifluoromethyl)phenyl | |

TABLE 2-continued

| Intermediate No. | Q | 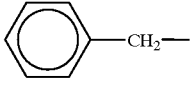 | Physical property (Melting point) |
|---|---|---|---|
| II-86 | 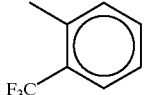 | 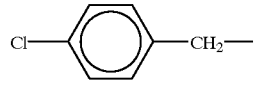 | |
| II-87 | 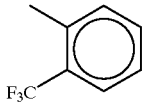 | 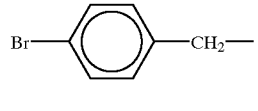 | |
| II-88 | 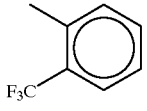 | 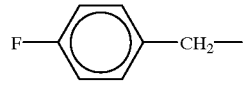 | |
| II-89 | 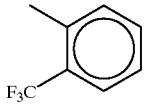 | 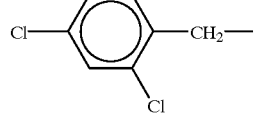 | |
| II-90 | 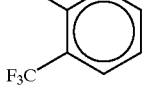 | 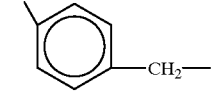 | |
| II-91 | 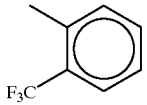 | | |

Now, Test Examples will be described.

TEST EXAMPLE 1

Miticidal test against adults of two-spotted spider mite (*Tetranychus urticae*)

A miticidal solution was prepared to bring the concentration of a compound of the present invention to 800 ppm. Kidney bean (*Phaseolus vulgaris*) seedling with only one primary leaf left, was transplanted in a cup (diameter: 8 cm, height: 7 cm) and 30 adults of two-spotted spider mite (*Tetranychus urticae*) were inoculated thereto. The adult mites were immersed together with the kidney bean leaf in the above miticidal solution for about 10 seconds, then dried in air and left in a constant temperature chamber at 26° C. with lightening. On the second day after the treatment, dead adult mites were counted, and the mortality was calculated by the following equation.

$$\text{Mortality (\%)} = \frac{\text{Number of dead adult mites}}{\text{Number of treated adult mites}} \times 100$$

As a result, the mortality was at least 90% with each of Compound Nos. a-6 to 7, a-10 to 14, a-20 to 25, a-29, a-31, a-39, a-43, a-46 to 48, a-55, a-63, a-67, a-72, a-77 to 78, a-80, a-83, a-97, a-99, a-153, a-156, a-160 to 164, a-166 to 167, a-173, a-175 to 181, a-183 to 189, a-191, a-194 to 197, a-200 to 202, a-206 to 207, a-209, a-211 to 212, a-214 to 215, a-218 to 221, a-223 to 224, a-227, a-230, a-240, a-244, a-245, a-250 to 251, a-254 to 258, a-260 to 263, a-267, a-274, a-286, a-288, a-290, a-298, a-300, a-303 to 308, a-310, a-316 to 319, a-322, a-323, a-325, a-328 to 329, a-331, a-335, a-342, a-359, a-360, a-362 to 363, a-365, a-367 to 368, a-371 to 373, a-375 to 376, a-381, a-382, a-384, a-386 to 388, a-390, a-392, a-394 to 395, a-398, a-403, a-413 to 414, a-417 to 418, a-425 to 426, a-428 to 431, a-434 to 435, a-443, a-445, a-451 to 452, a-459 to 463, a-465 to 467, a-469 to 472, a-474, a-475, a-573, a-574, a-637 to 641, a-664 to 667, a-686, c-34, c-43 and c-44 and with intermediate No. II-2.

TEST EXAMPLE 2

Ovicidal test against two-spotted spider mite (*Tetranychus urticae*)

An ovicidal solution was prepared to bring the concentration of a compound of the present invention to 800 ppm. Kidney bean (*Phaseolus vulgaris*) seedling with only one primary leaf left,. was transplanted in a cup (diameter: 8 cm, height: 7 cm), and adults of two-spotted spider mite (*Tetranychus urticae*) were inoculated thereto and permitted to lay eggs for 24 hours, whereupon the adult mites were removed. The eggs were dipped together with the kidney bean leaf in the above ovicidal solution for about 10 seconds, then dried in air and left in a constant temperature chamber at 26° C. with lightening. On the 7th day after the treatment, hatching of the eggs was investigated, and the ovicidal ratio was obtained by the following equation.

$$\text{Ovicidal ratio (\%)} = \frac{\text{Number of dead eggs}}{\text{Number of treated eggs}} \times 100$$

As a result, the ovicidal ratio was at least 90% with each of Compound Nos. a-10 to 14, a-20 to 25, a-29, a-31, a-38 to 39, a-43, a-46 to 48, a-55, a-63, a-67, a-70, a-72, a-77 to 78, a-80, a-83, a-97, a-99, a-150, a-156, a-160 to 164, a-166 to 168, a-173, a-175 to 181, a-183 to 189, a-191, a-194 to 197, a-200 to 202, a-204, a-206 to 207, a-209, a-211 to 212, a-214 to 215, a-218 to 221, a-223 to 224, a-227, a-230, a-233 to 234, a-240, a-244, a-245, a-250 to 251, a-254 to 258, a-260 to 262, a-267, a-274, a-282, a-286, a-288, a-298, a-300, a-303 to 308, a-310, a-316 to 319, a-322, a-323, a-325, a-328 to 329, a-331 to 333, a-335, a-337, a-342, a-348, a-359, a-360, a-362 to 363, a-365, a-367 to 368, a-371 to 372, a-375 to 376, a-381, a-382, a-384, a-386 to 388, a-390, a-394 to 395, a-399, a-403, a-407, a-413 to 414, a-417 to 418, a-425 to 426, a-428 to 431, a-434 to 435, a-443, a-445, a-451, a-452, a-456, a-459 to 463, a-465 to 467, a-470 to 472, a-474, a-475, a-573, a-574, a-637 to 641, a-662 to 667, a-686, c-34, c-43 and c-44.

TEST EXAMPLE 3

Insecticidal test against small brown planthopper (*Laodelphax striatellus*)

Rice seedling was dipped for about 10 seconds in an insecticidal solution prepared to bring the concentration of a compound of the present invention to 800 ppm and then dried in air. Then, the seedling with its root wrapped with a wet absorbent cotton, was put into a test tube. Then, 10 larvae of small brown planthopper (*Laodelphax striatellus*) were released therein, and the test tube was covered with a gauze and left in a constant chamber at 26° C. with lightening. On the 5th day after the release, dead larvae were counted, and the mortality was calculated by the following equation.

$$\text{Mortality (\%)} = \frac{\text{Number of dead insects}}{\text{Number of released insects}} \times 100$$

As a result, the mortality was at least 90% with each of Compound Nos. a-10 to 11, a-161, a-362, a-474, a-637, a-638 and c-34.

TEST EXAMPLE 4

Insecticidal test against green peach aphid (*Myzus persicae*)

An insecticidal solution was prepared to bring the concentration of a compound of the present invention to 800 pm. The petiole of each of eggplants with only one foliage leaf left (planted in a pot having a diameter of 8 cm and a height of 7 cm) was coated with a sticker, and about 2–3 apterous viviparous female of green peach aphid (*Myzus persicae*) were infested and incubated on the foliage leaf of the eggplant. After two days from the infestation, the adult insects were removed, and the number of larvae was counted. Then, the foliage leaf of the eggplant infested with the larvae was dipped in the above insecticidal solution for about 10 seconds, then dried in air and left in a constant temperature chamber at 26° C. with lightening. On the 5th day after the treatment, dead insects were counted, and the mortality was calculated by the following equation:

$$\text{Mortality (\%)} = \frac{\text{Number of dead insects}}{\text{Number of treated insects}} \times 100$$

The insects released from the leaf were counted as dead insects.

As a result, the mortality was at least 90% with each of Compound Nos. a-10 to 11, a-160 to 162, a-637 and a-638.

TEST EXAMPLE 5

Test on preventive effect against tomato late blight

Tomato (cultivar: Ponderosa) was cultivated in a polyethylene pot having a diameter of 7.5 cm. When the tomato reached a four-leaf stage, it was sprayed with 10 ml of a solution having a predetermined concentration of a compound of the present invention through a spray gun. After the solution was dried, the tomato plant was sprayed and inoculated with a zoosporangia suspension of fungi of late blight (*Phytophthora infestans*) and kept in a constant-temperature chamber at 20° C.

Third to fourth day after the inoculation, the area of lesions was examined, and the control index was determined according to the following criteria for evaluation.

| Control index | Degree of disease outbreak (visual observation) |
|---|---|
| 5 | No lesions are recognizable at all. |
| 4 | The area, number or length of lesions is less than 10% of that in the non-treated plot. |
| 3 | The area, number or length of lesions is less than 40% of that in the non-treated plot. |
| 2 | The area, number or length of lesions is less than 70% of that in the non-treated plot. |
| 1 | The area, number or length of lesions is 70% or more of that in the non-treated plot. |

As a result, Compound No. a-3 exhibited a control index of 5 at a concentration of 250 ppm.

TEST EXAMPLE 6

Test on preventive effect against wheat powdery mildew

Wheat (cultivar: Norin No. 61) was cultivated in a polyethylene pot having a diameter of 7.5 cm. When the wheat reached a 1.5 leaf stage, it was sprayed with 10 ml of a solution having a predetermined concentration of a compound of the present invention through a spray gun. After the solution was dried, the wheat was dusted and inoculated with conidia of fungi of powdery mildew (*Erysiphe graminis*) and kept in a constant-temperature chamber at 20° C.

Eighth day after the inoculation, the area of lesions or the spore-formation area was examined, and the control index was determined according to the following criteria for evaluation.

| Control index | Degree of disease outbreak (visual observation) |
|---|---|
| 5 | No lesion or spore-formation is recognizable at all. |
| 4 | The area or number of lesions or the spore-formation area is less than 10% of that in the non-treated plot. |
| 3 | The area or number of lesions or the spore-formation area is less than 40% of that in the non-treated plot. |
| 2 | The area or number of lesions or the spore-formation area is less than 70% of that in the non-treated plot. |
| 1 | The area or number of lesions or the spore-formation area is 70% or more of that in the non-treated plot. |

As a result, Compounds Nos. a-7, a-30, a-63, a-67, a-77 to 78, a-123 and a-234 exhibited a control index of 5 at a concentration of 500 pm, and Compounds Nos. a-3, a-38 to 39 and a-46 exhibited a control index of 5 or 4 at a concentration of 250 ppm.

TEST EXAMPLE 7
Test on preventive effect against oat crown rust

Oat (cultivar: Zenshin) was cultivated in a polyethylene pot having a diameter of 7.5 cm. When the oat reached a 1.5 leaf stage, it was sprayed with 10 ml of a solution having a predetermined concentration of a compound of the present invention through a spray gun.

After the solution was dried, the oat was sprayed and inoculated with a spore suspension of fungi of crown rust (*Puccinia coronata*). Eighth day after the inoculation, the area of lesions or spore-formation area was examined and the control index was determined in the same manner as in Test Example 6.

As a result, compound Nos. a-78, a-123 and a-166 exhibited a control index of 5 at a concentration of 500 ppm, and Compound No. a-3 exhibited a control index of 5 at a concentration of 250 ppm.

TEST EXAMPLE 8
Control test against green algae

Green algae preliminarily cultured for 7 days (① *Selenastrum capricornutum* or ②: *Chlorella vulgaris*) were inoculated to a culture medium for algae containing a solution prepared to bring the concentration of a compound of the present invention to 100 ppm, and left to stand for 8 days in a constant temperature chamber at 20° C. with lighting, whereupon growth degree of the green algae was investigated, and the control index was determined according to the following criteria for evaluation.

| Control index | Growth degree (visual observation) |
|---|---|
| A | No growth of green algae is observed at all |
| B | Growth of green algae is slightly observed. |
| C | Growth of green algae is observed in the same degree as in the non-treated plot. |

As a result, Compound Nos. a-3, a-6 and a-70 exhibited a control index of A against green algae ① at a concentration of 100 ppm. Further, against green algae ②, Compound Nos. a-3, a-6, a-26 and a-39 exhibited a control index of A at a concentration of 100 ppm.

Now, formulation Examples will be described.

FORMULATION EXAMPLE 1

| | |
|---|---|
| (a) Compound No. a-31 | 20 parts by weight |
| (b) Clay | 72 parts by weight |
| (c) Sodium lignin sulfonate | 8 parts by weight |

The above components are uniformly mixed to obtain a wettable powder.

FORMULATION EXAMPLE 2

| | |
|---|---|
| (a) Compound No. b-26 | 5 parts by weight |
| (b) Talc | 95 parts by weight |

The above components are uniformly mixed to obtain a dust.

FORMULATION EXAMPLE 3

| | |
|---|---|
| (a) Compound No. a-39 | 20 parts by weight |
| (b) N,N'-dimethylacetamide | 20 parts by weight |
| (c) Polyoxyethylenealkylphenyl ether | 10 parts by weight |
| (d) Xylene | 50 parts by weight |

The above components are uniformly mixed and dissolved to obtain an emulsifiable concentrate.

FORMULATION EXAMPLE 4

| | |
|---|---|
| (a) Clay | 68 parts by weight |
| (b) Sodium lignin sulfonate | 2 parts by weight |
| (c) Polyoxyethylenealkylaryl sulfate | 5 parts by weight |
| (d) Fine silica powder | 25 parts by weight |

A mixture of the above components is mixed with compound No. b-31 in a weight ratio of 4:1 to obtain a wettable powder.

FORMULATION EXAMPLE 5

| | |
|---|---|
| (a) Compound No. b-35 | 50 parts by weight |
| (b) Oxylated polyalkylphenyl phosphate-triethanolamine | 2 parts by weight |
| (c) Silicone | 0.2 part by weight |
| (d) Water | 47.8 parts by weight |

The above components are uniformly mixed and pulverized to obtain a base liquid, and

| (e) Sodium polycarboxylate | 5 parts by weight |
| (f) Anhydrous sodium sulfate | 42.8 parts by weight | are added, and the mixture is uniformly mixed and dried to obtain water-dispersible granules.

FORMULATION EXAMPLE 6

| (a) Compound No. b-48 | 5 parts by weight |
| (b) Polyoxyethyleneoctylphenyl ether | 1 part by weight |
| (c) Phosphoric acid ester of polyoxyethylene | 0.1 part by weight |
| (d) Granular calcium carbonate | 93.5 parts by weight |

The above components (a) to (c) are preliminarily uniformly mixed and diluted with a proper amount of acetone, and then the mixture is sprayed onto the component (d), and acetone is removed to obtain granules.

FORMULATION EXAMPLE 7

| (a) Compound No. a-47 | 2.5 parts by weight |
| (b) N-methyl-2-pyrrolidone | 2.5 parts by weight |
| (c) Soybean oil | 95.0 parts by weight |

The above components are uniformly mixed and dissolved to obtain an ultra low volume formulation.

FORMULATION EXAMPLE 8

| (a) Compound No. a-55 | 5 parts by weight |
| (b) N,N'-dimethylacetamide | 15 parts by weight |
| (c) Polyoxyethylenealkylaryl ether | 10 parts by weight |
| (d) xylene | 70 parts by weight |

The above components are uniformly mixed to obtain an emulsifiable concentrate.

What is claimed is:

1. An acrylonitrile compound of the following formula (I) or its salt:

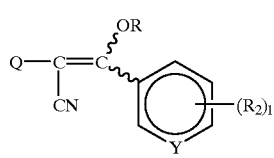

(I)

wherein Q is

Qa

, or

Qd

Y is $=C(R_4)-$, $R_1$ is alkyl, haloalkyl, alkoxyalkyl, alkylthioalkyl, alkenyl, haloalkenyl, alkynyl, haloalkynyl, $-C(=O)R_5$, $-C(=S)R_5$, $-S(O)_wR_5$ or $-CH_2R_9$, each of $R_2$ and $R_3$ is halogen, alkyl which is unsubstituted or substituted, alkenyl which is unsubstituted or substituted, alkynyl which is unsubstituted or substituted, alkoxy which is unsubstituted or substituted, alkenyloxy which is unsubstituted or substituted, alkynyloxy which is unsubstituted or substituted, alkylthio which is unsubstituted or substituted, alkylsulfinyl which is unsubstituted or substituted, alkylsulfonyl which is unsubstituted or substituted, alkenylthio which is unsubstituted or substituted, alkenylsulfinyl which is unsubstituted or substituted, alkenylsulfonyl which is unsubstituted or substituted, alkynylthio which is unsubstituted or substituted, alkynylsulfinyl which is unsubstituted or substituted, alkynylsulfonyl which is unsubstituted or substituted, nitro, cyano, phenyl which is unsubstituted or substituted, phenoxy which is unsubstituted or substituted, phenylthio which is unsubstituted or substituted, phenylsulfinyl which is unsubstituted or substituted phenylsulfonyl which is unsubstituted or substituted, benzyl which is unsubstituted or substituted, benzyloxy which is unsubstituted or substituted, benzylthio which is unsubstituted or substituted, or benzoyl which is unsubstituted or substituted, $R_4$ is hydrogen, halogen, alkyl or haloalkyl, $R_5$ is alkyl which is unsubstituted or substituted, alkenyl which is unsubstituted or substituted, alkynyl which is unsubstituted or substituted, alkoxy which is unsubstituted or substituted, alkenyloxy which is unsubstituted or substituted, alkynyloxy which is unsubstituted or substituted, alkylthio which is unsubstituted or substituted, alkenylthio which is unsubstituted or substituted, alkynylthio which is unsubstituted or substituted, cycloalkyl, cycloalkyloxy, cycloalkylthio, $-N(R_7)R_8$, phenyl which is unsubstituted or substituted, phenoxy which is unsubstituted or substituted, phenylthio which is unsubstituted or substituted, benzyl which is unsubstituted or substituted, benzyloxy which is unsubstituted or substituted, benzylthio which is unsubstituted or substituted, $-J$, $-O-J$ or $-S-J$, each of $R_7$ and $R_8$ is hydrogen, alkyl or alkoxy, $R_9$ is cyano, phenyl which is unsubstituted or substituted, phenoxy which is unsubstituted or substituted, phenylthio which is unsubstituted or substituted, phenylsulfinyl which is unsubstituted or substituted, phenylsulfonyl which is unsubstituted or substituted, benzyl which is unsubstituted or substituted, benzyloxy which is unsubstituted or substituted, benzylthio which is unsubstituted or substituted, benzoyl which is unsubstituted or substituted, $-J$, $-C(=O)R_{10}$, $-C(=S)R_{10}$, $-S(O)_wR_{10}$ or trimethylsilyl, $R_{10}$ is alkyl or alkoxy, J is a 5- or 6-membered heterocyclic group containing from 1 to 4 hetero atoms of at least one type selected from the group consisting of O, S and N (the heterocyclic group is unsubstituted or substituted), l is from 1 to 4, m is from 0 to 5, w is from 0 to 2, when l is 2 or more, a plurality of $R_2$ are the same or different, when m is 2 or more, a plurality of $R_3$ are the same or different, provided that the following compounds are excluded: 3-(4-chlorophenyl)-2-phenyl- 3-ethoxyacrylonitrile, 2-(3,5-dimethoxyphenyl)-3-(2-methoxy-4-methylphenyl)-3-acetoxyacrylonitrile, and 2-(3,5-dimethoxyphenyl)-3-(2,6-dimethoxy-4-methylphenyl)-3-acetoxyacrylonitrile.

2. The acrylonitrile compound or its salt according to claim 1, wherein the substituent for the alkyl which is substituted, the alkenyl which is substituted, the alkynyl which is substituted, the alkoxy which is substituted, the alkenyloxy which is substituted, the alkynyloxy which is substituted, the alkylthio which is substituted, the alkylsulfinyl which is substituted, the alkylsulfonyl which is substituted, the alkenylthio which is substituted, the alkenylsulfinyl which is substituted, the alkenylsulfonyl which is substituted, the alkynylthio which is substituted, the alkynylsulfinyl which is substituted, and the alkynylsulfonyl which is substituted for each of $R_2$ and $R_3$, or the substituent for the alkyl which is substituted, the alkenyl which is substituted, the alkynyl which is substituted, the alkoxy which is substituted, the alkenyloxy which is substituted, the alkynyloxy which is substituted, the alkylthio which is substituted, the alkenylthio which may be substituted, and the alkynylthio which is substituted for $R_5$, is halogen, alkoxy, haloalkoxy, alkoxycarbonyl, alkylthio, alkylsulfinyl, alkylsulfonyl, haloalkylthio, haloalkylsulfinyl, haloalkylsulfonyl, amino, monoalkylamino, dialkylamino, nitro or cyano, the substituent for the phenyl which is substituted, the phenoxy which is substituted, the phenylthio which is substituted, the phenylsulfinyl which is substituted, the phenylsulfonyl which is substituted, the benzyl which is substituted, the benzyloxy which is substituted, the benzylthio which is substituted, and the benzoyl which is substituted for each of $R_2$ and $R_3$, the substituent for the phenyl which is substituted, the phenoxy which is substituted, the phenylthio which is substituted, the benzyl which is substituted, the benzyloxy which is substituted and the benzylthio which is substituted for $R_5$, the substituent for the phenyl which is substituted, the phenoxy which is substituted, the phenylthio which is substituted, the phenylsulfinyl which is substituted, the phenylsulfonyl which is substituted, the benzyl which is substituted, the benzyloxy which is substituted, the benzylthio which is substituted, and the benzoyl which is substituted for $R_9$, or the substituent for the heterocyclic group for J, is halogen, alkyl, haloalkyl, alkoxy, haloalkoxy, nitro, cyano, —S(O)$_w$R$_6$, amino, monoalkylamino or dialkylamino, $R_6$ is alkyl or haloalkyl and w is from 0 to 2.

3. The acrylonitrile compound or its salt according to claim 1, wherein the heterocyclic group for J is furyl, thienyl, pyrrolyl, pyrazolyl, imidazolyl, triazolyl, tetrazolyl, oxazolyl, isoxazolyl, thiazolyl, isothiazolyl, pyridyl, pyrimidinyl, 1-pyrrolidinyl, 1-piperidinyl or 4-morpholino.

4. The acrylonitrile compound or it salt according to claim 1, wherein Q is Qa, and each of $R_2$ and $R_3$ is halogen, alkyl, haloalkyl, alkoxy, haloalkoxy, alkylthio, alkylsulfinyl, alkylsulfonyl, nitro, cyano, phenyl which is unsubstituted or substituted by $M_1$, or phenoxy which is unsubstituted or substituted by $M_1$, $R_5$ is alkyl, haloalkyl, alkoxyalkyl, alkylthioalkyl, aminoalkyl, monoalkylaminoalkyl, dialkylaminoalkyl, alkenyl, haloalkenyl, alkynyl, haloalkynyl, alkoxy, haloalkoxy, alkylthio, haloalkylthio, alkoxycarbonylalkylthio, alkenylthio, haloalkenylthio, alkynylthio, haloalkynylthio, cycloalkyl, cycloalkylthio, —N(R$_7$)R$_8$, phenyl which is unsubstituted or substituted by $M_1$, phenoxy which is unsubstituted or substituted by $M_1$, phenylthio which is unsubstituted or substituted by $M_1$, benzyl which is unsubstituted or substituted by $M_1$, benzylthio which is unsubstituted or substituted by $M_1$, pyridyl which is unsubstituted or substituted by $M_1$, 1-pyrrolidinyl, 1-piperidinyl, 4-morpholino, pyridyloxy which is unsubstituted or substituted by $M_1$, or pyridylthio which is unsubstituted or substituted by $M_1$, $R_9$ is cyano, phenyl which is unsubstituted or substituted by $M_1$, benzyloxy which is unsubstituted or substituted by $M_1$, benzoyl which is unsubstituted or substituted by $M_1$, pyridyl which is unsubstituted or substituted by $M_1$, —C(=O)R$_{10}$, —S(O)$_w$R$_{10}$ or trimethylsilyl, $M_1$ is halogen, alkyl, haloalkyl, alkoxy, haloalkoxy, nitro, cyano, —S(O)$_w$R$_6$ amino, monoalkylamino or dialkylamino, and $R_6$ is alkyl or haloalkyl.

5. The acrylonitrile compound or its salt according to claim 1, wherein Q is Qa, each of $R_2$ and $R_3$ is halogen, alkyl, haloalkyl, alkoxy, haloalkoxy, alkylthio, alkylsulfinyl, alkylsulfonyl, nitro, cyano, phenyl which is unsubstituted or substituted by $M_2$, or phenoxy which is unsubstituted or substituted by $M_2$, $R_5$ is alkyl, haloalkyl, alkoxyalkyl, alkenyl, haloalkenyl, alkynyl, haloalkynyl, alkoxy, haloalkoxy, alkylthio, haloalkylthio, alkoxycarbonylalkylthio, alkenylthio, haloalkenylthio, alkynylthio, haloalkynylthio, cycloalkyl, cycloalkylthio, —N(R$_7$)R$_8$, phenyl which is unsubstituted or substituted by $M_2$, phenoxy which is unsubstituted or substituted by $M_2$, phenylthio which is unsubstituted or substituted by $M_2$, benzyl which is unsubstituted or substituted by $M_2$, benzylthio which is unsubstituted or substituted by $M_2$, pyridyl which is unsubstituted or substituted by $M_2$, 1-pyrrolidinyl, 1-piperidinyl or 4-morpholino, each or $R_7$ and $R_8$ is hydrogen or alkyl, $R_9$ is cyano, phenyl which is unsubstituted or substituted by $M_2$, benzyloxy which is unsubstituted or substituted by $M_2$, benzoyl which is unsubstituted or substituted by $M_2$, pyridyl which is unsubstituted or substituted by $M_2$, —C(=O)R$_{10}$, —S(O)$_w$R$_{10}$ or trimethylsilyl, $M_2$ is halogen, alkyl, haloalkyl, alkoxy, haloalkoxy, nitro, cyano, or —S(O)$_w$R$_6$, and $R_6$ is alkyl.

6. The acrylonitrile compound or its salt according to claim 1, wherein Q is Qa, Y is =C(R$_4$)—, and $R_4$ is hydrogen.

7. The acrylonitrile compound or its salt according to claim 6, wherein $R_2$ is halogen, alkyl or haloalkyl, and 1 is from 1 to 3.

8. The acrylonitrile compound or its salt according to claim 6, wherein $R_1$ is alkoxyalkyl, —C(=O)R$_5$, —C(=S)R$_5$, —S(O)$_w$R$_5$ or —CH$_2$R$_9$, $R_2$ is halogen, alkyl or haloalkyl, $R_3$ is halogen or alkyl, $R_5$ is alkyl, haloalkyl, alkoxyalkyl, alkoxy, haloalkoxy, alkylthio, haloalkylthio, alkoxycarbonylalkylthio, alkenylthio, —N(R$_7$)R$_8$, phenyl which may be substituted by $M_3$, phenoxy which is unsubstituted or substituted by $M_3$, phenylthio which is unsubstituted or substituted by $M_3$, benzyl which is unsubstituted or substituted by $M_3$, pyridyl which is unsubstituted or substituted by $M_3$, 1-pyrrolidinyl or 4-morpholino, each of $R_7$ and $R_8$ is hydrogen or alkyl, $R_9$ is phenyl, $M_3$ is halogen, alkyl or alkoxy, 1 is from 1 to 3, m is from 0 to 3, and w is from 1 to 2.

9. The acrylonitrile compound or its salt according to claim 1, wherein the formula (I) is the formula (I-1):

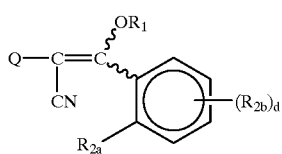

(I-1)

wherein Q is Qa, $R_{2a}$ is haloalkyl, $R_{2b}$ is halogen, alkyl, or haloalkyl, d is from 0 to 2, and m is from 0 to 3.

10. The acrylonitrile compound or its salt according to claim 9, wherein d is 0.

11. The acrylonitrile compound or its salt according to claim 9, wherein $R_1$ is alkoxyalkyl, —C(=O)$R_5$, —C(=S)$R_5$, —S(O)$_w$$R_5$ or —CH$_2$$R_9$, $R_{2b}$ is halogen, alkyl or haloalkyl, $R_3$ is halogen or alkyl, $R_5$ is alkyl, haloalkyl, alkoxyalkyl, alkoxy, haloalkoxy, alkylthio, haloalkylthio, alkoxycarbonylalkylthio, alkenylthio, —N($R_7$)$R_8$, phenyl which is unsubstituted or substituted by $M_3$, phenoxy which is unsubstituted or substituted by $M_3$, phenylthio which is unsubstituted or substituted by $M_3$, benzyl which is unsubstituted or substituted by $M_3$, pyridyl which is unsubstituted or substituted by $M_3$, 1-pyrrolidinyl or 4-morpholino, each $R_7$ and $R_8$ is hydrogen or alkyl, $R_9$ is phenyl, $M_3$ is halogen, alkyl or alkoxy, 1 is from 1 to 3, m is from 0 to 3, and w is from 1 to 2.

12. A process for producing an acrylonitrile compound of the following formula (I) or its salt:

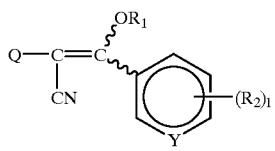

(I)

wherein Q is

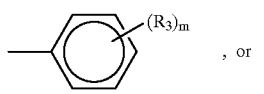

Qa

, or

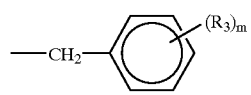

Qd

Y is =C($R_4$)—, $R_1$ is alkyl, haloalkyl, alkoxyalkyl, alkylthioalkyl, alkenyl, haloalkenyl, alkynyl, haloalkynyl, —C(=O)$R_5$, —C(=S)$R_5$, —S(O)$_w$$R_5$ or —CH$_2$$R_9$, each of $R_2$ and $R_3$ is halogen, alkyl which is unsubstituted or substituted, alkenyl which is unsubstituted or substituted, alkynyl which is unsubstituted or substituted, alkoxy which is unsubstituted or substituted, alkenyloxy which is unsubstituted or substituted, alkynyloxy which is unsubstituted or substituted, alkylthio which is unsubstituted or substituted, alkylsulfinyl which is unsubstituted or substituted, alkylsulfonyl which is unsubstituted or substituted, alkenylthio which is unsubstituted or substituted, alkenylsulfinyl which is unsubstituted or substituted, alkenylsulfonyl which is unsubstituted or substituted, alkynylthio which is unsubstituted or substituted, alkynylsulfinyl which is unsubstituted or substituted, alkynylsulfonyl which is unsubstituted or substituted, nitro, cyano, phenyl which is unsubstituted or substituted, phenoxy which is unsubstituted or substituted, phenylthio which is unsubstituted or substituted, phenylsulfinyl which is unsubstituted or substituted, phenylsulfonyl which is unsubstituted or substituted, benzyl which is unsubstituted or substituted, benzyloxy which is unsubstituted or substituted, benzylthio which is unsubstituted or substituted, or benzoyl which is unsubstituted or substituted, $R_4$ is hydrogen, halogen, alkyl or haloalkyl, $R_5$ is alkyl which is unsubstituted or substituted, alkenyl which is unsubstituted or substituted, alkynyl which is unsubstituted or substituted, alkoxy which is unsubstituted or substituted, alkenyloxy which is unsubstituted or substituted, alkynyloxy which is unsubstituted or substituted, alkylthio which is unsubstituted or substituted, alkenylthio which is unsubstituted or substituted, alkynylthio which is unsubstituted or substituted, cycloalkyl, cycloalkyloxy, cycloalkylthio, —N($R_7$)$R_8$, phenyl which is unsubstituted or substituted, phenoxy which is unsubstituted or substituted, phenylthio which is unsubstituted or substituted, benzyl which is unsubstituted or substituted, benzyloxy which is unsubstituted or substituted, benzylthio which is unsubstituted or substituted, —J, —O—J or —S—J, each of $R_7$ and $R_8$ is hydrogen, alkyl or alkoxy, $R_9$ is cyano, phenyl which is unsubstituted or substituted, phenoxy which is unsubstituted or substituted, phenylthio which is unsubstituted or substituted, phenylsulfinyl which is unsubstituted or substituted, phenylsulfonyl which is unsubstituted or substituted, benzyl which is unsubstituted or substituted, benzyloxy which is unsubstituted or substituted, benzylthio which is unsubstituted or substituted, benzoyl which is unsubstituted or substituted, —J, —C(=O)$R_{10}$, —C(=S)$R_{10}$, —S(O)$_w$$R_{10}$ or trimethylsilyl, $R_{10}$ is alkyl or alkoxy, J is a 5- or 6-membered heterocyclic group containing from 1 to 4 hetero atoms of at least one type selected from the group consisting of O, S and N (the heterocyclic group is unsubstituted or substituted), 1 is from 1 to 4, m is from 0 to 5, w is from 0 to 2, when 1 is 2 or more, a plurality of $R_2$ are the same or different, when m is 2 or more, a plurality of $R_3$ are the same or different, provided that the following compounds are excluded 3-(4-chlorophenyl)-2-phenyl-3-ethoxyacrylonitrile, 2-(3,5-dimethoxyphenyl)-3-(2-methoxy-4-methylphenyl)-3-acetoxyacrylonitrile, and 2-(3,5-dimethoxyphenyl)-3-(2,6-dimethoxy-4-methylphenyl)-3-acetoxyacrylonitrile, which comprises reacting a compound of the formula (II):

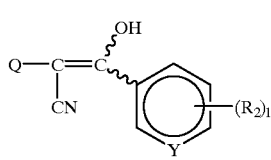

(II)

wherein Q, Y, $R_2$ and 1 are as defined above, with a compound of the formula (III):

$R_1$—X (III)

wherein $R_1$ is as defined above, and X is halogen.

13. A pesticide containing a compound of claim 11, as an active ingredient.

14. An insecticide miticide or nematicide containing a compound of claim 1, as an active ingredient.

15. A compound of the formula (II-1) or its salt:

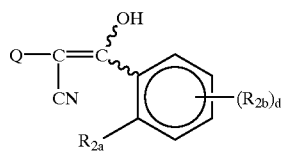
(II-1)

wherein Q is

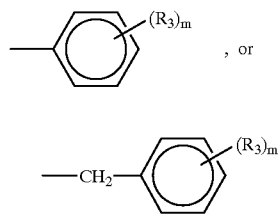

$R_{2a}$ is haloalkyl, $R_{2b}$ is halogen, alkyl or haloalkyl, $R_3$ is halogen, alkyl which is unsubstituted or substituted, alkenyl which is unsubstituted or substituted, alkynyl which is unsubstituted or substituted, alkoxy which is unsubstituted or substituted, alkenyloxy which is unsubstituted or substituted, alkynyloxy which is unsubstituted or substituted, alkylthio which is unsubstituted or substituted, alkylsulfinyl which is unsubstituted or substituted, alkylsulfonyl which is unsubstituted or substituted, alkenylthio which is unsubstituted or substituted, alkenylsulfinyl which is unsubstituted or substituted, alkenylsulfonyl which is unsubstituted or substituted, alkynylthio which is unsubstituted or substituted, alkynylsulfinyl which is unsubstituted or substituted, alkynylsulfonyl which is unsubstituted or substituted, nitro, cyano, phenyl which is unsubstituted or substituted, phenoxy which is unsubstituted or substituted, phenylthio which is unsubstituted or substituted, phenylsulfinyl which is unsubstituted or substituted, phenylsulfonyl which is unsubstituted or substituted, benzyl which is unsubstituted or substituted, benzyloxy which is unsubstituted or substituted, benzylthio which is unsubstituted or substituted, or benzoyl which is unsubstituted or substituted, d is from 0 to 2, m is from 0 to 5, when d is 2, two $R_{2b}$ are the same or different, when m is 2 or more, a plurality of $R_3$ are the same or different.

16. The compound or its salt according to claim 15, wherein Q is Qa.

17. The compound of claim 15, wherein d is o.

18. A method for controlling a pest, which comprises applying the compound as claimed in claim 1, as an active ingredient to the pest.

19. A method for controlling a pest, which comprises applying the compound as claimed in claim 13 as an active ingredient to the pest.

* * * * *